US011567036B2

(12) United States Patent
Hinz et al.

(10) Patent No.: US 11,567,036 B2
(45) Date of Patent: Jan. 31, 2023

(54) CELL ANALYSIS USING CHEMFET SENSOR ARRAY-BASED SYSTEMS

(71) Applicant: LIFE TECHNOLOGIES CORPORATION, Carlsbad, CA (US)

(72) Inventors: Wolfgang Hinz, Killingworth, CT (US); John Donohue, Southbury, CT (US); Daniel Beacham, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 619 days.

(21) Appl. No.: 16/568,133

(22) Filed: Sep. 11, 2019

(65) Prior Publication Data

US 2020/0088676 A1 Mar. 19, 2020

Related U.S. Application Data

(60) Provisional application No. 62/848,842, filed on May 16, 2019, provisional application No. 62/730,960, filed on Sep. 13, 2018.

(51) Int. Cl.
*G01N 27/414* (2006.01)
*C09D 189/00* (2006.01)
(Continued)

(52) U.S. Cl.
CPC ....... *G01N 27/4145* (2013.01); *C09D 189/00* (2013.01); *G01N 27/283* (2013.01);
(Continued)

(58) Field of Classification Search
CPC ............ G01N 27/414; G01N 27/4145; G01N 33/4836
See application file for complete search history.

(56) References Cited

U.S. PATENT DOCUMENTS 8,349,167 B2 1/2013 Rothberg et al.
8,546,128 B2 10/2013 Schultz et al.
(Continued)

OTHER PUBLICATIONS

Milgrew et al., "A Fully-Integrated CMOS Microsensor Array for Imaging the Hydrogen Ion Activity of Living Cells," Twelfth International Conference on Miniaturized Systems for Chemistry and Life Sciences Oct. 12-16, 2008, San Diego, California, USA (Year: 2008).*
(Continued)

*Primary Examiner* — Alexander S Noguerola

(57) ABSTRACT

Various cell analysis systems of the present teachings can measure the electrical and metabolic activity of single, living cells with subcellular addressability and simultaneous data acquisition for between about 10 cells to about 500,000 cells in a single analysis. Various sensor array devices of the present teachings can have sensor arrays with between 20 million to 660 million ChemFET sensors built into a massively paralleled array and can provide for simultaneous measurement of cells with data acquisition rates in the kilohertz (kHz) range. As various ChemFET sensor arrays of the present teachings can detect chemical analytes as well detect changes in cell membrane potential, various cell analysis systems of the present teachings also provide for the controlled chemical and electrical interrogation of cells.

32 Claims, 34 Drawing Sheets

(51) Int. Cl.
 G01N 27/28 (2006.01)
 G01N 27/30 (2006.01)
 G01N 27/407 (2006.01)
 G01N 33/483 (2006.01)

(52) U.S. Cl.
 CPC ......... *G01N 27/30* (2013.01); *G01N 27/4075* (2013.01); *G01N 27/4148* (2013.01); *G01N 33/4836* (2013.01)

(56) References Cited

U.S. PATENT DOCUMENTS

| 8,673,627 | B2 | 3/2014 | Nobile et al. | |
|---|---|---|---|---|
| 2009/0032411 | A1* | 2/2009 | Peitz | G01N 33/554 435/325 |
| 2012/0143531 | A1* | 6/2012 | Davey | G01N 33/48785 73/40.5 R |

OTHER PUBLICATIONS

Bonk et al., "Design and Characterization of a Sensorized Microfluidic Cell-Culture System with Electro-Thermal Micro-Pumps and Sensors for Cell Adhesion, Oxygen, and pH on a Glass Chip," Biosensors 2015, 5, 513-536; doi: 10.3390/bios5030513 (Year: 2015).*

Florian Larramendy et al . . . MISFET-based biosensing interface for neurons guided growth and neuronal electrical activities recording. Sensors and Actuators B: Chemical, Elsevier, 2014, 203, pp. 375-381. 10.1016/j.snb.2014.06.106. hal-01504965 (Year: 2014).*

Lorenzelli et al., "Bioelectrochemical signal monitoring of in-vitro cultured cells by means of an automated microsystem based on solid state sensor-array," Biosensors and Bioelectronics 18 (2003) 621-626 (Year: 2003).*

Schaffhauser et al., "Measurement of Rapid Amiloride-Dependent pH Changes at the Cell Surface Using a Proton-Sensitive Field-Effect Transistor," Biosensors 2016,6, 11; doi:10.3390/bios6020011 (Year: 2016).*

Cohen et al., "Depletion type floating gate-channel MOS transistor for recording action potentials generated by cultured neurons," Biosensors and Bioelectronics 19 (2004) 1703-1709 (Year: 2004).*

Online Wiktionary definition of "electroscopic", downloaded Apr. 18, 2022 (Year: 2021).*

Online Wiktionary definition of electroscope, downloaded Apr. 18, 2022 (Year: 2020).*

Duarte-Guevara et al, "Characterization of a 1024 × 1024 DG-BioFET platform," Sensors and Actuators B: Chemical 250 (2017) 100-110 (Year: 2017).*

Lambacher et al., "Electrical Imaging of Neuronal Activity by Multi-Transistor-Array (MTA) Recording at 7.8 [mu]m Resolution", Applied Physics A Materials Science & Processing, vol. 79, No. 7, Aug. 5, 2004, pp. 1607-1611.

Lambacher et al., "Identifying Firing Mammalian Neurons In Networks With High-Resolution Multi-Transistor Array (MTA)", Applied Physics A, Materials Science & Processing, vol. 102, No. 1, Sep. 16, 2010, pp. 1-11.

PCT/US2019/050673, Search Report and Written Opinion, dated Nov. 25, 2019.

Qing et al., "Nanowire Transistor Arrays for Mapping Neural Circuits in Acute Brain Slices", Proceedings Of The National Academy Of Sciences, National Academy Of Sciences, vol. 107, No. 5, Feb. 2, 2010, pp. 1882-1887.

Walsh et al., "Application of Ion-Sensitive Field Effect Transistors for Ion Channel Screening", Biosensors And Bioelectronics, vol. 54, Nov. 22, 2013, pp. 448-454.

Schaffhauser et al. "Measurement of Rapid Amiloride-Dependent pH Changes at the Cell Surface Using a Proton-Sensitive Field-Effect Transistor" *Biosensors*, 2016, vol. 6, No. 11.

Schaffhauser et al., "An Integrated Field-Effect Microdevice for Monitoring Membrane Transport in Xenopus laevis Oocytes via Laternal Proton Diffusion" *Plosone*, Jul. 2012, vol. 7, Issue 7.

Lopez et al., "A Multimodal CMOS MEA for High-Throughput Intracellular Action Potential Measurements and Impedance Spectroscopy in Drug-Screening Applications," *IEEE Journal of Solid-State Circuits*, vol. 53, No. 11, Nov. 2018.

Milgrew et al. "The Development of Scalable Sensor Arrays Using Standard CMOS Technology," *Sensors and Actuators*, B 103, 2004, pp. 37-42.

\* cited by examiner

| Cell Size | Device | Pitch (μm) | Pixel Size (μm x μm) | Pixel Area μm²/pixel | Pixels per Cell Area | % Pixel Coverage | Rows per Cell D | FR$_{max}$ per Row (fps) | FR$_{max}$ per Row$_{Cell\ D}$ (fps) |
|---|---|---|---|---|---|---|---|---|---|
| Extra large $\bar{D} = 100\ \mu m$ $\bar{A} = 7854\ \mu m^2$ | Chip 1 | 3.36 | 2.910 x 3.360 | 9.78 | 803 | 0.1% | 30 | 75,000 | 2,500 |
| | Chip 2 | 1.68 | 1.453 x 1.680 | 2.44 | 3,219 | 0.03% | 60 | 75,000 | 1,250 |
| | Chip 3 | 1.26 | 1.093 x 1.262 | 1.38 | 5,691 | 0.02% | 79 | 162,000 | 2,051 |
| | Chip 4 | 0.85 | 0.733 x 0.846 | 0.62 | 12,668 | 0.008% | 118 | 162,000 | 1,373 |
| Large $\bar{D} = 50\ \mu m$ $\bar{A} = 1964\ \mu m^2$ | Chip 1 | 3.36 | 2.910 x 3.360 | 9.78 | 201 | 0.5% | 15 | 75,000 | 5,000 |
| | Chip 2 | 1.68 | 1.453 x 1.680 | 2.44 | 805 | 0.1% | 30 | 75,000 | 2,500 |
| | Chip 3 | 1.26 | 1.093 x 1.262 | 1.38 | 1,423 | 0.07% | 40 | 162,000 | 4,050 |
| | Chip 4 | 0.85 | 0.733 x 0.846 | 0.62 | 3,168 | 0.03% | 59 | 162,000 | 2,746 |
| Medium $\bar{D} = 25\ \mu m$ $\bar{A} = 491\ \mu m^2$ | Chip 1 | 3.36 | 2.910 x 3.360 | 9.78 | 50 | 2% | 7 | 75,000 | 10,714 |
| | Chip 2 | 1.68 | 1.453 x 1.680 | 2.44 | 201 | 0.5% | 15 | 75,000 | 5,000 |
| | Chip 3 | 1.26 | 1.093 x 1.262 | 1.38 | 356 | 0.2% | 20 | 162,000 | 8,100 |
| | Chip 4 | 0.85 | 0.733 x 0.846 | 0.62 | 792 | 0.1% | 29 | 162,000 | 5,587 |
| Small $\bar{D} = 10\ \mu m$ $\bar{A} = 78\ \mu m^2$ | Chip 1 | 3.36 | 2.910 x 3.360 | 9.78 | 8 | 12% | 3 | 75,000 | 25,000 |
| | Chip 2 | 1.68 | 1.453 x 1.680 | 2.44 | 32 | 3% | 6 | 75,000 | 12,500 |
| | Chip 3 | 1.26 | 1.093 x 1.262 | 1.38 | 56 | 2% | 8 | 162,000 | 20,250 |
| | Chip 4 | 0.85 | 0.733 x 0.846 | 0.62 | 126 | 0.8% | 12 | 162,000 | 13,500 |
| Very Small $\bar{D} = 5\ \mu m$ $\bar{A} = 20\ \mu m^2$ | Chip 1 | 3.36 | 2.910 x 3.360 | 9.78 | 2 | 50% | 1 | 75,000 | 75,000 |
| | Chip 2 | 1.68 | 1.453 x 1.680 | 2.44 | 8 | 12% | 3 | 75,000 | 25,000 |
| | Chip 3 | 1.26 | 1.093 x 1.262 | 1.38 | 14 | 7% | 4 | 162,000 | 40,500 |
| | Chip 4 | 0.85 | 0.733 x 0.846 | 0.62 | 32 | 3% | 6 | 162,000 | 27,000 |

Table II: Summary of attributes for exemplary sensor array devices for cell analysis

FIG. 3

| Cell Type | Device | Pitch (μm) | Pixel Size (μm × μm) | Pixel Area μm²/pixel | Pixels per Cell Area | % Pixel Coverage | Rows per Cell D | $FR_{max}$ per Row (fps) | $FR_{max}$ per $Row_{Cell\ D}$ (fps) |
|---|---|---|---|---|---|---|---|---|---|
| RNHC $\overline{D}$ = 20-100 μm $\overline{A}$ = 314 μm² - 7,854 μm² | Chip 1 | 3.36 | 2.910 × 3.360 | 9.78 | 32-803 | 3.0-0.1% | 6-30 | 75,000 | 12,500-2,500 |
| | Chip 2 | 1.68 | 1.453 × 1.680 | 2.44 | 129-3,219 | 0.8-0.03% | 12-60 | 75,000 | 6,250-1,250 |
| | Chip 3 | 1.26 | 1.093 × 1.262 | 1.38 | 228-5,691 | 0.4-0.02% | 16-79 | 162,000 | 10,125-2,051 |
| | Chip 4 | 0.85 | 0.733 × 0.846 | 0.62 | 506-12,668 | 0.2-0.008% | 24-118 | 162,000 | 6,750-1,373 |
| HASMC $\overline{D}$ = 25 μm $\overline{A}$ = 491 μm² | Chip 1 | 3.36 | 2.910 × 3.360 | 9.78 | 50 | 2% | 7 | 75,000 | 10,714 |
| | Chip 2 | 1.68 | 1.453 × 1.680 | 2.44 | 201 | 0.5% | 15 | 75,000 | 5,000 |
| | Chip 3 | 1.26 | 1.093 × 1.262 | 1.38 | 356 | 0.3% | 20 | 162,000 | 8,100 |
| | Chip 4 | 0.85 | 0.733 × 0.846 | 0.62 | 792 | 0.1% | 29 | 162,000 | 5,586 |
| U-2OS $\overline{D}$ = 19 μm $\overline{A}$ = 284 μm² | Chip 1 | 3.36 | 2.910 × 3.360 | 9.78 | 29 | 3% | 6 | 75,000 | 12,500 |
| | Chip 2 | 1.68 | 1.453 × 1.680 | 2.44 | 116 | 0.7% | 11 | 75,000 | 6,818 |
| | Chip 3 | 1.26 | 1.093 × 1.262 | 1.38 | 206 | 0.5% | 15 | 162,000 | 10,800 |
| | Chip 4 | 0.85 | 0.733 × 0.846 | 0.62 | 458 | 0.2% | 22 | 162,000 | 7,364 |
| HeLa $\overline{D}$ = 18 μm $\overline{A}$ = 254 μm² | Chip 1 | 3.36 | 2.910 × 3.360 | 9.78 | 26 | 4% | 5 | 75,000 | 15,000 |
| | Chip 2 | 1.68 | 1.453 × 1.680 | 2.44 | 104 | 1% | 11 | 75,000 | 6,818 |
| | Chip 3 | 1.26 | 1.093 × 1.262 | 1.38 | 184 | 0.5% | 14 | 162,000 | 11,571 |
| | Chip 4 | 0.85 | 0.733 × 0.846 | 0.62 | 410 | 0.2% | 21 | 162,000 | 7,714 |
| HEPG2 $\overline{D}$ = 15 μm $\overline{A}$ = 177 μm² | Chip 1 | 3.36 | 2.910 × 3.360 | 9.78 | 18 | 6% | 4 | 75,000 | 18,750 |
| | Chip 2 | 1.68 | 1.453 × 1.680 | 2.44 | 72 | 1% | 9 | 75,000 | 8,333 |
| | Chip 3 | 1.26 | 1.093 × 1.262 | 1.38 | 128 | 0.8% | 12 | 162,000 | 13,500 |
| | Chip 4 | 0.85 | 0.733 × 0.846 | 0.62 | 285 | 0.4% | 18 | 162,000 | 9,000 |
| MMM $\overline{D}$ = 6 μm $\overline{A}$ = 28 μm² | Chip 1 | 3.36 | 2.910 × 3.360 | 9.78 | 3 | 33% | 2 | 75,000 | 37,500 |
| | Chip 2 | 1.68 | 1.453 × 1.680 | 2.44 | 11 | 9% | 4 | 75,000 | 18,750 |
| | Chip 3 | 1.26 | 1.093 × 1.262 | 1.38 | 20 | 5% | 5 | 162,000 | 32,400 |
| | Chip 4 | 0.85 | 0.733 × 0.846 | 0.62 | 45 | 2% | 7 | 162,000 | 23,142 |

Table III: Summary of attributes for exemplary sensor array devices for cell lines of FIG. 7A-15C.

FIG. 16

CELL ANALYSIS USING CHEMFET SENSOR ARRAY-BASED SYSTEMS

CROSS-REFERENCE TO RELATED APPLICATIONS

This application claims benefit of U.S. Provisional Application No. 62/730,960 filed Sep. 13, 2018, and of U.S. Provisional Application No. 62/848,842 filed May 16, 2019. Both applications named in this section are incorporated herein by reference; each in its entirety.

OVERVIEW

Electrophysiological and metabolic phenotyping of cell behaviors remain crucial avenues of research in modern cell biology with large unmet needs for researchers in areas of, for example, engineered tissues, primary cell types and oncology discovery. Successful measurements of cellular excitability are currently hindered by cumbersome patch clamp and microelectrode voltammetry methods, while interrogations of metabolic function remain hampered by the technical limitations of large scale population and biochemical workflows, inefficiently deployed to access crucial metrics of single cell behavior.

It is becoming more evident that while it is not possible or practical to measure all possible interactions among 20,000 genes and 200,000 proteins within a cell, that the study of model systems at the single cell level would provide greater insight into normal cell physiology and alterations during pathological conditions such as cancer, diabetes and neurodegenerative disease. Recent applications that highlight the advantages of single cell studies vs. cell population studies include, for example, studies of transcriptomics and aging, studies of signaling pathways within cells and bioenergetic measurements of metabolism.

Accordingly, there is a need in the art for systems and methods that can provide an end user with the tools for interrogation of single cells in a population and that would allow cell level, discrete measurements of temporal responses in a high-throughput multiplex manner.

BRIEF DESCRIPTION OF THE DRAWINGS

A better understanding of the features and advantages of the present teachings will be obtained by reference to the following detailed description that sets forth illustrative embodiments, and by reference to the accompanying drawings of which:

FIG. 3 is a table of displaying ChemFET system attributes for cell analysis across a range of cell sizes.

FIG. 16 is a table of displaying ChemFET system attributes for cell analysis for the cell lines of FIG. 7A through FIG. 15C.

DETAILED DESCRIPTION

Systems and methods of the present teachings are related to cell analysis systems based on chemical field effect transistor (ChemFET) sensor array technology. Various cell analysis systems of the present teachings can measure the electrical and metabolic activity of single, living cells with subcellular addressability and simultaneous data acquisition for between about 10 cells to about 500,000 cells in a single analysis. Various sensor array devices of the present teachings can have sensor arrays with between 20 million to 660 million ChemFET sensors built into a massively paralleled array, in which the sensors of a sensor array can have a pitch of between about 3.36 µm to about 850 nm, respectively. Further, various cell analysis systems of the present teachings can provide for simultaneous measurement of cells with data acquisition rates in the kilohertz (kHz) range. Moreover, a fully automated fluidic system integrated into various cell analysis systems of the present teaching allows for the tightly controlled application, for example, of chemical agents used in various studies for which the measurement of cell responses to various types of chemical interrogation is indicated. As various ChemFET sensor arrays of the present teachings can detect chemical analytes as well detect changes in cell membrane potential, controlled electrical stimulus can also be used to interrogate cells in various cell analysis systems of the present teachings.

Chemical Field Effect Transistor (ChemFET) Arrays for Cell Analysis

Figure 1:
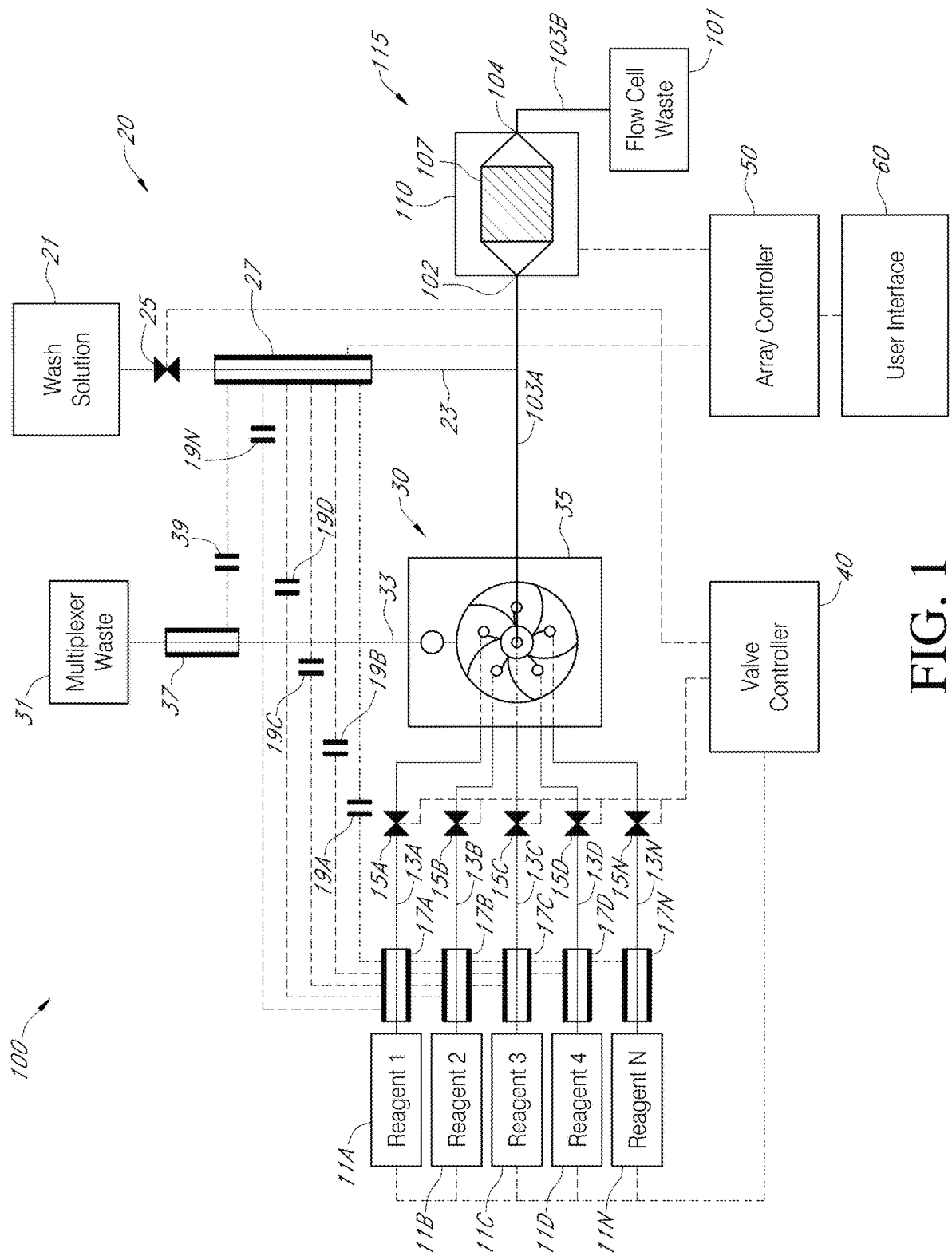
FIG. 1 is a block diagram depicting a chemical field effect transistor (ChemFET)-based cell analysis system according to various embodiments of systems and methods of the present teachings.

FIG. 1 illustrates generally a block diagram of exemplary components of cell analysis system 100 according to the present teachings. As depicted in FIG. 1, cell analysis system 100 can include various fluidic systems, as well as array controller 50, user interface 60, and sensor array device assembly 115. As will be described in more detail herein, various cell analyses can be performed using sensor array device 110 of sensor array device assembly 115.

Figure 2A:
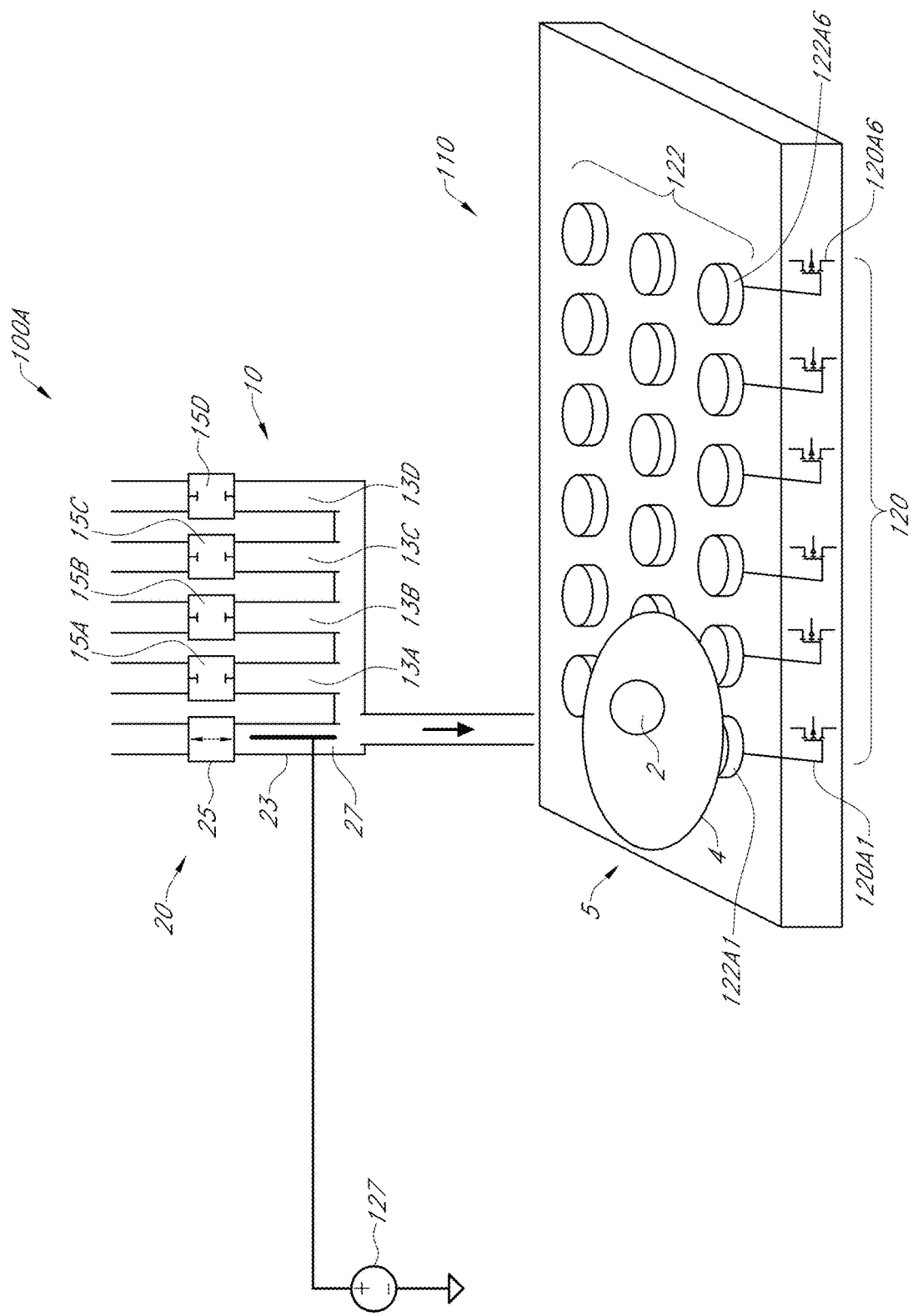
FIG. 2A is a schematic depiction of a cell positioned on a cell analysis system of the present teachings.

FIG. 2A illustrates generally a graphic depiction of cell analysis system 100A. As depicted in FIG. 2A cell 5, with nucleus 2 and cell membrane 4, is positioned over a plurality of a subset of microwells, thereby defining an area of contact or footprint that cell 5 occupies over a corresponding subset of sensors. As recited herein, "area of contact" and "footprint" can be used interchangeably. Cell analysis system 100A shares many of the same features as described for the schematic depiction of cell analysis system 100 of FIG. 1. Cell analysis system 100A of FIG. 2A can include reagent fluidic system 10 and wash solution fluidic system 20. Reagent fluidic system 10 can include a plurality of reagent containers, such as reagent containers 11A-11D of FIG. 2A. Each reagent container can be in fluid communication with a reagent fluid line, such as reagent fluid lines 13A-13D, of FIG. 2A. Flow from each reagent fluid line of a cell analysis system of the present teachings can be controlled by a valve, such as reagent fluid line valves 15A-15D of FIG. 2A. Wash solution fluidic system 20 can include wash solution container 21, which can contain a wash solution of known electrolyte composition, as well as wash solution fluid line 23, wash solution fluid line valve 25, and reference electrode 27 in wash solution fluid line 23. As will be described in more detail herein, reference electrode 27 can provide a stable reference voltage 127 for sensor in a sensor array device. As such, sensor array device 110 of FIG. 2A can be in fluid communication with reagent fluidic system 10 and wash solution fluidic system 20. Though not shown in FIG. 2A, an additional electrode that can be in communication with the sensor array device can be utilized to provide an electrical stimulus to cells on a sensor array, such as cell 5 of FIG. 2A.

Sensor array device 110 can include sensor array or pixel array 120. As recited herein, the terms "sensor" and "pixel," as well the terms "device" and "chip" and derivatives of these terms can be used interchangeably. Additionally, "sensor array" and "ChemFET sensor array," and derivatives thereof can be used interchangeably. Though depicted in FIG. 2A as regular array two-dimensional array, various embodiments of sensor arrays of the present teachings can be arranged in a variety of array geometries, for example, in an hexagonal closest packed geometry. Sensor array device 110 can include a microwell array 122, which as illustrated in FIG. 2A, depicts each microwell cooperatively engaged with each sensor or pixel in sensor array 120, so that each microwell 122A1 through microwell 122A6 is cooperatively engaged with a corresponding sensor 120A1 through sensor 120A6. However, for various embodiments of sensor array devices of the present teachings, there can be more than one pixel per well. As will be described in more detail herein, various types of sensor array devices of the present teachings can be fabricated with a defined but different microwell depth. Still other types of sensor array devices of the present teachings may have no microwell structures formed over the sensor array. Each sensor of sensor array 120 can have a sensing surface in fluidic communication with the fluid in the microwell array 122. For various embodiments of cell analysis system 100 of the present teachings, each sensor of sensor array 120 can be a chemical field-effect transistor (ChemFET), where each sensor in sensor array 120 includes at least one chemically-sensitive field-effect transistor. According to the present teachings sensor array 120 can include ChemFETs that can be fabricated with sensing surfaces modified to be selective for the analysis of a targeted chemical species of interest for cell biology, for example, such as glucose, sucrose, lactate and urea. By way of another non-limiting example, ion sensitive field-effect transistors (ISFETs) can have sensing surfaces modified to be selective for various ions of interest; particularly for various cell metabolism studies, such as hydrogen, potassium, calcium and chloride.

In that regard, the present inventors have recognized that various embodiments of cell analysis systems of the present teachings can be used to monitor changes in, for example, cell electrophysiology and metabolism for cells subjected to any of a variety of conditions or stimuli. Moreover, the present inventors have recognized that any change in the state of a cell that can cause a change in potential of a sensing surface of a ChemFET sensor can be monitored by sensors of various embodiments of a ChemFET sensor array of the present teachings. For example, the present inventors have recognized that a cell is capacitively coupled to the sensing surface of a sensor, so that as the electrical potential across a cell membrane changes in response to a chemical or electrical stimulus, the changing electrical potential across the cell membrane can be detected by sensors of various embodiments of a ChemFET sensor array of the present teachings. Additionally, any change, for example, in cell metabolism that can cause a change in potential of the sensing surface of a ChemFET sensor can be detected by sensors of various embodiments of a ChemFET sensor array of the present teachings. As will be described in more detail herein, such changes can be locally detected in association with an area of contact or footprint of a cell anchored on a sensor array surface or can be detected in areas not associated with a cell footprint, for example, such as for cellular efflux that may stream from a cell in response to a condition or stimulus.

Data collected in experiments monitoring cellular response to various stimuli with various embodiments of ChemFET sensor array devices of the present teachings can be presented to an end user in a number of formats. In one format, temporal response is presented as detector counts that can be readily correlated to millivolt (mV) change in sensing surface potential as a function of time. In another format, for any of a selected time over a course of a selected application, a spatial visualization of cells can be presented as an electroscopic image. The present inventors have recognized that as electroscopic imaging is predicated on a variety of responses that can be elicited for living cells, it can useful, for example, as a general tool for visualizing cells on a sensor array. For example, by reviewing an electroscopic image of cells anchored on a sensor array, an end-user can select an area of interest as part of application configuration before running an experiment. As will be described in more detail herein, windowing down a selected area of a sensor array device thereby increases the data rate for the experiment. According to the present teachings, the substantial pixel coverage over a footprint of a cell coupled with high data rate can provide subcellular monitoring of, for example, action potential of various excitable cells for which a data rate in the sub-millisecond range may be required.

Figure 2B:
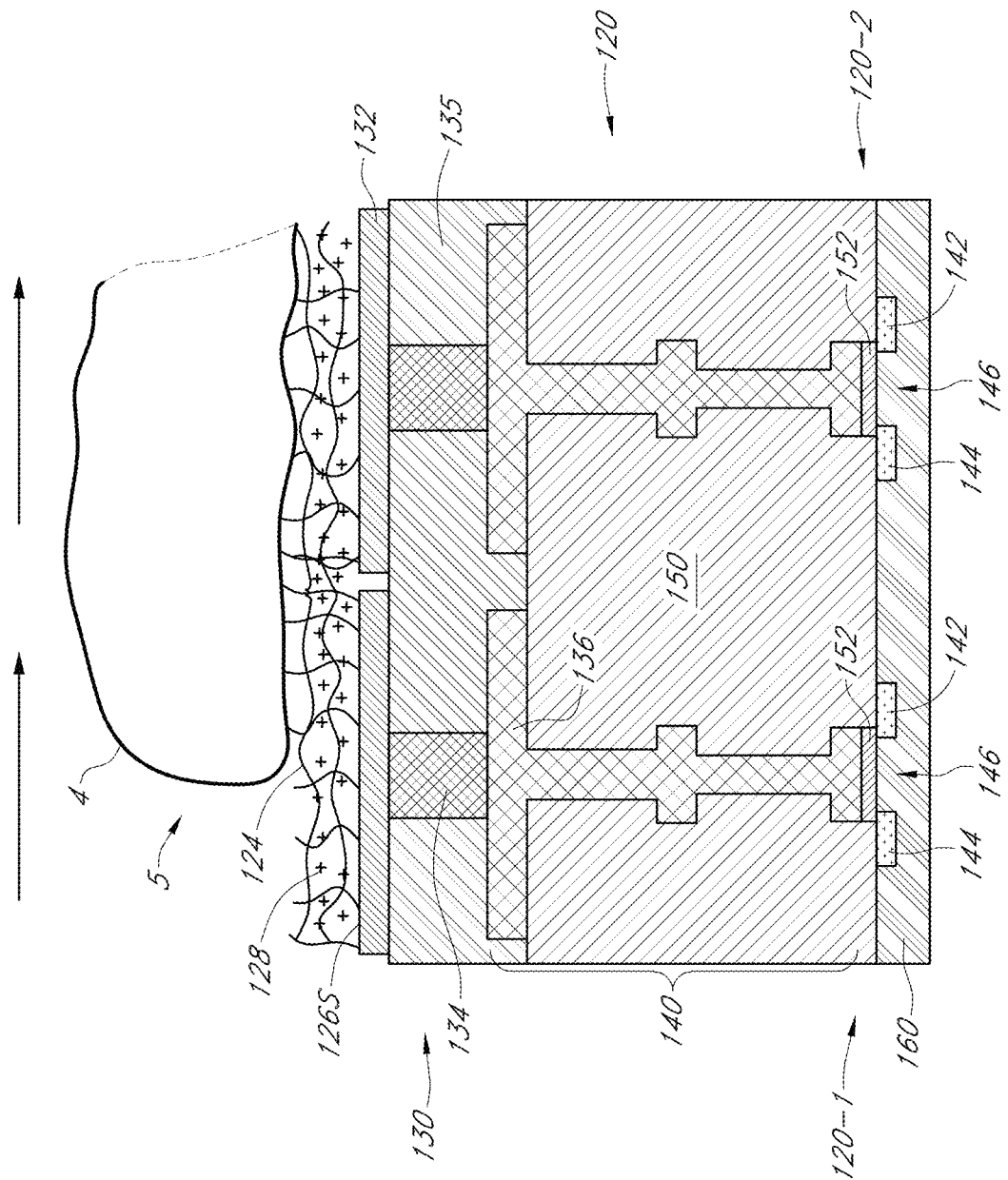
FIG. 2B is a schematic section view of a cell positioned on a sensor device of the present teaching.

In FIG. 2B, a partial section view of sensor array 120 is depicted with first sensor 120-1 and second sensor 120-2. In various embodiments of a sensor array device of the present teachings, sensor array 120 can include floating gate upper portion 130 coupled to sensor floating gate structure 140. Alternatively, for various embodiments of a sensor array device of the present teachings, sensor array 120 can include sensor floating gate structure 140. As will be described in more detail herein, floating gate upper portion 130 can include a top metal layer, sensor plate 132, as well as metal via 134, formed in dielectric 135.

Sensor floating gate structure 140 can have metal layer 136 coupled to sensor plate 132 through metal via 134. Metal layer 136 is the uppermost floating gate conductor in sensor floating gate structure 140. In the illustrated example, sensor floating gate structure 140 includes multiple layers of conductive material within layers of dielectric material 150. Sensors 120-1 and 120-2 can include conduction terminals including source/drain region 142 and source/drain region 144 within semiconductor substrate 160. Source/drain region 142 and source/drain region 144 comprise doped semiconductor material having a conductivity of a type different from the conductivity type of substrate 160. For example, source/drain region 142 and source/drain region 144 can comprise doped P-type semiconductor material, and substrate 160 can comprise doped N-type semiconductor material. Channel region 152 separates source/drain region 142 and source/drain region 144. Floating gate structure 140 overlies channel region 146, and is separated from substrate 160 by gate dielectric 152. Gate dielectric 152 can be silicon dioxide, for example. Alternatively, other suitable dielectrics can be used for gate dielectric 152 such as, for example materials with higher dielectric constants, silicon carbide (SiC), silicon nitride ($Si_3N_4$), silicon oxynitride ($Si_2N_2O$), aluminum nitride (AlN), hafnium dioxide ($HfO_2$), tin oxide ($SnO_2$), cesium oxide ($CeO_2$), titanium oxide ($TiO_2$), tungsten oxide ($WO_3$), aluminum oxide ($Al_2O_3$), lanthanum oxide ($La_2O_3$), gadolinium oxide ($Gd_2O_3$), and any combination thereof.

As will be described in more detail herein, sensing surface 126S of sensor plate 132 can act as the sensor surface for monitoring changes in, for example, cell electrophysiology and metabolism for cells subjected to any of a variety of conditions or stimuli. In that regard, cell 5 shown in FIG. 2B as a partial section of a cell, is depicted as positioned over sensor plate 132 of sensors 120-1 and 120-2. Cell 5 is depicted as anchored to sensor array 120 via surface coating 124. Surface coating 124 can be any cell-compatible material, such as various biopolymer materials including poly-D-lysine, laminin, fibronectin, collagen, and combinations thereof, as well as various preparations of extracellular matrix (ECM). An end user can run applications using cell analysis systems of the present teachings that controllably flow various reagents and solutions can over the surface of sensor array 120, as indicated by the arrows at the top of FIG. 2B.

Sensors 120-1 and 120-2 are responsive to changes in the surface potential of ion layer 128 proximate to sensing surface 126S, which can cause changes in the voltage on floating gate 140. As such, an applied reference voltage, as previously described herein for FIG. 2A, ensures that the voltage of the floating gate exceeds a threshold voltage, providing that small changes in the floating gate voltage can cause current to flow through channel region 146, resulting in an output signal for sensors 120-1 and 120-2. In that regard, changes to the surface potential of ion layer 128 can be measured by measuring the current in channel region 146 between, for example, source region 142 and drain region 144. As such, sensors 120-1 and 120-2 can be used directly to provide a current-based output signal on an array line connected to source region 142 or drain region 144, or indirectly with additional circuitry to provide a voltage-based output signal.

As described herein, any change in the state of cell 5 that can alter the surface potential in ion layer 128 can be monitored by various embodiments of ChemFET sensor array devices of the present teachings. With respect to output signal, any cell activity that can increase surface potential would result in an output signal of positive amplitude for a ChemFET sensor, while any cell activity that can decrease surface potential would result in an output signal of negative amplitude for a ChemFET sensor. In that regard, any change in the state of a cell that can change the surface potential of a ChemFET sensor can result in a measurable output signal. For example, any metabolic activity that can increase ion concentration of a cationic species which an ISFET sensor is selective for would cause an increase in surface potential. The result would be an output signal of positive amplitude for that ISFET sensor. Conversely, any metabolic activity that can decrease ion concentration of a cationic species for which an ISFET sensor is selective for would cause an decrease in surface potential. The result would be an output signal of negative amplitude for that ISFET sensor. In another example, the surface potential can be altered by the capacitive coupling of cell 5 to sensor array 120, so that as the electrical potential across cell membrane 4 changes in response to a chemical or electrical stimulus, the changing electrical potential across the cell membrane can be detected by ChemFET sensors 120-1 and 120-2.

Table I summarizes attributes of exemplary ChemFET sensors of the present teachings.

TABLE I

Exemplary sensor array devices

| Device | Pixels per Device | Pitch (μm) | Pixel Size (μm × μm) | Pixel Area μm²/ pixel | $FR_{max}$ per Device (fps) | $FR_{max}$ per Row (fps) |
| --- | --- | --- | --- | --- | --- | --- |
| A | 20M | 3.36 | 2.910 × 3.360 | 9.78 | 240 | 75,000 |
| B | 40M | 3.36 | 2.910 × 3.360 | 9.78 | 120 | 75,000 |
| C | 165M | 1.68 | 1.453 × 1.680 | 2.44 | 30 | 75,000 |
| D | 300M | 1.26 | 1.093 × 1.262 | 1.38 | 30 | 162,000 |
| E | 660M | 0.85 | 0.733 × 0.846 | 0.62 | 15 | 162,000 |

Various embodiments of a sensor array device of the present teachings can have between about 20M to about 660M pixels, with a center-to-center spacing between each sensor; or the pitch, of between about 850 nm to about 3.36 μm. With respect to data collection, a collection of sensor output signals from all sensors in an array constitutes a frame of data. For various sensor array devices of the present teachings with between about 20 million pixels to about 660 million pixels, a frame of is a data file of substantial size, which is collected in units of hertz (Hz) as frames per second. Further, there is an inverse relationship between an area of interest selected representing the number of pixels and the rate at which data can be collected, so that by selecting a smaller subset of pixels to monitor, i.e. by windowing down the area of a sensor array device over which data is collected, frame rate can be increased. The impact of windowing down is evidenced in Table I by comparison of the values entered in the second to last column, which is maximum frame rate for collecting data from an entire device, to the values entered into the last column, which is maximum frame rate for collecting data from a single row of a device. As such, by windowing down to collect data from a single row, frame rate is substantially increased.

Additionally, as provided in Table I, the only difference between Device A and Device B is the number of total sensors per device, in which there are double the number of sensors per Device A versus Device B. As shown in Table 1, the frame rate for Device B is half that of Device A, consistent with an inverse relationship between number of pixels and the rate at which data can be collected. As such, a device with a desirable frame rate matched to an application can be selected.

Accordingly, for various embodiments of cell analysis systems of the present teachings, an end user can select a sensor array device from a variety of sensor array devices having different attributes that that can be matched to a cell analysis of interest. For example, a sensor array device used for the detection of the electrophysiological activity of a cell can have different attributes than a sensor array device used for the detection of specific analytes for a metabolic study.

Sensor array device attributes that can be varied to provide a variety of sensor array devices of the present teachings include pixel dimensions, as well as the rate at which data can be collected from a sensor array device. FIG. 3 provides an overview of five categories of cells by size in relationship to four exemplary sensor array devices of varying sensor (pixel) dimensions, as given in Table 1 for Device B through Device E. The five categories of cells are identified descriptively, as well as by average diameter and average footprint.

By inspection of FIG. 3, for a very small cell anchored on a sensor array surface with an average diameter of 5 μm and average area of 20 μm², a minimum area of contact or footprint corresponds to about 1 row and about 2 pixels for a Chip 1 device, which increases to 6 rows and 32 pixels for a Chip 4 device. Similarly, for a small cell anchored on a sensor array surface with an average diameter of 10 μm and average area of 78 μm², a minimum area of contact or footprint corresponds to about 3 rows and about 8 pixels for a Chip 1 device, which increases to 12 rows and 126 pixels for a Chip 4 device. For a medium cell anchored on a sensor array surface with an average diameter of 25 μm and average area of 491 μm², a minimum area of contact or footprint corresponds to about 7 rows and about 50 pixels for a Chip 1 device, which increases to 29 rows and 792 pixels for a Chip 4 device. Large cells anchored on a sensor array surface with an average diameter of 50 μm and average area of 1,964 μm², can have a minimum area of contact or footprint corresponding to about 15 rows and about 201 pixels for a Chip 1, which increases to 59 rows and 3,168 pixels for a Chip 4 device. Finally, for an extra large cell anchored on a sensor array surface with an average diameter of 100 μm and average area of 7,854 μm², a minimum area of contact or footprint corresponds to about 30 rows and about 803 pixels for a Chip 1 device, which increases to 118 rows and 12,668 pixels for a Chip 4 device. From inspection of FIG. 3, the trend is towards increasing pixel coverage with increasing cell size and decreasing pixel size.

From a pixel perspective, the column of percent pixel coverage is the percentage of area of a cell that a single pixel covers. For a very small cell anchored on a sensor array surface, a single pixel corresponds to 50% coverage for a Chip 1 device, whereas for a Chip 4 device a single pixel corresponds to 3% coverage. Similarly, for a small cell anchored on a sensor array surface, a single pixel corresponds to 12% coverage for a Chip 1 device, whereas for a Chip 4 device a single pixel corresponds to 0.8% coverage. For a medium cell anchored on a sensor array surface, a single pixel corresponds to 2% coverage for a Chip 1 device, whereas for a Chip 4 device a single pixel corresponds to 0.1% coverage. Large cells anchored on a sensor array surface can have a single pixel corresponding to 0.5% coverage for a Chip 1 device, whereas for a Chip 4 device a single pixel corresponds to 0.03% coverage. Finally, for an extra large cell anchored on a sensor array surface, a single pixel corresponds to 0.1% coverage for a Chip 1 device, whereas for a Chip 4 device a single pixel corresponds to 0.008% coverage. From inspection of FIG. 3, the trend is towards decreasing percentage of cell coverage per pixel with increasing cell size and decreasing pixel size.

Given what is presented in the table of FIG. 3, selection of pixel coverage for exemplary sensor array devices of the present teaching can be made for a variety of average cell diameters. For example, for cells from about 5 μm to about 100 μm, a selection of sensor array devices can be made to provide coverage from about 8 pixels over 3 rows of pixels to about 12,668 pixels over 118 rows of pixels for a corresponding footprint of a cell anchored on a sensor array surface. Over that range of cell sizes, pixel sizes can vary, so that each pixel of a selected sensor array device can cover from between about 12% of a cell to about 0.008% of a cell. Based on the data presented in FIG. 3, it is clear that for any cell size, an exemplary sensor array device can be selected that can provide a substantial number of sensors associated with an area of contact that a cell can occupy on a sensor array device. The spatial resolution that can be provided by various sensor array devices of the present teachings can allow for subcellular discrimination of signals; hence providing for subcellular analysis.

With respect to data collection, for various cell analysis systems of the present teachings, a collection of sensor output signals from all sensors in an array constitutes a frame of data. Given that various sensor array devices of the present teachings can have between about 20 million pixels to about 660 million pixels, a frame of data from various sensor array devices of the present teachings is a data file of substantial size. Additionally, various cell analysis systems of the present teachings include control circuitry coupled to a sensor array device that is configured to generate a substantial number of frames of data from a sensor array device every second. Moreover, there is an inverse relationship between an area of interest selected and the rate at which data can be collected, so that by selecting a smaller subset of pixels to monitor, i.e. by windowing down the area of a sensor array device over which data is collected, frame rate can be increased.

For example, in reference to Table I, a sensor array device with 40 million pixels can collect data at a frame rate of about 120 frames per second (fps). Then, if an area of interest of 20 million pixels is selected, data at a frame rate of about 240 frames per second (fps) can be collected, and for an area of interest of of a single sensor array row is selected, data at a frame rate of about 75,000 frames per second (fps) can be collected. Specifically, with respect to exemplary sensor array devices of the present teachings presented in FIG. 3, the maximum frame rate per row of sensors is provided in the second-to-last column. In the last column, the maximum frame rate that data can be collected for a fractional portion of rows covered by a cell is presented, as derived by a dividing maximum frame rate per row by rows per cell diameter.

As can be seen by inspection of the last column of FIG. 3, a substantial number of frames per second can be collected for targeted areas of interest across a range of cell sizes, providing for data collection comfortably within the kHz range. For a very small cell anchored on a sensor array surface, data can be collected at a maximum frame rate of 75,000 fps for a Chip 1 device, whereas for a Chip 4 data can be collected at a maximum frame rate of 27,000 fps. Similarly, for a small cell anchored on a sensor array surface, data can be collected at a maximum frame rate of 25,000 fps for a Chip 1 device, whereas for a Chip 4 data can be collected at a maximum frame rate of 13,500 fps. For a medium cell anchored on a sensor array surface, data can be collected at a maximum frame rate of 10,714 fps for a Chip 1 device, whereas for a Chip 4 data can be collected at a maximum frame rate of 5,587 fps. Large cells anchored on a sensor array surface can have a maximum frame rate of 5,000 fps for a Chip 1 device, whereas for a Chip 4 data can be collected at a maximum frame rate of 2,746 fps. Finally, for an extra large cell anchored on a sensor array surface data can be collected at a maximum frame rate of 2,500 fps for a Chip 1 device, whereas for a Chip 4 data can be collected at a maximum frame rate of 1,373 fps.

From inspection of FIG. 3, the trend is towards decreasing frame rate with increasing cell size and decreasing pixel size, which is consistent with the inverse relationship between an area of interest selected and the rate at which data can be collected. As such, by selecting a smaller subset of pixels to monitor, i.e. by windowing down the area of a sensor array device over which data is collected, frame rate can be increased. Additionally, in reference to Table 1, a device with a desirable frame rate matched to an application can be selected.

Additional sensor array device attributes that can be varied relate to various types of microwell structures that can be associated with various sensor array devices of the present teachings. Regarding for microwell array 122 positioned over sensor array 120 of FIG. 2A, a microwell array can be fabricated over a sensor array, for which there can be at least one sensor or pixel per microwell. For various embodiments of sensor array devices of the present teachings, there can be more than one sensor or pixel per microwell.

Figure 4A:
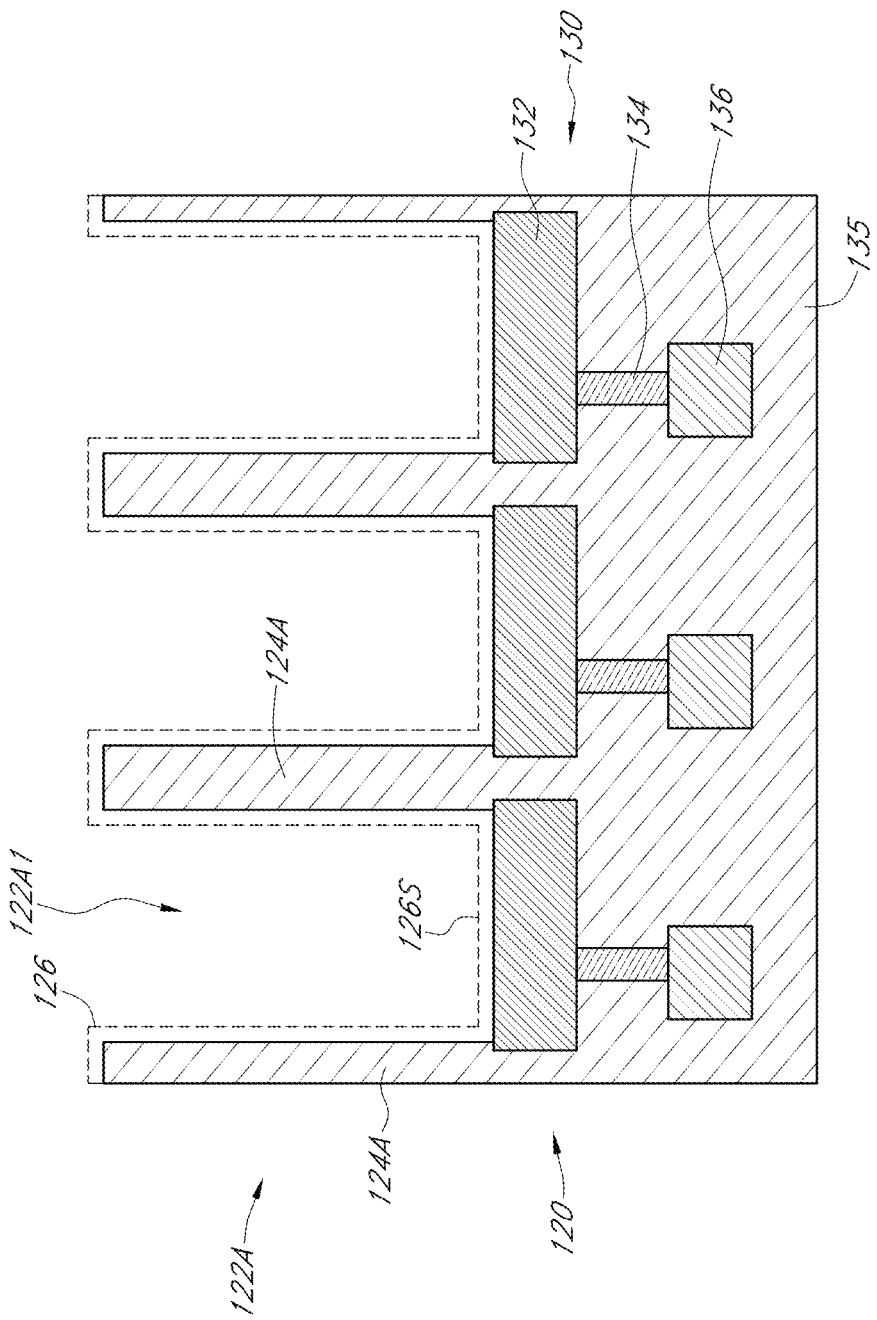
FIG. 4A through FIG. 4C are cross-sectional representations of sensors and associated structures of various designs according to the present teachings.
Figure 4B:
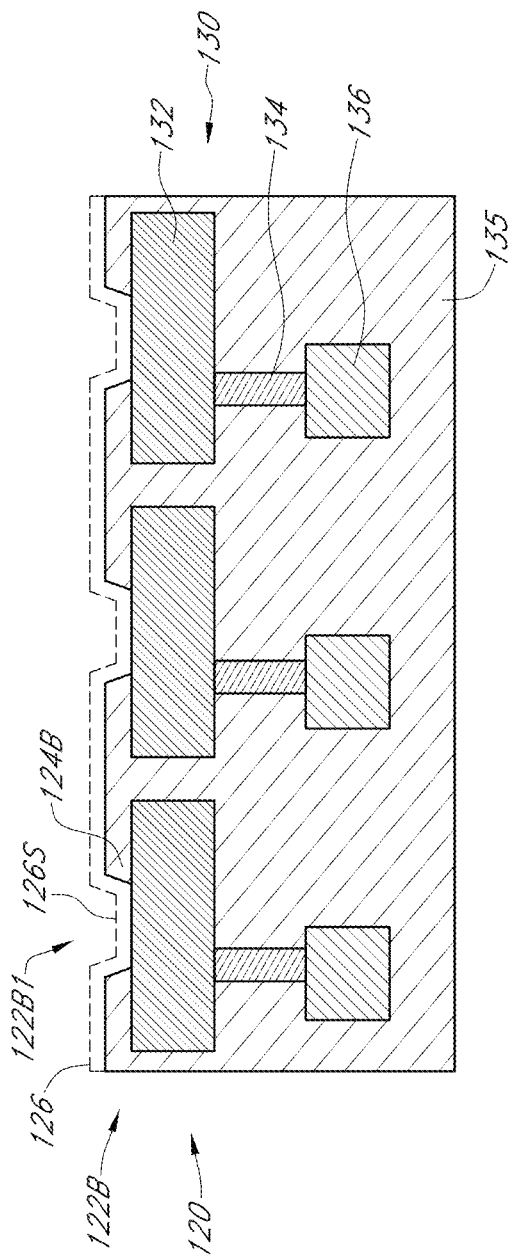
Figure 4C:
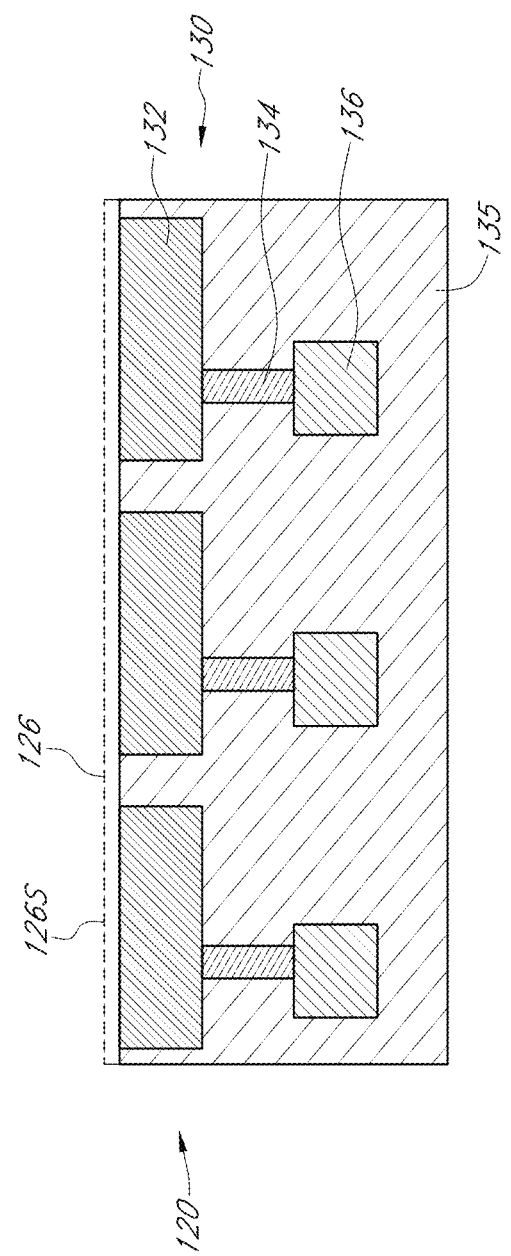

FIG. 4A through FIG. 4C illustrate generally enlarged partial section views of the top portion of a sensor array device, such as sensor array 110 of FIG. 2A. Sensor array 120 of FIG. 4A is a partial section view of an embodiment of a sensor array of the present teachings, upon which microwell array 122A has been fabricated. Exemplary microwell 122A1, illustrative of all microwells of microwell array 122A, can have sidewalls 124A, which are containment structures that can prevent various chemical analytes from diffusing away from the sensor, for example, analytes of interest released by a cell proximal to a sensor. Sensor array 120 of FIG. 4B is a partial section view of an embodiment of a sensor array of the present teachings, upon which microwell array 122B has been formed. Exemplary microwell 122B1 has sidewalls 124B that provide for a microwell array having substantially shallower microwells than for the microwell array 122A of FIG. 4A. FIG. 4C is a partial section view of an embodiment of a sensor array of the present teachings having no microwell array fabricated upon sensor array 120C.

Figure 4D:
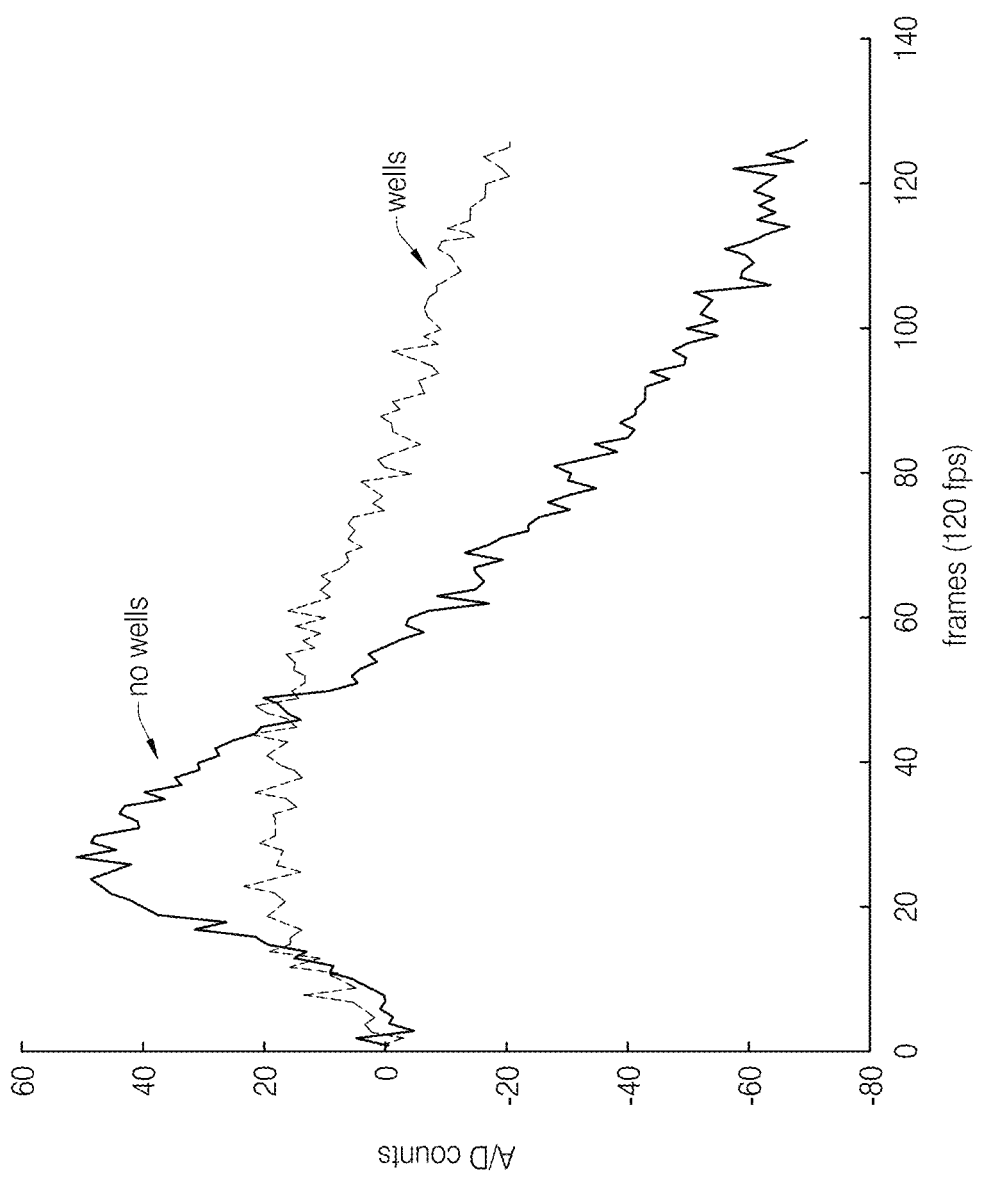
FIG. 4D is a comparison of U-2OS cell response on an array device with wells (as illustrated by FIG. 4A and FIG. 4B) vs. with no wells (as illustrated by FIG. 4C), in which the cells were interrogated under conditions for depolarization of membrane potential, and then return to resting potential.

FIG. 4D is a comparison of U-2OS cell response on an array device with wells (as illustrated by FIG. 4A and FIG. 4B) vs. with no wells (as illustrated by FIG. 4C), in which the cells were interrogated under conditions for depolarization of membrane potential, and then return to resting potential. Given that the measured change of cell potential drops as the square of the distance of a cell from the sensor, the distance can be minimized by using a sensor array with a shallow microwell, such as microwell array 122B of FIG. 4B, or no well at all, such as sensor array 120 of FIG. 4C. The comparison illustrated in FIG. 4D exemplifies an increase in magnitude of response for a device with no wells.

For various types of sensor array devices, the center-to-center spacing between each sensor; or the pitch, can be between about 850 nm to about 3.36 µm, while sensor plate 132 can have a width of between about 600 nm to about 3.1µ. According to the present teachings, the width of a microwell at the bottom of the microwell over a sensor plate cannot be more than about 90% of the width of sensor plate 132. By way of a non-limiting example, for a sensor plate, such as sensor plate 132 of FIG. 4A-FIG. 4C, with a width of about 600 nm, various microwell arrays can have a width of about 540 nm the bottom of the microwell over the sensor plate, while for a sensor plate with a width of 3.1µ, various microwell arrays can have a width of about 2.8µ the bottom of the microwell over the sensor plate. According to the present teachings, for various embodiments of a microwell array, the width to height ratio of a microwell can be between about 1:2 to about 1:4. By way of a non-limiting example, for various microwell arrays that have microwells with a width of about 540 nm, the microwell height can be up to about 1.1µ, while for various microwell arrays that have microwells with a width of about 2.8µ, the microwell height can up to about 5.6µ. By way of an additional non-limiting example, for various microwell arrays that have microwells with a width of about 540 nm, the microwell height can be up to about 2.2µ, while for various microwell arrays that have microwells with a width of about 2.8µ, the microwell height can up to about 11.2µ. While non-limiting examples have been given, various embodiments of a microwell array of the present teachings can have any ratio of width to height of between about 1:2 to about 1:4.

For FIG. 4A through FIG. 4C, a partial section view of an upper portion of a floating gate structure is depicted as floating gate upper portion 130. Various embodiments of sensor arrays incorporating floating gate structures have been described, for example, in U.S. Pat. Nos. 9,128,044 and 9,841,398, both of which are incorporated by reference herein; each in its entirety.

Floating gate upper portion 130 of FIG. 4A through FIG. 4C can include a top metal layer, sensor plate 132, as well as metal via 134 and metal layer 136, all of which are formed in dielectric substrate 135. Passivation layer 126 can be deposited to form a continuous top layer over the surfaces that define each microwell of a microwell array. Sensing surface 126S is a portion of a passivation layer formed over sensor plate 132. Metal layers 132, 134, and 136 can be a suitable metallic material or alloy thereof, for example, titanium, silver, gold, platinum, and tungsten. Dielectric substrate 135 can be a dielectric material, such as silicon dioxide or silicon nitride. Passivation layer 126 can be a metal oxide layer, such as titanium oxide, titanium nitride, and titanium oxynitride. For various embodiments of ChemFET devices, a change in the electric potential at a solid liquid interface formed between a solution in contact with a sensing layer, such as sensing layer 126S of FIG. 4A through FIG. 4C, can cause changes in the voltage on the floating gate. An applied reference voltage, as previously described herein for FIG. 2A, ensures that the voltage of the floating gate exceeds the threshold voltage, providing that small changes in the floating gate voltage result in an output signal for example, for sensors such as sensors 120-1 and 120-2 of sensor array 120 of FIG. 2B.

Various modifications can be made to the composition of a sensing surface to provide selectivity for a variety of analytes of interest, for example, analytes of interest for various cell metabolic and trophic studies. For example, detection of various ions can be accomplished through the use of the passivation layer itself or through the use of an ionophore coated onto the passivation layer. For example, hydrogen ion can be detected without modification of a sensing layer, such as sensing layer 126S of FIG. 4A through FIG. 4C, which can be titanium oxide, titanium nitride, or titanium oxynitride. Potassium ion can be detected selectively by coating a sensing layer with, for example, valinomycin, or salinomycin. Sodium ion can be detected selectively by coating a sensing layer with, for example, monensin, nystatin, or with the synthetic ionophore, SQI-Pr (CAS #1022595-16-9). Calcium can be detected selectively by coating a sensing layer with, for example, ionomycin, calcimycine, or ETH 1001 (CAS #58801-34-6). Additionally, for a variety of analyses, selectivity of an ionophore may not need to be for a single species, but moreover able to bind more than one species of ion in a genus of ions. For example, by coating a sensing layer with beauvericin, calcium and barium ions can be detected, while by coating a sensing layer with nigericin, potassium, hydrogen and lead ions can be detected. Gramicidin can be coated on a sensing layer to detect hydrogen, sodium and potassium ions. According to the present teachings, various ionophores having selectivity for a genus of ions can be used in applications in which single ion specificity is not required or in which it is unlikely that other ions which the compounds bind will be present or generated. Additionally, various classes of photocurable polymers can provide selectivity for a wide variety of analytes of interest for cell biology studies including a range of ions, such as potassium, calcium, ammonium, chloride, and nitrate, as well as for glucose, sucrose and urea (see for example, *Sensors* 2009, 9, 7097-7100).

In addition to providing detection selectivity for various analytes by varying the composition of sensing surface portion of a passivation layer in contact with a sensor plate, the passivation layer can be treated with a material to provide cell compatibility, as depicted in FIG. 2B. Additionally, a sensor surface of a sensor array device with a microwell array positioned over sensor array, such as depicted in FIG. 2A, can be treated by coating a cell-compatible material on the sensor array surface including the microwell array. For coating various embodiments of a sensor array device of the present teachings, an end-user can select a specific material from a variety of cell-compatible materials that may be best suited to a cell line of interest and set of experiments, and can coat a sensor array surface with a cell-compatible material before preparing a sensor array with a sample of cells. Exemplary cell-compatible materials that can be coated on a sensor device surface include various biopolymer materials such as poly-D-lysine, laminin, fibronectin, collagen, and combinations thereof, as well as various preparations of extracellular matrix (ECM).

Providing a cell-compatible coating over a sensor array can provide an interface on which various types of cells can anchor on a sensor array surface, as depicted in FIG. 2A and FIG. 2B. Once the cells are stably anchored, by providing a continually-refreshed nutrient solution, for example by flowing nutrient solution through a flow cell, the cells can grow and divide.

Accordingly, various sensor array devices of the present teachings can have several attributes that can provide variety of sensor array devices that can be selected for a targeted cell analysis. Such attributes can include the presence or absence of a microwell array fabricated over a sensor array, the depth of each microwell in a microwell array for sensor array devices including a microwell array, the nature of a surface treatment of a sensing surface to provide selectivity for chemical analysis, the type of surface treatment of a sensor array device to provide a cell-compatible coating, pixel pitch and size, and the rate at which data can be collected. By way of a non-limiting example, various sensor array devices of the present teachings can have a microwell array disposed over a sensor array, or have no microwell array disposed over a sensor array. Various sensor array devices of the present teachings can have sensing surfaces that provide selectivity for various chemical analytes of interest in cell analysis. Such sensor array devices can be used, for example, in various cell metabolism and electrophysiological studies and can provide for monitoring various spontaneous and temporal cell activities.

Chemical Field Effect Transistor (ChemFET) Array-Based Systems for Cell Analysis As previously described herein, FIG. 1 illustrates generally a block diagram of exemplary components of cell analysis system 100 according to the present teachings. As depicted in FIG. 1, cell analysis system 100 can include various fluidic systems, as well as array controller 50, user interface 60, and sensor array device assembly 115.

Regarding fluidic delivery and control for performing various cell analyses on sensor array device 110, cell analysis system 100 can include reagent fluidic system 10, wash solution fluidic system 20, fluidic multiplexer system 30, and valve controller 40. Additionally, flow cell 107 is an integral part of the fluidics system of cell analysis system 100, as flow cell 107 can define a flow path for various reagents and wash solutions over sensor array device 110. Reagent fluidic system 10 according to the present teachings, can include a plurality of reagent containers, such as, reagent containers 11A-11N, that can be placed in controllable fluid communication with sensor array device 110 via flow cell inlet line 103A. Reagent fluidic system 10 can include a reagent fluid line for each reagent container, such as reagent fluid lines 13A-13N, which correspond to reagent containers 11A-11N, respectively. Additionally, each fluidic reagent line can have fluid flow controlled by a valve, such as reagent fluid line valves 15A-15N, depicted in FIG. 1 as inline valves for each of reagent fluid lines 13A-13N, respectively. Wash solution fluidic system 20 can include wash solution wash solution container 21, which can be placed in controllable fluid communication with flow cell inlet line 103A via wash solution fluid line valve 25. Fluidic multiplexer system 30 can include fluidic multiplexer system waste container 31, which is in fluid communication with fluidic multiplexer 35 via fluidic multiplexer fluid line 33.

As depicted in FIG. 1, reagent fluid line valves 15A-15N can be controlled by valve controller 40. In that regard, valve controller 40 can control the fluid flow from each reagent container 11A-11N to fluidic multiplexer 35. Additionally, as depicted in FIG. 1, valve controller 40 can control the fluid flow from wash solution container 21 of wash solution fluid system 20 through control of wash solution fluid line valve 25, which is depicted in FIG. 1 as inline wash solution fluid line valve 25 on wash solution fluid line 23. As indicated in FIG. 1 by the control line from valve controller 40 to each reagent container 11A-11N, valve controller 40 can also actuate control of pneumatic valves on pneumatic lines from an inert gas source (not shown) that provide a controllable pressure head for each reagent container 11A-11N, as well as for wash solution container 21. Accordingly, fluids from various reagent and wash solution containers of cell analysis system 100 can be controllably moved through fluidic lines using a pressure difference from source to outlet as a motive force.

In conjunction with control provided by valve controller 40, fluidic multiplexer 35 of FIG. 1 can controllably perform fluidic operations that include, for example, but not limited by, providing selected reagent delivery to sensor array device 110, washing of fluidic multiplexer 35 and flow cell 107, and priming of fluidic multiplexer 35 with a selected reagent. Such fluidic operations can provide for cross contamination-free delivery of reagents to flow cell 107, can provide for sharp transitions between reagent fluid streams, as well as providing a constant electrolyte fluidic environment for reference electrode 27 in wash solution fluid line 23, thereby providing a constant stable reference voltage to sensor array device 110. The function of various embodiments of fluidic multiplexer 35 for directing flow in various embodiments of fluidics systems for sensor array systems has been described in US Patent Publication 2010/0137143, U.S. Pat. Nos. 8,546,128, and 8,673,627 all of which are incorporated by reference herein; each in its entirety.

For example, in conjunction with valve controller 40, fluidic multiplexer 35 of FIG. 1 can selectively provide fluid communication between any of reagent fluid lines 13A-13N and flow cell inlet line 103A, thereby providing selective reagent flow through flow cell 107 of sensor array device assembly 115. A non-limiting illustrative reagent solution fluidic path of the present teachings is given by a reagent delivery operation in which wash solution fluid line valve 25 is in a closed state, and one of reagent fluid line valves 15A-15N is in an open state, providing that one of a selected reagent is in fluid communication with fluidic multiplexer 35. Under such a condition, a selected reagent can flow through fluidic multiplexer 35 and then through fluidic multiplexer fluid line 33 to fluidic multiplexer waste container 31. Additionally, a selected reagent can flow through fluidic multiplexer 35 to flow cell inlet line 103A, where it can then flow through flow cell 107 from inlet port 102 to outlet port 104, and finally through flow cell outlet line 103B to flow cell waste container 101.

With respect to fluidic control of a wash solution, in conjunction with valve controller 40, fluidic multiplexer 35 of FIG. 1 can selectively provide fluid communication between wash solution container 21 and flow cell inlet line 103A. As such, with wash solution fluid line valve 25 in an open state, solution container 21 can be in fluid communication with fluidic multiplexer waste container 31, as well as with flow cell waste container 101, providing that washing of fluidic multiplexer 35 and flow cell 107 can be done. A non-limiting illustrative wash solution fluidic path of the present teachings is given by a washing operation in which wash solution fluid line valve 25 is in an open state, and each of reagent fluid line valves 15A-15N is in a closed state, providing that a wash solution can flow through wash solution fluid line 23 to a T-junction with flow cell inlet line 103A. As flow cell inlet line 103A is in fluid communication with fluidic multiplexer 35, wash solution can flow to fluidic multiplexer waste container 31 through fluidic multiplexer fluid line 33. As flow cell inlet line 103A is additionally in fluid communication with sensor array device assembly 115, wash solution can through flow cell 107 from inlet port 102 to outlet port 104, and then can flow through flow cell outlet line 103B to flow cell waste container 101.

According to the present teachings, priming of fluidic multiplexer 35 with a selected reagent can be done, for example, in sequence after a washing operation and before the selected reagent is placed in fluid communication with flow cell 107 of FIG. 1. A non-limiting illustrative reagent priming fluidic path of the present teachings is given by a reagent priming operation in which wash solution fluid line valve 25 is in an open state, and one of reagent fluid line valves 15A-15N is in an open state, providing that one of a selected reagent is in fluid communication with fluidic multiplexer 35. Under such an operation, the flow rate of the wash solution relative to the flow rate of the reagent is selected so that wash solution flows through fluidic multiplexer 35 to fluidic multiplexer waste container 31 through fluidic multiplexer fluid line 33, except for the passage in fluidic multiplexer 35 in fluid communication with the selected reagent fluid, such as one of reagent fluid lines 13A-13N. Accordingly, when a reagent delivery operation as previously described herein is initiated, the reagent selected in the reagent priming operation is in direct flow communication with flow cell inlet line 103A.

As such, various embodiments of fluidic systems of the present teachings are configured to execute a sequence of operations that can include washing, priming and reagent delivery. Such operations executed in a sequence can avoid cross-contamination of reagents in system fluid lines and compartments, provide sharp transitions between reagent fluid streams, and provide a constant electrolyte fluidic environment for a reference electrode, thereby providing a constant stable reference voltage to a sensor array.

According to the present teachings, sources of noise arising from fluid lines can affect the reference voltage, for example, a reference voltage that is provided by reference electrode 27, which is positioned in wash solution fluid line 23 of FIG. 1. As previously described herein, a stable reference voltage from reference electrode 27 for sensor array device 110 of FIG. 1 can be provided by having a fluidic system that ensures that reference electrode 27 is in continuous contact with a wash solution of know electrolyte composition. Additionally, high frequency noise from fluid lines, for example, reagent fluid lines 13A-13N and fluidic multiplexer fluid line 33, can be filtered by capacitively coupling electrodes positioned in the fluid lines to the reference electrode. According to the present teachings, electrodes can be hollow cylindrical structures, for example, of an inert metal, non-limiting examples of which include platinum or titanium. Such hollow cylindrical metal structures, can provide effective ohmic contact with a fluid in a flow stream. As depicted in FIG. 1, reagent fluid line electrodes 17A-17N, which are positioned in reagent fluid lines 13A-13N, respectively, are coupled to reference electrode 27 through separate reagent fluid line capacitors 19A-19N, each of which is coupled to reagent fluid line electrodes 17A-17N, respectively. In a similar fashion, fluidic multiplexer fluid line electrode 37, which is positioned in fluidic multiplexer fluid line 33, is coupled to reference electrode 27 through fluidic multiplexer fluid line capacitor 39.

As depicted in FIG. 1, cell analysis system 100 can additionally include array controller 50 and user interface 60. According to the present teachings, array controller 50 can provide various power supplies and bias voltages, as well as control and timing signals to sensor array device 110, and additionally a data and processor interface for high-speed acquisition of data from sensor array device 110. In that regard, FIG. 5A and FIG. 5B depict various functions of array controller 50 in relationship to various functions of sensor array device 110 of the present teachings.

Figure 5A:
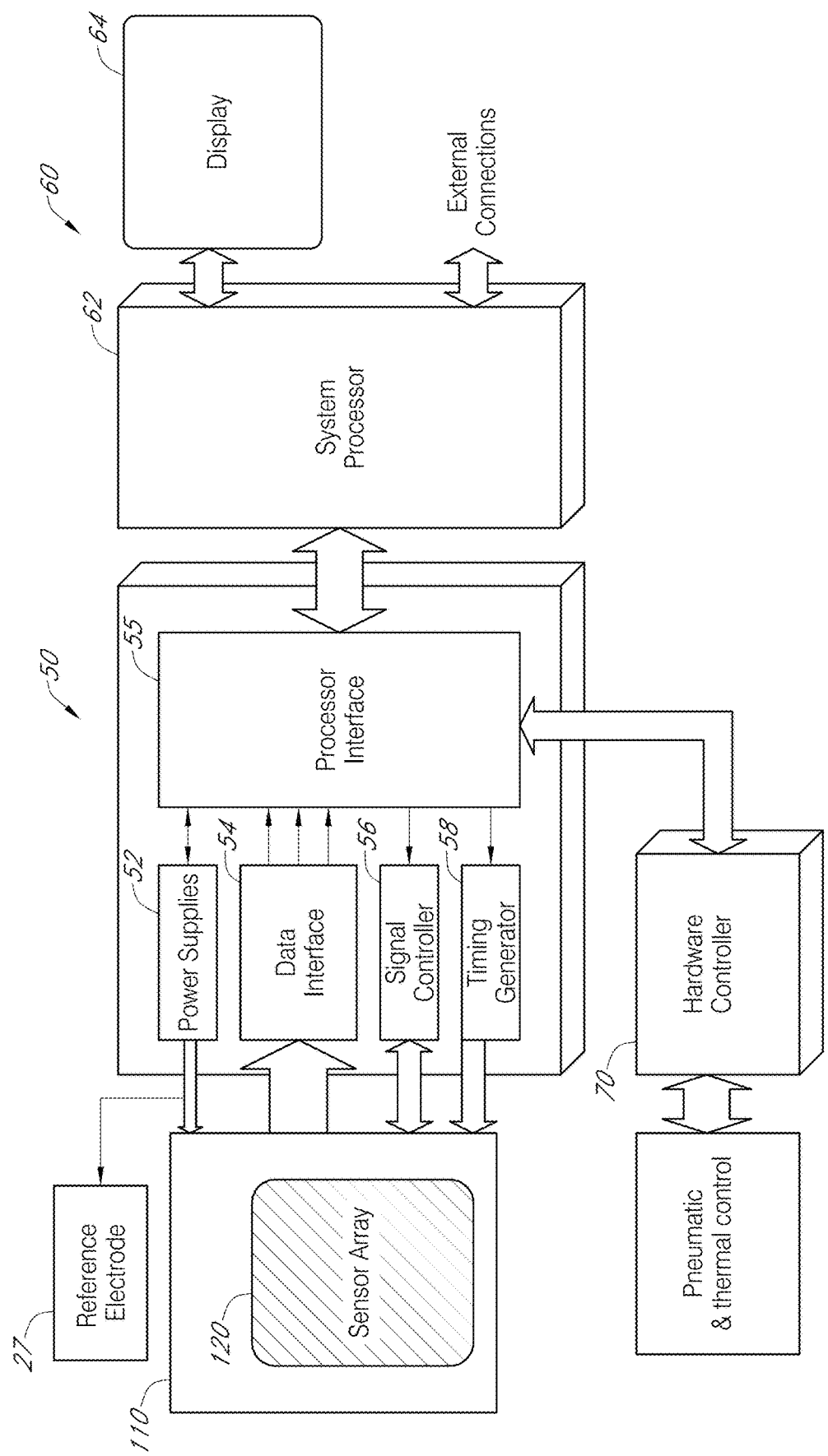
FIG. 5A is a block diagram depicting various embodiments of a sensor array, array controller and computer interface of a ChemFET-based cell analysis system according to various embodiments of systems and methods of the present teachings.
Figure 5B:
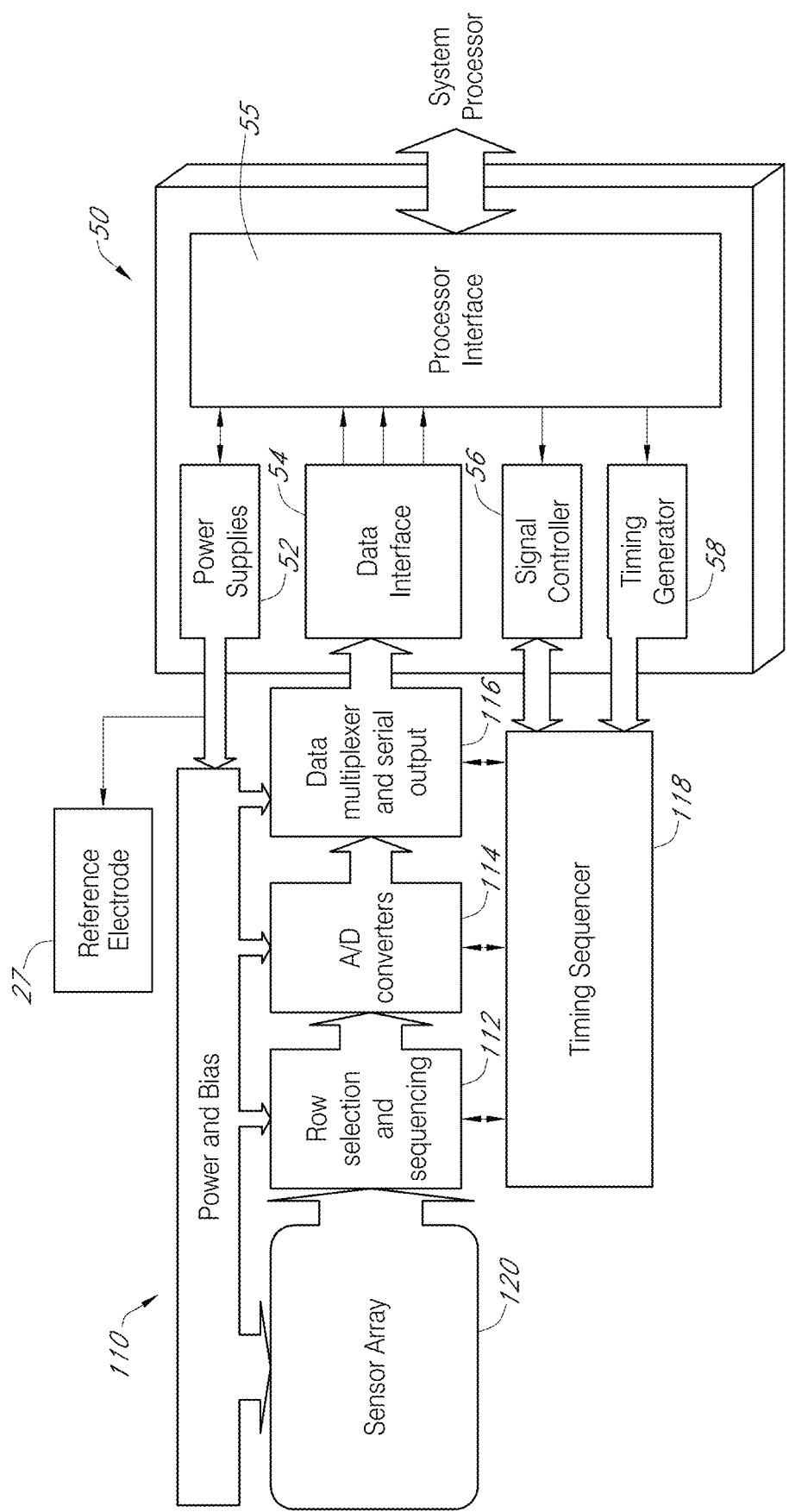
FIG. 5B is a block diagram depicting various embodiments of a sensor array and an array controller of a ChemFET-based cell analysis system according to various embodiments of systems and methods of the present teachings.

FIG. 5A illustrates generally various aspects of the function between array controller 50 in relationship to sensor array 120 of sensor array device 110, as well as between array controller 50 and to user interface 60. According to various embodiments of a cell analysis system of the present teachings, array controller 50 can have multiple power supplies 52, for providing power to sensor array device 110, as well as supporting digital interface 54, which is a high-speed digital interface configured to read the data generated by sensor array device 110. Additionally, array controller 50 is configured to provide signals to sensor array device 110, such as control signals from signal controller 56, as well as timing signals from timing generator 58. Multiple power supplies can be provided to sensor array device 110, including analog supply, digital supply, I/O supply, and ground. In one exemplary implementation, each of the supply voltages can be controllable in the range of 1.2 to 3.3V. Each of these power supply voltages can be provided to sensor array device 110 via separate conducting paths to facilitate noise isolation. These supply voltages can originate from a respective power supply, or one or more of these supply voltages can originate from a common source in array controller 50. According to various embodiments of an array controller of the present teachings, the power supply can include one or more digital-to-analog converters (DACs) that can be controlled by system processor 62 to allow any or all of the supply voltages to be changed under software control. For example, a power supply responsive to computer control can facilitate switching between a supply voltage of 1.6 Volts and a supply voltage of 1.8 Volts depending the requirement for the type of sensor array device in use, as read from data stored on various embodiments of a sensor array device.

Hardware controller 70 illustrated in FIG. 5A can be implemented as one or more separate circuit boards, or as part of the interface board. One function of hardware controller 70 is to provide pneumatic and fluidic control, for example, to control the timing and duration of the various fluids and reagents that flow over the sensing surface of each sensor in sensor array 120, as well as to read pressure and flow sensors related to pneumatic and fluidic flow control, as determined by system processor 62 software. Additionally, hardware controller 70 can support temperature measurement and control for sensor array device 110, as well as temperature measurement and control for assemblies and subassemblies of the system. According to the present teachings, temperature measurements can be done, by way of a non-limiting example, using thermistors and thermocouples. In response to temperature measurements, system processor 62 can control devices that can include non-limiting example such as fans, heaters, and thermo-electric coolers.

Array controller 50 can be fabricated as a "stand alone" circuit board, or as one or more computer compatible "cards" forming part of a computer. In one aspect, the functions of an array controller of the present teachings can be controlled by system processor 62 through processor interface 55 (e.g., PCI bus, Ethernet connection, etc.). In one embodiment, all or a portion of the array controller is fabricated as one or more printed circuit boards, and the sensor array device is configured to attach to one of the printed circuit boards. External connections to system processor 62 can include standard computer interfaces, such as Ethernet and USB. Finally, system processor 62 can include display 64.

As depicted in FIG. 5B, various power supplies and bias voltages are provided to sensor array device from array controller 50. Sensor array device 110 of FIG. 5B can incorporate one or more analog-to-digital converters (ADCs) 114 and one or more data multiplexer and high-speed serial output 116 to convert the analog output signals of sensor array 120 to high-speed serial data interface 54, thereby providing digital data to system processor 62 (see FIG. 5A) from sensor array device 110 via processor interface 55. For various embodiments of sensor array device 110, analog-to-digital converters (ADCs) 114 can have a computer-selectable input range (e.g., 200 mV, 300 mV) to facilitate compatibility with different ranges of sensor output signals.

According to the present teachings, for various embodiments of sensor array device 110 FIG. 5B, array row selection and sequencing 112, ADCs 114 and data multiplexer and high speed serial output 116 can be controlled by logic on timing sequencer 118 of sensor array device 110 with timing provided by array controller 50. In one exemplary implementation, the number of rows from which data is acquired, and the sampling rate of acquisition can be controlled based on control data provided to sensor array device 110 from array controller 50. In one non-limiting example, timing generator 58 can be implemented as a programmable clock generator integrated circuit that is controlled by system processor 62 in order to allow for the control of different sensor array device types, operating modes, and acquisition data rates. The control signals between array controller 50 and sensor array device timing sequencer 118 can be exchanged using a standard serial interface type, such as I2C or SPI. Information written to sensor array device 110 can include values stored or written to on-device registers to sensor array device timing sequencer 118 to control sensor array device 110 operating modes, as well as to read data from the sensor array device 110. Information read from sensor array device 110 can include stored data including chip type, serial number, manufacture date, etc.

Reference electrode 27 of FIG. 5B can be coupled to a power supply to provide a reference potential for the output voltages (output signals) from each sensor of sensor array 120. By way of a non-limiting example, the reference electrode voltage of reference electrode 27 can be set by flowing a solution with a known and stable pH over sensor array device 110 (see FIG. 2A). Under such a defined pH condition, the reference electrode voltage can be adjusted until the output signals for sensors in a sensor array, for example sensors of sensor array 120 of FIG. 2A, indicate that the sensors have voltages at a desired reference level. Once the reference voltage is set using a solution with a known and stable pH, a subsequent change in a sensor voltage can reflect that a local change in pH has occurred at a sensing surface of a sensor of a sensor array.

Figure 6A:
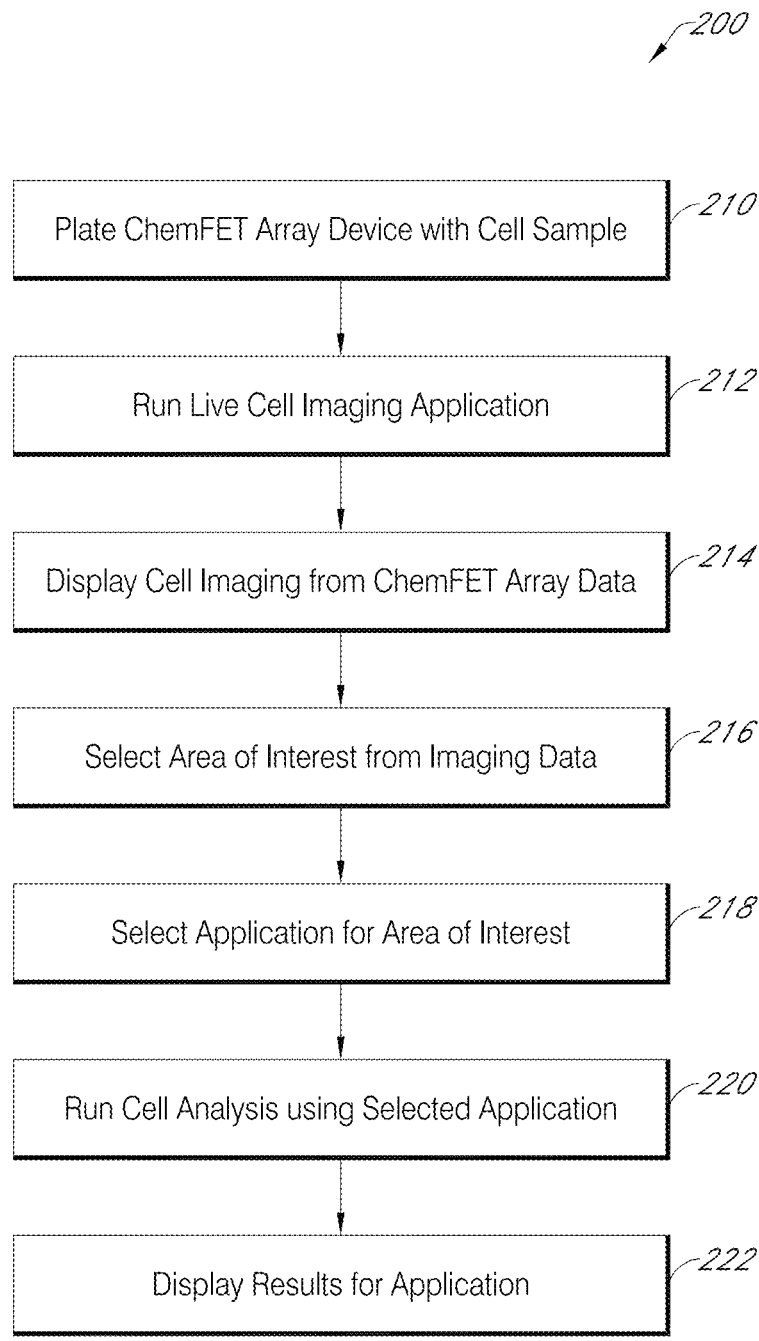
FIG. 6A and FIG. 6B are flow diagrams depicting work flow related to cell analysis according to various embodiments of systems and methods of the present teachings.

Applications and Methods Using ChemFET Sensor Array-Based Systems for Cell Analysis Flow diagram 200 of FIG. 6A presents work flow related to embodiments of applications and methods of the present teachings that can be run using a cell analysis system and related devices, components and assemblies of the present teachings. For example, flow diagram 200 can be run using cell analysis system 100 of FIG. 1, which can include a sensor array device interfaced to an array controller and system processor, such as sensor array device 110, array controller 50 and user interface 60 of FIG. 1, FIG. 5A and FIG. 5B.

Flow diagram 200 of FIG. 6A can be initiated with step 210; plating a ChemFET sensor array device with a cell sample. A suspension of cells at a known density can be flushed or otherwise drawn into a sensor array device assembly, such as sensor array device assembly of FIG. 1. Following plating of a cell sample, the sensor array device assembly can be covered and placed in incubation for a targeted period of time to allow the cells to settle and anchor on a sensor array surface. Before plating the sensor array device assembly with a cell sample, flow diagram 200 can additionally include a step of preparation of a sensor array surface with a user selected cell-compatible material, such as various biopolymer materials including poly-D-lysine, laminin, fibronectin, collagen, and combinations thereof, as well as various preparations of extracellular matrix (ECM). The preparation of a sensor array surface with a cell-compatible material can done in advance of plating, and the sensor array devices can be stored for future us. Alternatively, in situ preparation of a sensor array surface with a cell-compatible material can be done prior to plating the sensor array device assembly with a cell sample.

After cells have been stably associated with a sensor array surface, at step 212 of flow diagram 200, a live cell imaging application can be performed, and at step 214, the results can be displayed. The information at step 214 from the live cell imaging application can provide an end user with a general survey of cell distribution on a sensor surface, with information regarding individual cell morphology and with an assessment of individual cell viability. For example, cell analysis system 100 of FIG. 1 can provide an end user with electroscopic cell imaging. For such an imaging application, any change in the state of a cell anchored on the surface of a sensor array device that can cause a change in potential of a sensing surface of a ChemFET sensor can be detected by each sensor in a sensor array responsive to cell activity cell. An electroscopic image of responsive cells at a selected time during, for example, a live cell imaging application can be presented to an end user, for example, on a display, such as display 64 of user interface 60 of FIG. 5A. As previously described herein, given that electroscopic imaging is predicated on a variety of responses that can be elicited for living cells, obtaining an electroscopic image of responsive cells on a sensor array surface can be useful as an initial step for the visualization and assessment of cells. As an alternative to or in addition to electroscopic imaging, other methods of visualizing cells can be used, such as optical microcopy.

At step 216 of flow diagram 200, based on the information provided from live cell image display step 214, an area of interest can be selected based on, for example, identifying an optimal area regarding distribution and activity of cells and in consideration of the application of interest. As previously described herein, as there is an inverse relationship between the rate at which data can be collected, and the selection of area of interest. For example, to monitor action potential of various excitable cells may require data acquisition rates in the sub-millisecond to millisecond range, while to monitor lactate production from oxidative phosphorylation may require data acquisition rates of seconds to minutes. At step 218, an end user can select an application from, for example, a menu presented on a graphical user interface (GUI) and then initiate a run, as given in step 220. Finally, at step 222, an end user can receive the results of an experiment, for example, but not limited by, as provided on a display, such as display 64 of user interface 60 of FIG. 5A, as provided by sending as a report to the system processor, such as system processor 62 of user interface 60 of FIG. 5A, or both.

Figure 6B:
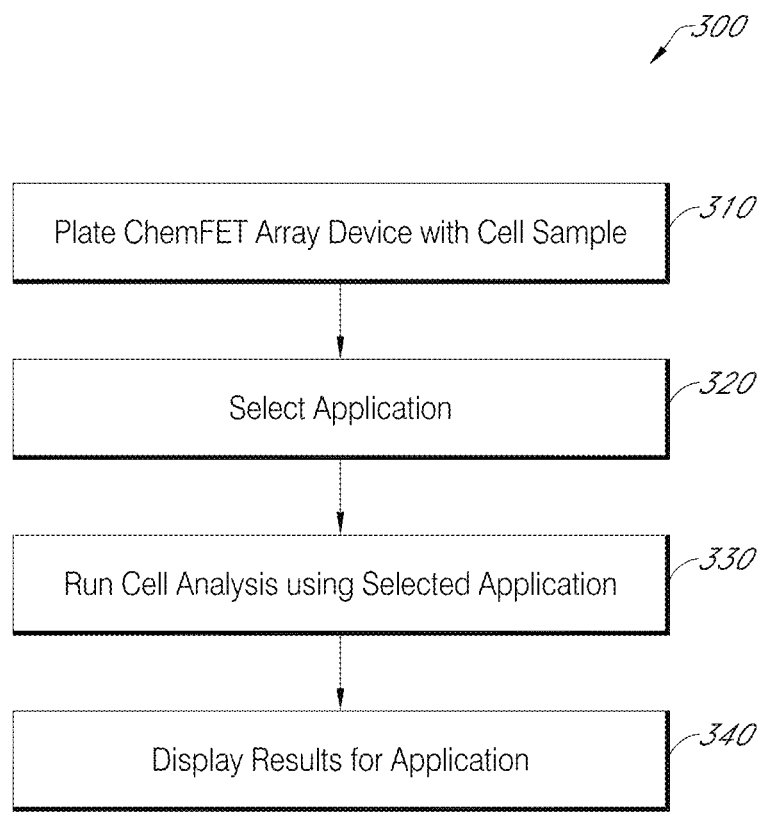

Alternatively, an end user can run an application without first running a live cell imaging application to select an area of interest. Flow diagram 300 of FIG. 6B can be initiated with step 310; plating a ChemFET sensor array device with a cell sample, as previously described for step 210 of FIG. 6A. According to the present teachings, plating of the cells can be done on a sensor array device treated with a cell-compatible material. At step 320, an end user can select an application from, for example, a menu presented on a graphical user interface (GUI) and then initiate a run, as given in step 330. Finally, at step 340, an end user can receive the results of an experiment, for example, but not limited by, as provided on a display, such as display 64 of user interface 60 of FIG. 5A, as provided by sending as a report to the system processor, such as system processor 62 of user interface 60 of FIG. 5A, or both. When an application is run without selecting an area of interest, data is collected at a frame rate associated with a sensor array device, for example, as shown in Table I. Though an end-user can zoom in and expand any area on a device, for example, of an electroscopic image, the resolution of the finally-presented data is fixed by the frame rate associated with the device.

Various methods of in situ treatment of a sensor array device to provide a coating of a cell-compatible material on a sensor array surface are applicable for various sensor array devices of the present teachings, for example, as presented in the table of FIG. 3. With respect to exemplary methods for in situ modification of a sensor array surface with a cell-compatible material, the following solutions of exemplary cell-compatible materials were used to coat the surfaces of three ISFET sensors selective for sensing hydrogen ion (pH):

1. 0.1% poly-D-lysine (PDL) in phosphate buffered saline (PBS)
2. 0.1% poly-D-lysine (PDL)+0.05% laminin in PBS
3. A commercial formulation of extracellular matrix (ECM), Geltrex®, used without dilution The three sensor array devices, which were of the type identified as Chip 1 in the table of FIG. 3, were opened in a sterile, laminar flow cell culture hood and all manipulations thereafter were performed under sterile conditions with sterilized solutions and materials. Each sensor array device was flushed twice with 200 µL of a solution composed from 70% ethanol in water that was injected with pipette into one of the solution ports and gently aspirated from the other. Once solutions were applied to the chip surface, care was taken not to let the surface or chamber beneath the flow cell be aspirated to dryness or run dry, so a vacuum line was positioned just above the exit port opposite the port used for solution injection and the chip was never vacuumed dry. The 70% ethanol solution was allowed to stay on the sensor array devices for 30 minutes at room temperature, and was then flushed repeatedly with 200 µL of cell culture grade PBS. Sensor array devices were then flushed with 200 µL of the solutions as described above, and allowed to sit at room temperature for one hour before being flushed three times with 200 µL of fresh PBS, after which, they are ready for use. Alternatively, sensor array devices prepared to provide cell-compatible surfaces as described can be sealed and stored for later use.

To verify sensor array function for sensor array devices treated as described above to provide cell-compatible sensor surfaces, a cell analysis system, such as cell analysis system 100 of FIG. 1, was used to evaluate the treated sensor array devices. The wash solution container and three reagent containers were filled with the following solutions of the following compositions:
1. The wash solution container and first reagent container were filled with a solution having the following composition and properties:
   20 mM HEPES, pH 7.4
   140 mM NaCl
   2.5 mM KCl
   1.8 mM $CaCl_2$
   1.0 mM $MgCl_2$
   Osmolarity: 300 mOsm
2. The second reagent container was filled with a solution having the following composition and properties:
   20 mM HEPES, pH 7.6
   140 mM KCl
   2.5 mM NaCl
   1.8 mM $CaCl_2$
   1.0 mM $MgCl_2$
   Osmolarity: 300 mOsm
3. The third reagent container was filled with a solution having the composition and properties of the solution used to fill the second reagent container, but adjusted to a pH 0f 7.1 using a dilute solution of hydrochloric acid.

Each sensor array device and a control with an untreated surface were subjected to a test protocol as follows:
1. The wash buffer solution and was used to set the reference electrode potential, as well as to adjust the sensor array device.
2. For each sensor device, two pixels in different sensor regions were selected to measure potentials during testing.
3. The order that the solutions were drawn through the flow cell of each device was as follows:
   a. Switch from the wash solution to the solution in the first reagent container in order to verify that they was no large effect in switching between the same solution in different containers.
   b. Switch back to the wash solution followed by switching to the second reagent container solution in order to measure effect of the change in pH from 7.4 to 7.6.
   c. Switch back to the wash solution followed by switching to the third reagent container solution in order to measure effect of the change in pH from 7.4 to 7.1.

Figure 17:
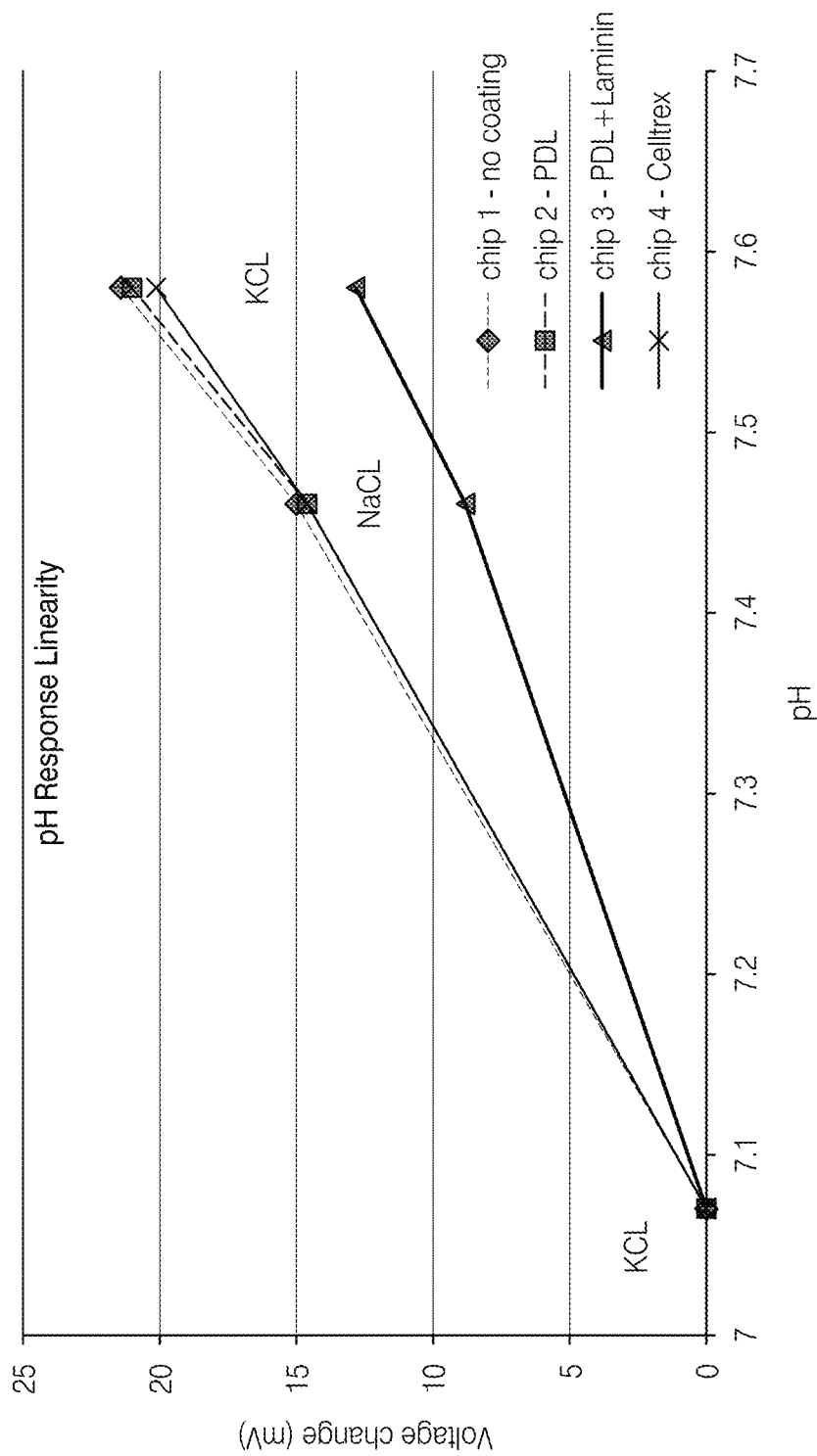
FIG. 17 is a graph of the pH responses for ChemFET devices treated to provide cell-compatible sensor surfaces.

The data generated from the test protocol verified that the sensor array devices treated to provide cell-compatible surfaces had responses that indicated that there was no adverse effect on sensor array device performance due to the coating of the devices. A graph of the pH responses for the devices is presented in FIG. 17.

FIG. 7A through FIG. 8B present data relating to the measurement of the change in cell membrane potential over a time course of induced depolarization followed by a recovery phase. The sensor array device used in this study was a Chip 1 device as shown in the table of FIG. 3 selective for sensing hydrogen ion, and included a microwell array. The device was treated to provide a cell-compatible poly-D-lysine coating as previously described herein. U-2OS cells (ATCC catalogue number ATCC-HB-96), which are a human osteosarcoma cell line commonly used for heterologous expression studies, were transduced with green florescent protein (GFP) to provide for monitoring of the cells on the sensor array surface using florescence microscopy, as well as being transduced with ion channel constructs to provide for response to a depolarizing stimulus. The U-2OS were prepared for plating using standard dissociation procedures, pelleted using centrifugation at 200×g and resuspended in complete cell culture medium at a density of 250,000 cells per milliliter. 200 µL of cell suspension was then drawn through the sensor array device. The sensor array device was then placed into a sterile 10 cm cell culture dish and covered. Sensor array devices prepared in this manner are then transferred to an incubator and incubated at 37° C. at least overnight in advance of use in a cell analysis system of the present teachings.

Figure 7A:
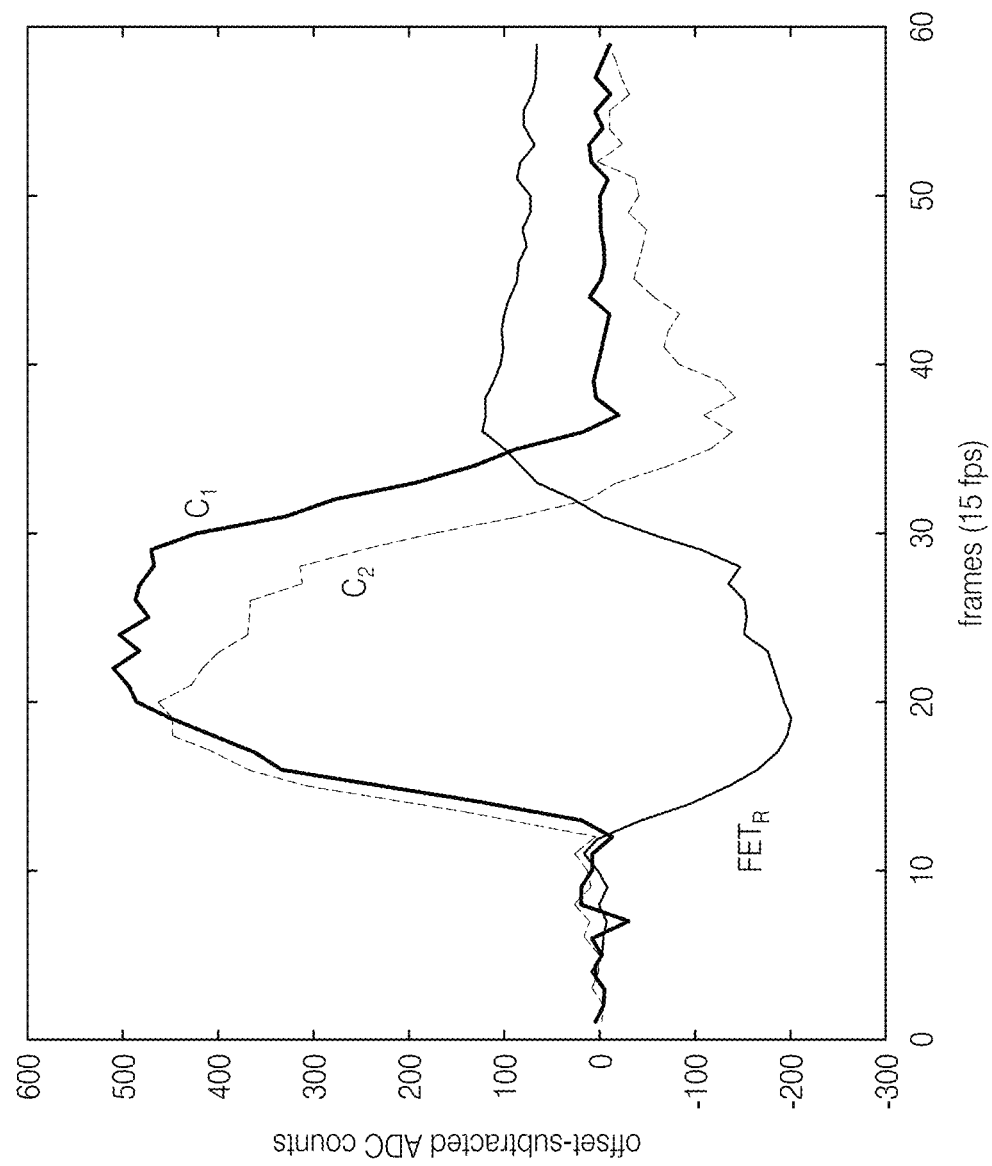
FIG. 7A and FIG. 7B are temporal response curves for cells having membranes at resting potential, then interrogated under conditions for depolarization of membrane potential, and return to resting potential.

The graph presented in FIG. 7A is a temporal response curve that represents data collected over an area of interest that focused on the activity of two cells, $C_1$ and $C_2$ during the course of a cell imaging study. Two solutions were used for the cell imaging study presented in FIG. 7A through FIG. 8B:
1. The wash solution container and first reagent container were filled with a solution having the following composition and properties:
   20 mM HEPES, pH 7.3
   140 mM NaCl
   2.5 mM KCl
   1.8 mM $CaCl_2$
   1.0 mM $MgCl_2$
   Osmolarity: 300 mOsm
2. The remaining reagent containers; containers two through 4, were filled with a solution having the following composition and properties:
   20 mM HEPES, pH 7.3
   140 mM KCl
   2.5 mM NaCl
   1.8 mM $CaCl_2$
   1.0 mM $MgCl_2$
   Osmolarity: 300 mOsm The solution in the flow cell for the initial condition before initiating the cell imaging study was the wash solution. The study was initiated when the solution in one of reagent containers two through four were drawn through the flow cell and over the sensor array. As the cation of predominant concentration in that solution is potassium, it is a solution that can provide a depolarizing stimulus for the cells. In addition to monitoring the activity of the cells, a reference response $FET_R$, was monitored in an area of the sensor array where no cells are anchored.

Figure 7B:
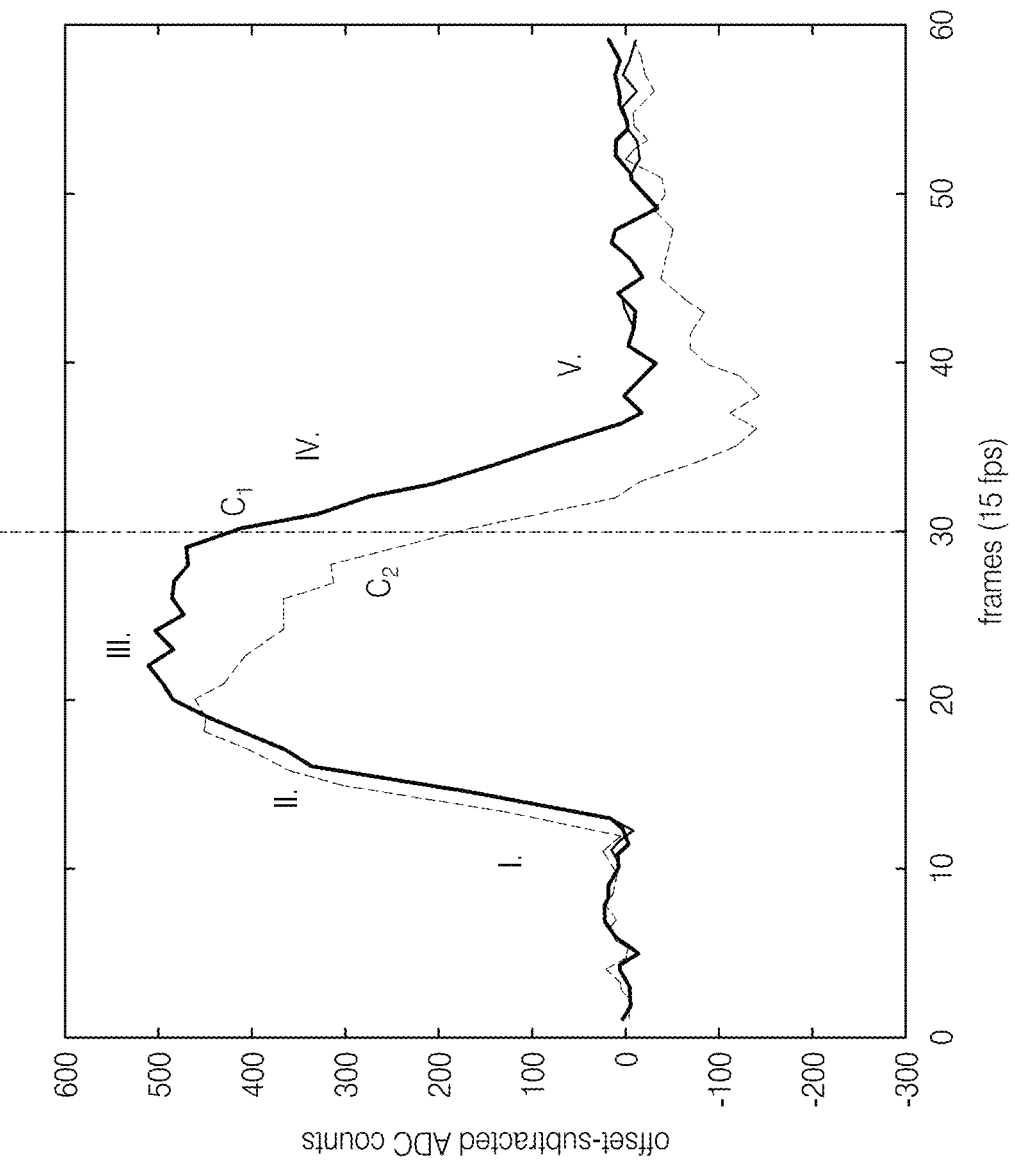

Regarding the progress of the cell imaging study for cells $C_1$ and $C_2$, in FIG. 7B, as the depolarizing solution reaches the cells at Phase I indicated on the graph, early indication of depolarization is demonstrated with an increasing signal for cells $C_1$ and $C_2$ and continues to increase in Phase II, until an equilibrium is reached at Phase III, where the response is sustained. As the wash solution is introduced in the flow cell and the depolarization solution is washed from the flow cell, recover is indicated at Phase IV of the graph, which proceeds until cells $C_1$ and $C_2$ are equilibrated to the wash solution at Phase V. The response of the cells is a signature of their presence on the sensor array surface, as compared to the slight negative response of the reference curve, the cells undergoing depolarization exhibit a strong positive voltage response, some 20 fold higher than baseline noise levels.

Figure 8A:
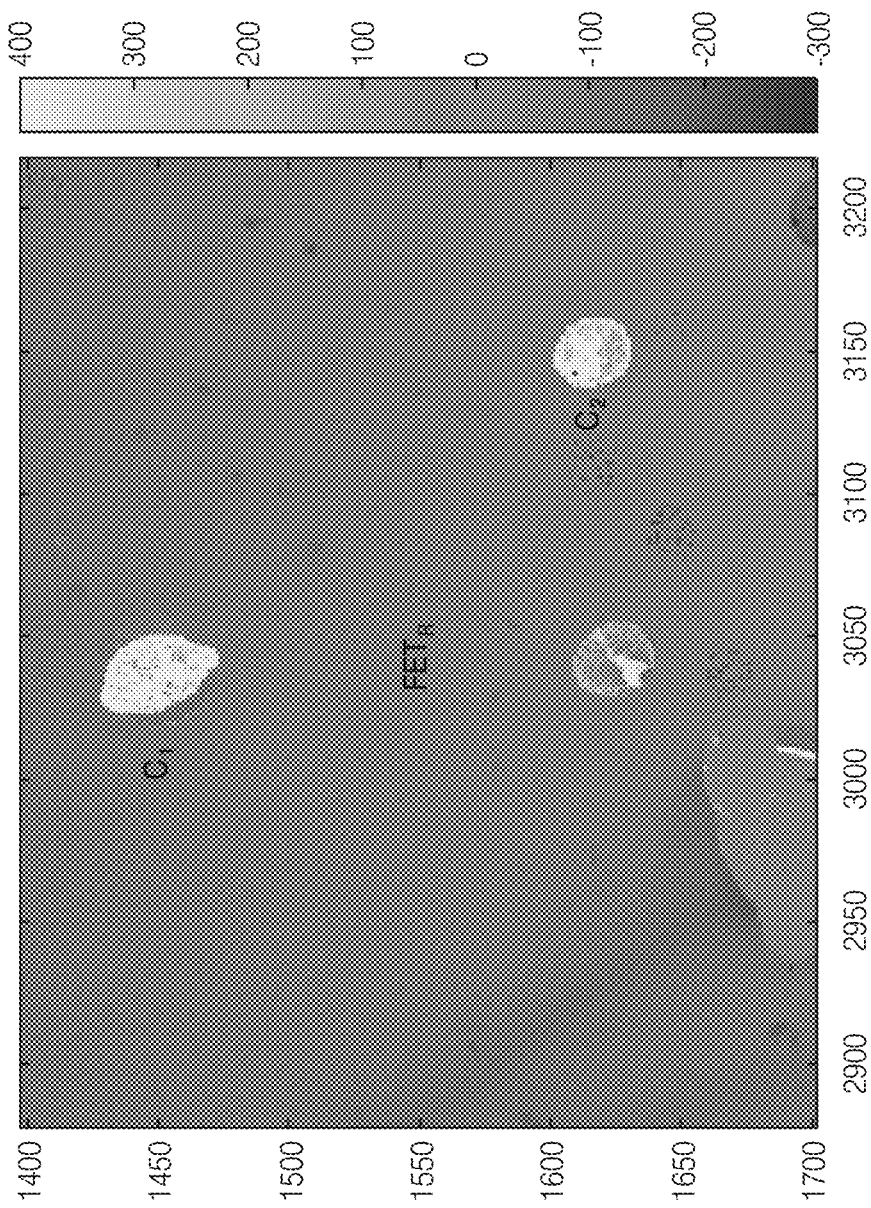
FIG. 8A is a cell electroscopic image created from the sensor array at the time point indicated in FIG. 8B.
Figure 8B:
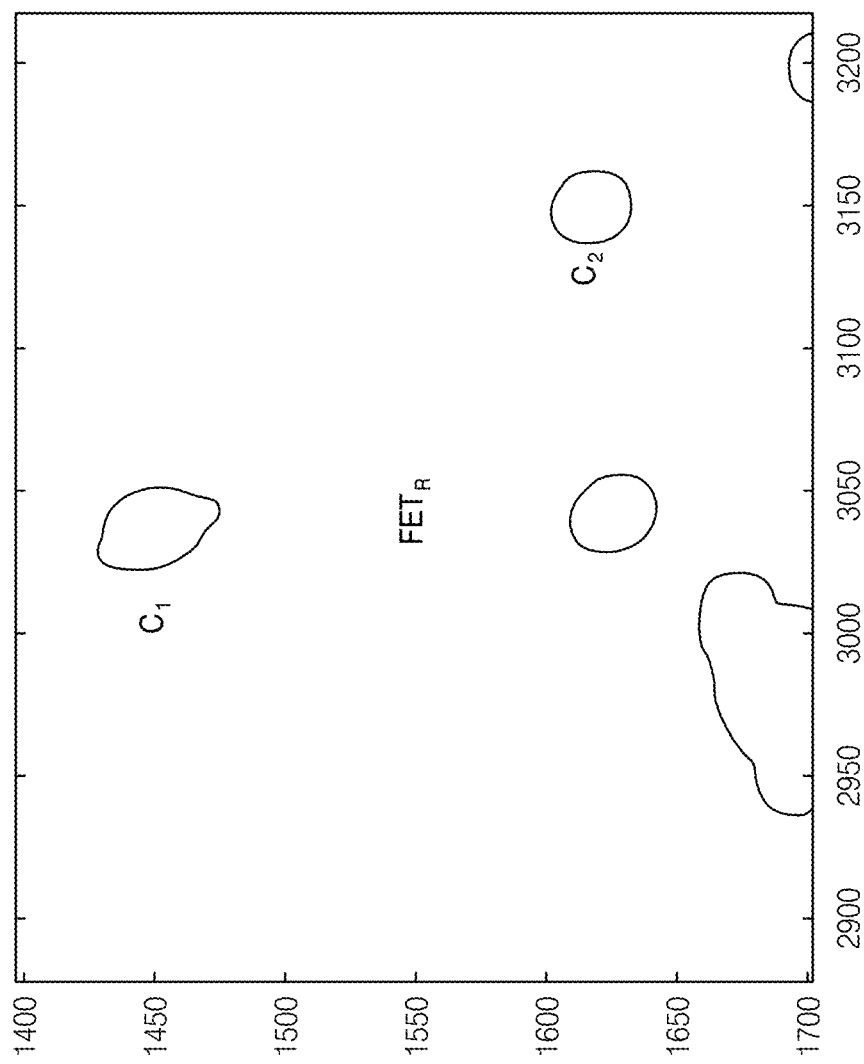
FIG. 8B is a line drawing rendering of the image of FIG. 8A.

The time indicated on FIG. 7B by the hatched line at 30 frames is the time corresponding to electroscopic image of FIG. 8A. FIG. 8B is a line drawing of the main features visualized in the electroscopic image of FIG. 8A. Based electroscopic imaging of cells on the sensor array, given that the pixel pitch for the sensor array device used in the study is 3μ, the size of the cells across the sensor array were estimated to have diameters of about 10 to 20 pixels, or 30μ to 60μ. As previously mentioned herein, the U-2OS cells were transduced with green florescent protein (GFP), so that the sensor array prepared for the electroscopic imaging experiment presented in FIG. 7A through FIG. 8B could also be imaged using florescence microscopy. Results from data collected from florescent microscopy imaging of the sensor array confirmed that cells across the sensor array had diameters in the range of 30μ to 60μ.

Figure 9A:
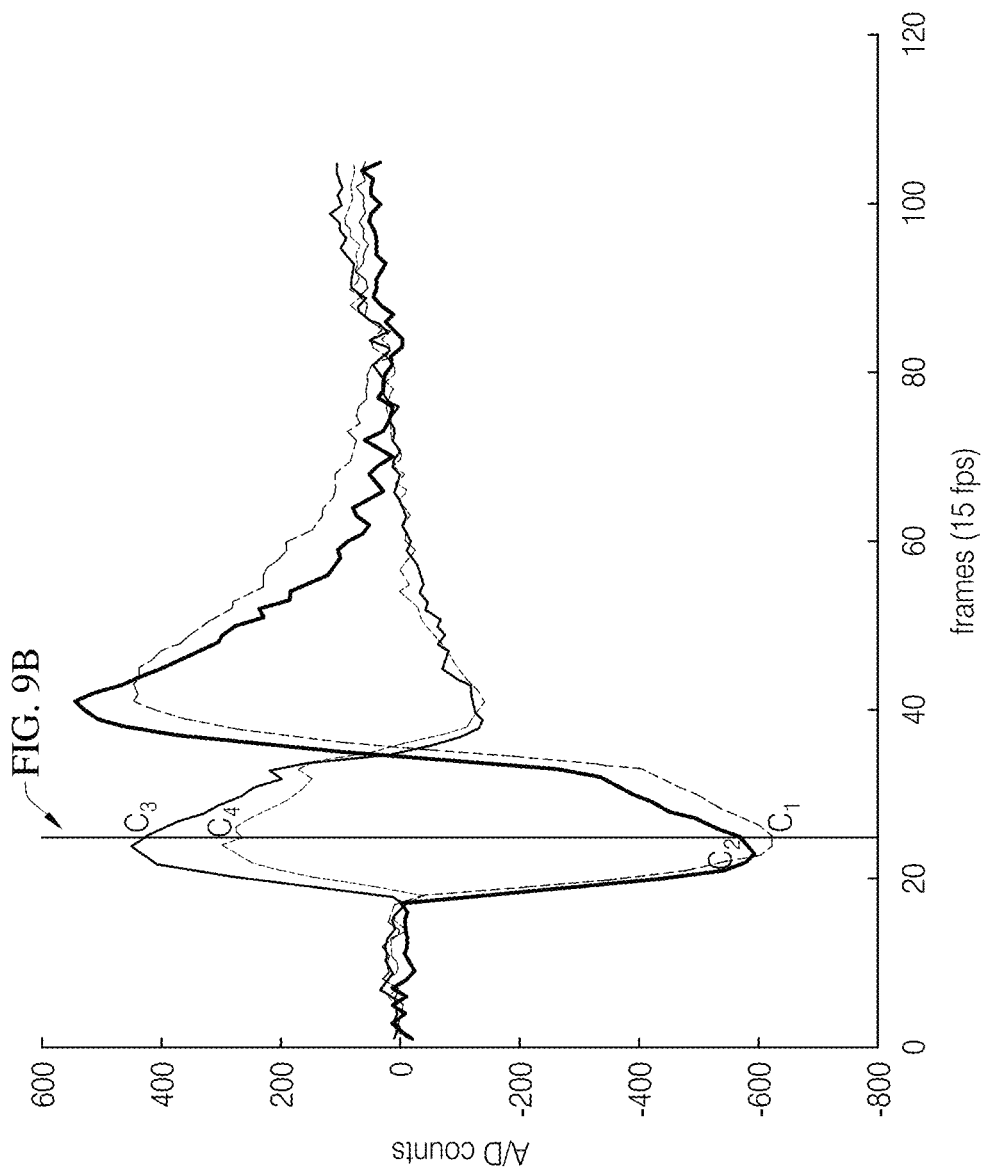
FIG. 9A illustrates temporal response curves for U-2OS cells ($C_1$ and $C_2$) in comparison to U-2OS cells transfected with various voltage-gated calcium channel subunits ($C_3$ and $C_4$), in which each cell type was treated with calcium ion channel blocker verapamil.
Figure 9B:
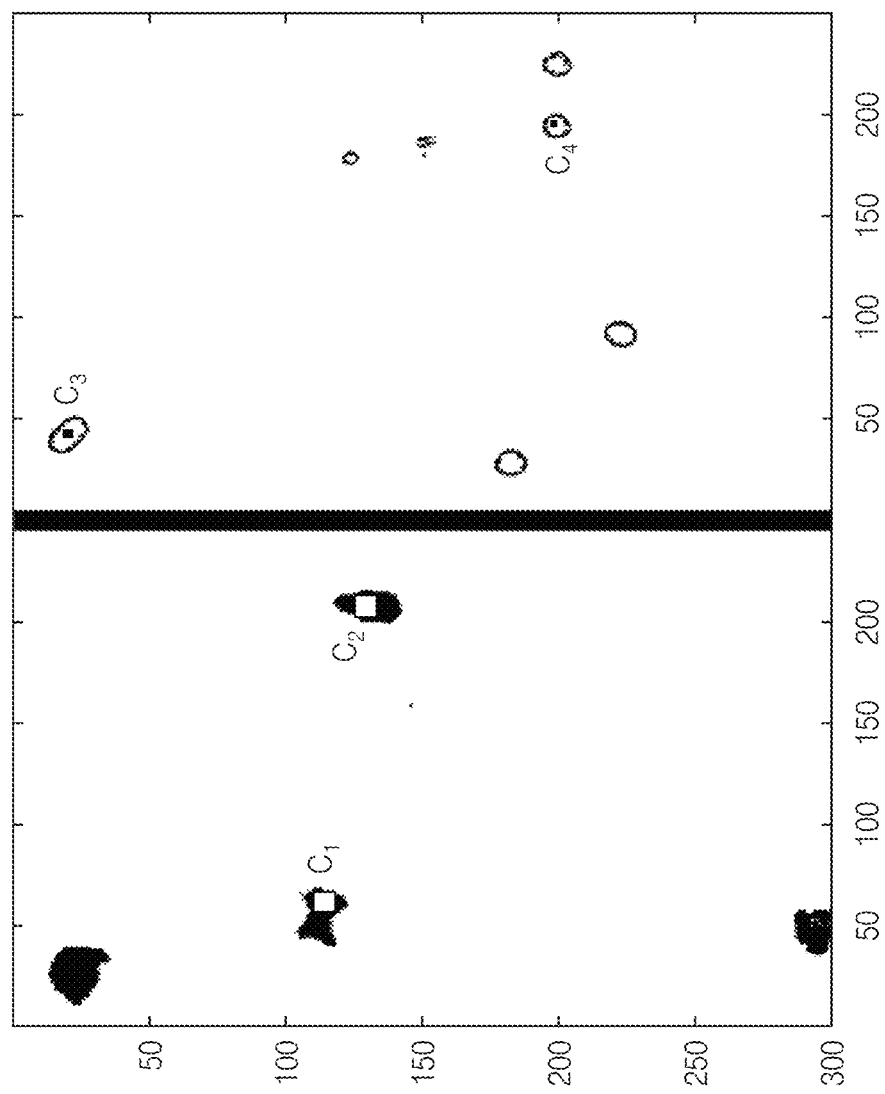
FIG. 9B is a composite electroscopic image of FIG. 9A taken at a time corresponding to frame 25 (1.7 seconds), as indicated in FIG. 9A, comparing two areas of interest in which the response of the U-2OS cells (left) is compared to the transfected U-2OS cells (right).
Figure 9C:
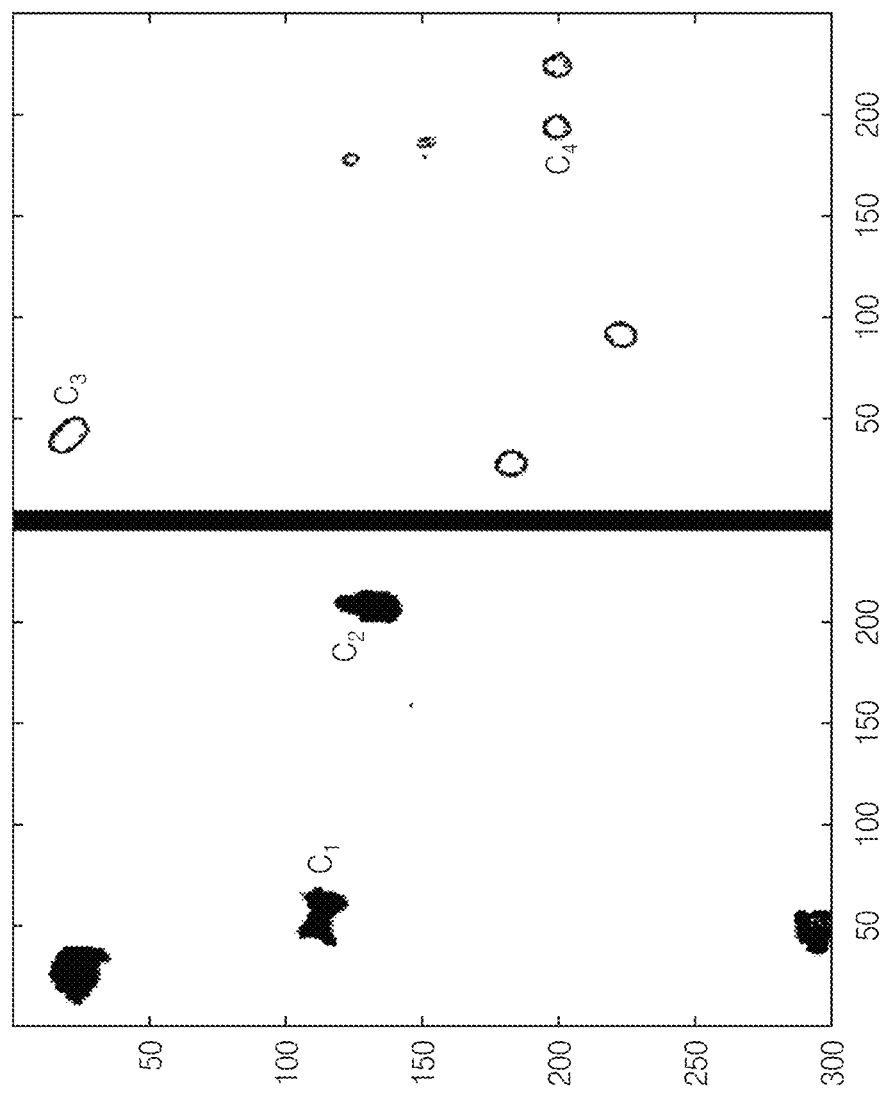
FIG. 9C is the composite electroscopic image of FIG. 9B for which the squares indicating an area within the cells have removed to provide a clear image of the cells.

FIG. 9A illustrates temporal response curves for U-2OS cells ($C_1$ and $C_2$) and U-2OS cells transfected with voltage-gated calcium channel alpha, beta and alpha-2-delta subunits ($C_3$ and $C_4$). The temporal response curves presented in FIG. 9A represent data collected over an area of interest for the U-2OS cells in comparison to transfected U-2OS cells cells, in which the impact of cell response for each type of cell treated with the calcium ion channel blocker verapamil was monitored through a cycle of an initial state of resting potential, followed by conditions for depolarization of membrane potential, and return to resting potential. FIG. 9B is an electroscopic image of FIG. 9A taken at a time corresponding to frame 25 (1.7 seconds), for which the squares within the cells in FIG. 9B indicate the pixels that were sampled for the data of FIG. 9A. FIG. 9C is the electroscopic image of FIG. 9B for which the squares within the cells in FIG. 9B have removed to provide a clear image of the cells.

The sensor array devices used in experiments from which data for FIG. 9A through FIG. 9C was generated was a Chip 2 device as summarized in the table of FIG. 3 selective for sensing hydrogen ion, and included a microwell array. The devices were prepared with a poly-D-lysine surface as previously described herein. Briefly, the sensor array device surface was soaked for 30 minutes with 70% ethanol in water, then rinsed with PBS before adding a solution of 0.1% poly-D-lysine, which was allowed to sit for two hours. The device was then rinsed twice with 200 μL of a cell culture medium, for example, McCoy's 5A modified medium with 10% fetal calf serum. After rinsing with the cell culture medium, the devices were ready for plating with a cell suspension.

Preparation of transfected cells was done using a cell suspension of 1×10^6 cells per mL. Mammalianized Bac-Mam gene delivery particles encoding a mixture of voltage-gated calcium ion channel alpha, beta and alpha-2-delta subunits was added to the cell suspension to reconstitute functional channels. Functional voltage-gated calcium ion channels require at a minimum of both alpha and beta subunits, with alpha-2-delta serving to boost surface expression and ionic flux. BacMam viral transduction was achieved by pre-mixing and adding the particles to cells in rough proportions of tenfold excess of viral particle to cell number. Control (no virus) and virus treated cells were plated onto the sensor devices and placed into a cell culture incubator overnight to allow adherence and expression of the functional ion channels before experimentation was carried out the following day.

During the experiment, control or viral transduced cells were exposed to an elevated 30 mM KCl depolarizing stimulus in the presence of the calcium ion channel blocker verapamil at 10 μM. The temporal response curves of FIG. 9A illustrate distinguishable differences in the signature responses obtained from cells in the control set ($C_1$ and $C_2$) vs cell transfected with voltage-gated calcium channels, ($C_3$ and $C_4$). The findings presented in FIG. 9A through FIG. 9C demonstrate that cell analysis systems and methods of the present teachings can readily discriminate between cells expressing and not expressing voltage-gated calcium ion channels on the basis of the selective activity of a blocker on cultures that express the target protein.

Figure 10A:
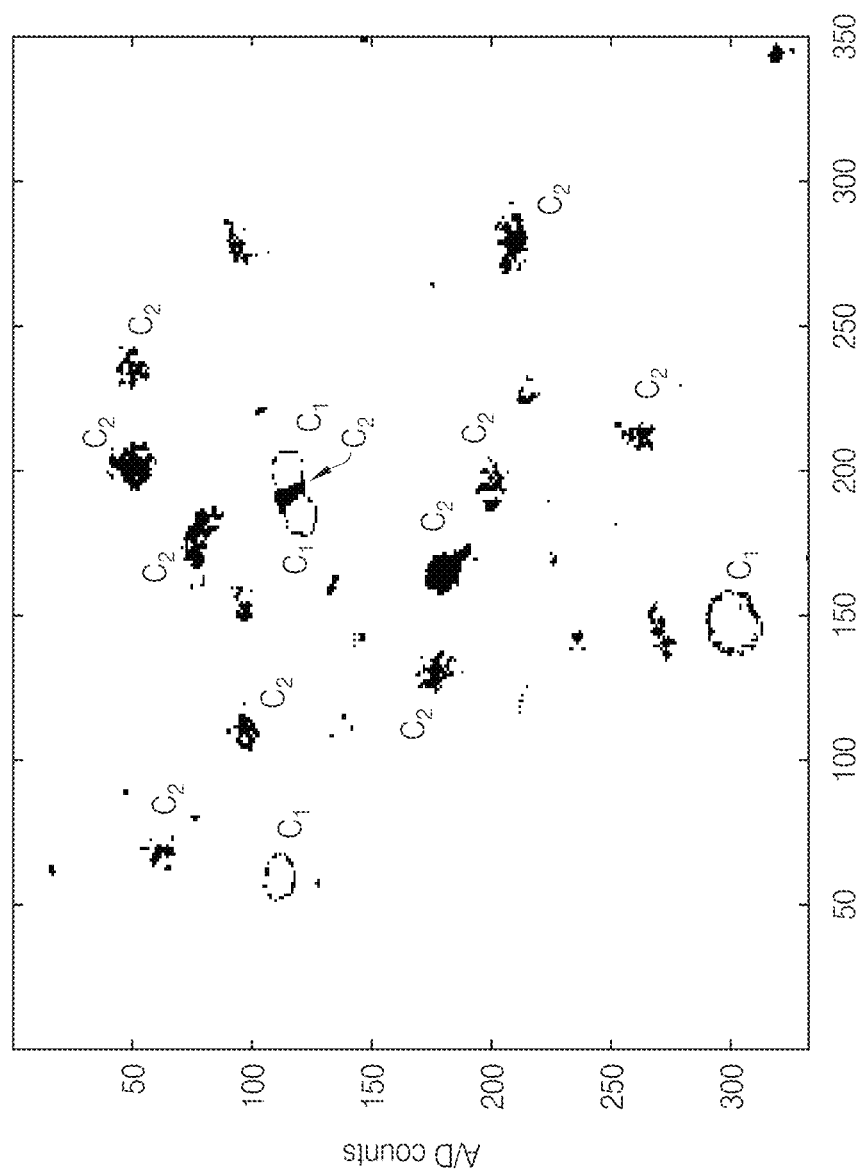
FIG. 10A is an electroscopic image of rat neonatal cells subjected to a pulse of 4.5 mM KCl, in which some cells ($C_1$) exhibit a depolarization response vs. other exemplary cells in the population remaining in a resting state ($C_2$).
Figure 10B:
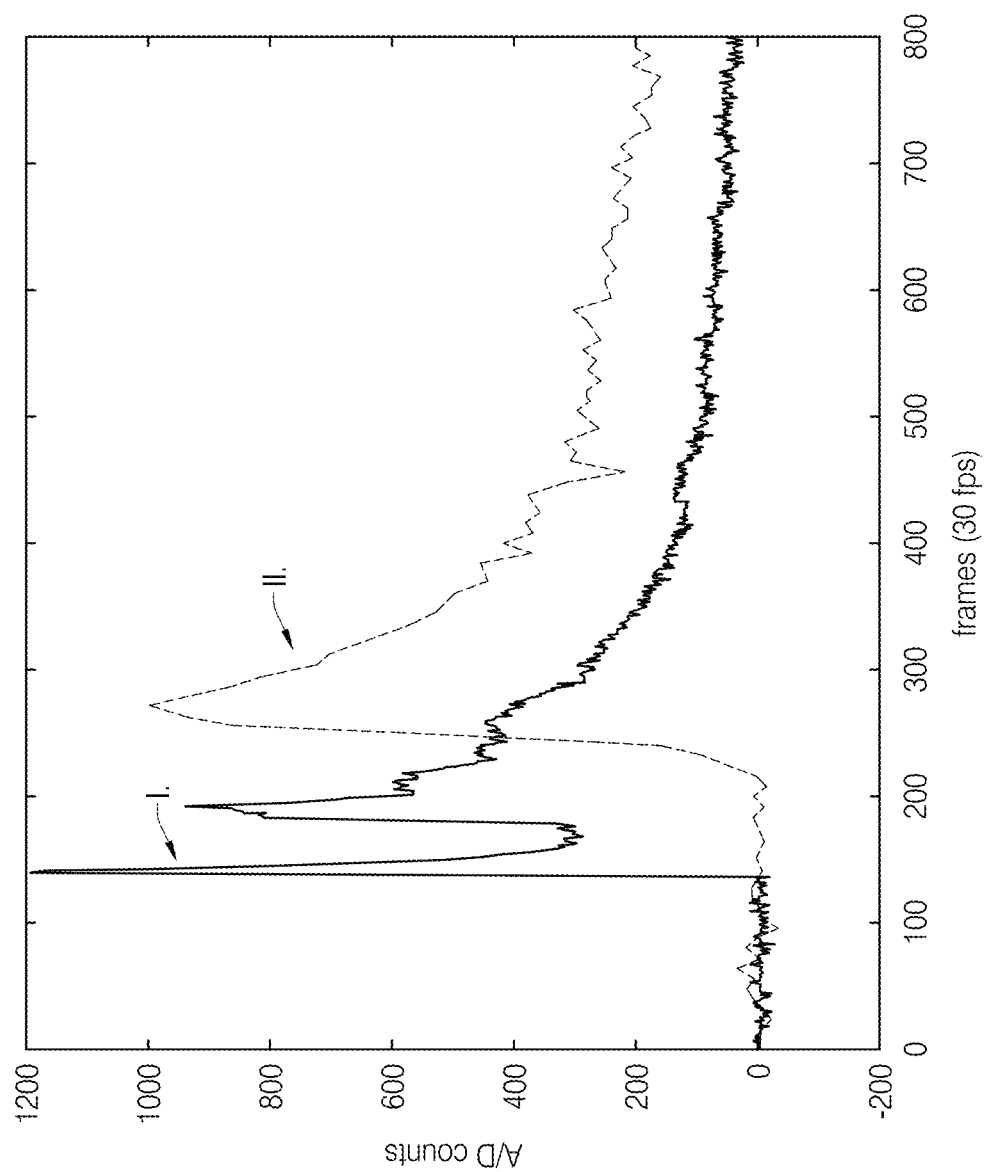
FIG. 10B is a comparison of temporal response curves for rat neonatal cells subjected to a pulse of 4.5 mM KCl, in which the experiment was performed on two different devices with different data acquisition rates.

FIG. 10A is an electroscopic image of rat neonatal hippocampus cells subjected to a pulse of 4.5 mM KCl. FIG. 10B is a comparison of temporal response curves for rat neonatal cells subjected to a pulse of 4.5 mM KCl, in which the experiment was performed on two different devices with different data acquisition rates.

In reference to the table of FIG. 3 summarizing array device attributes, the sensor array devices used in experiments from which data for FIG. 10A and FIG. 10B was generated was a device having the dimensions of Chip 2, for which data was collected at a frame rate of 30 samples/second. The sensor array device used in experiments for which data in FIG. 10B I was generated was a device having the dimensions of Chip 1, in which the active area of the device was windowed down to an area of interest 50% of the total device area to provide a maximum frame rate of 240 samples/second. Both Chip 1 and Chip 2 devices were ISFET devices selective for sensing hydrogen ion and included a microwell array. The devices were prepared with a poly-D-lysine surface as described herein for the preparation of the devices used in experiments with voltage-gated calcium channel of FIG. 9A through FIG. 9C. Rat neonatal hippocampus cells were dissociated from intact rat E18 neonatal hippocampi and resuspended at a density of 1×10^6 cells per mL, then plated onto the devices. The devices were placed in a cell culture incubator and fresh neuronal culture medium was exchanged over the plated cells every third day for a ten-day period, which allowed for adhesion and maturation of the cells to an excitable phenotype capable of displaying spontaneous depolarization activity. The rat neonatal hippocampus cells were tested for spontaneous activity during a solution pulse from a basal potassium chloride (KCl) concentration of 2.5 mM to 4.5 mM.

The cell activity of the preparation was observed for spontaneous depolarization as demonstrated in the electroscopic image of FIG. 10A. FIG. 10B demonstrates the impact of frame rate on data resolution. In FIG. 10B, a temporal response curve with two peaks is observed for the sensor device with a frame rate of 240 samples/sec (FIG. 10B-I) versus a temporal response curve with a single peak observed for the sensor device with a frame rate of 30 samples/sec (FIG. 10B-II). The electroscopic data of FIG. 10A and the temporal response curves of FIG. 10B illustrate the ability of cell analysis systems and methods of the present teachings to visualize intrinsic electrical activity from a primary cell type known to fire action potentials in culture after a maturation period of ten days.

Figure 11:
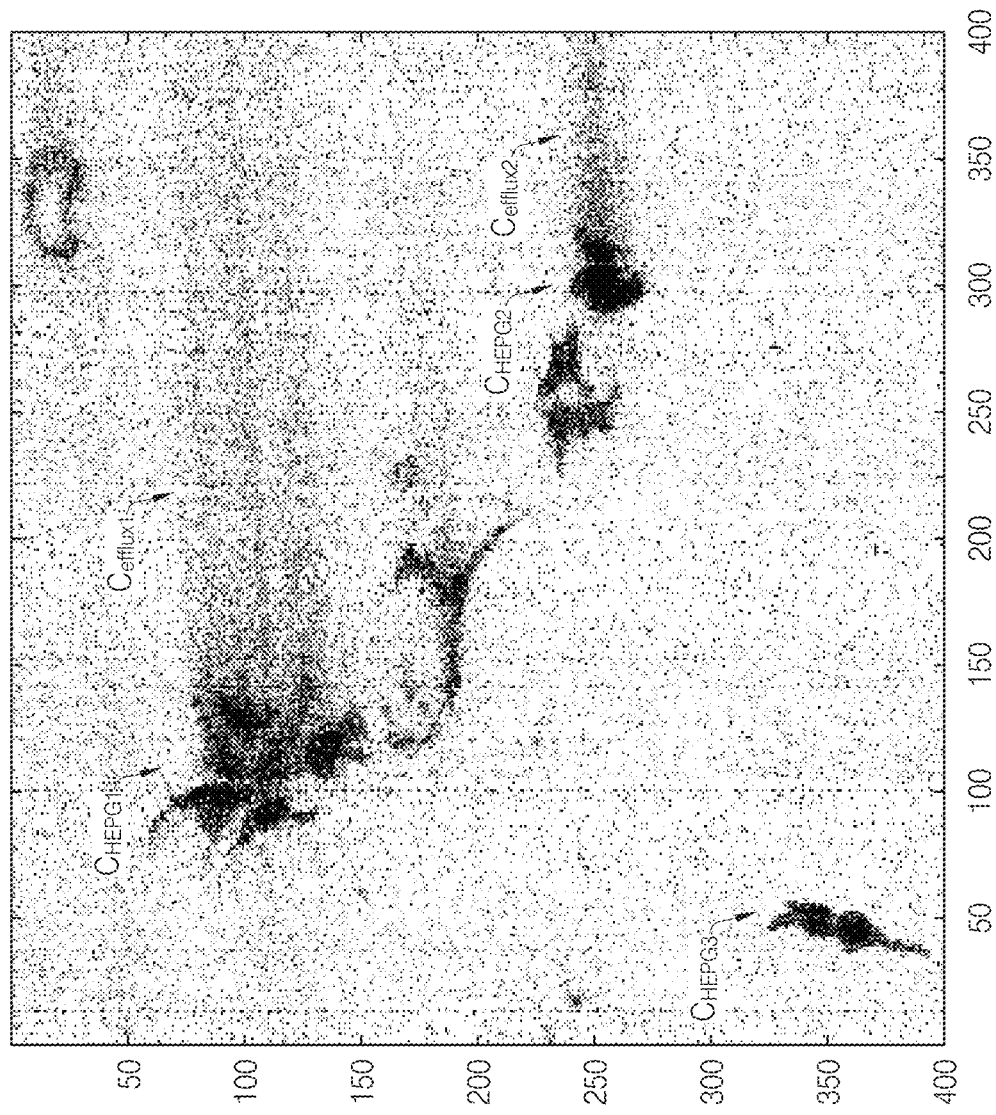
FIG. 11 is an electroscopic image of HEPG2 cells subjected to the mitochondrial toxin carbonyl cyanide-4-(trifluoromethoxy)phenylhydrazone (FCCP), in which some exemplary cells are indicated in association with cellular efflux.

FIG. 11 is an electroscopic image of cells from an immortalized human hepatic cell line (HEPG2 cells; ATCC catalogue number ATCC-HB-8065) cells subjected to mitochondrial toxin carbonyl cyanide-4-(trifluoromethoxy)phenylhydrazone (FCCP), in which some exemplary cells are indicated in association with streams of cellular efflux. The HEPG2 cell line is used in cell biology as a model for liver hepatocellular carcinoma, and additionally is also used for studies of LDL and cholesterol import and liver toxicology.

The sensor array devices used in experiments from which data for FIG. 11 was generated was a Chip 2 device of FIG. 3 selective for sensing hydrogen ion, and included a microwell array. The devices were prepared with a poly-D-lysine surface as described herein for the preparation of the devices used in experiments with voltage-gated calcium channel of FIG. 9A through FIG. 9C. The HEPG2 cells were resuspended at $1 \times 10^6$ cells per mL and plated onto chips for overnight incubation in a cell culture incubator to allow the cells to adhere to the prepared surface of the chip. The mitochondrial protonophore FCCP was tested at a concentration of 100 μM, which is a concentration known to elicit responses leading to cell death. An electroscopic image from the experiment is presented in FIG. 11.

During the application of FCCP, cellular responses were observed demonstrating the ability of cell analysis systems and methods of the present teachings to visualize the efflux of cellular contents into the laminar flow system. This is depicted for two cells in FIG. 11, $C_{HEPG1}$ and $C_{HEPG2}$, for which the the efflux of cellular contents is indicated by Cefflux1 and Cefflux2, respectively. Notably, not all cells demonstrated the efflux activity, as depicted in FIG. 11 for $C_{HEPG3}$. These results indicate that cell analysis systems and methods of the present teachings can further discriminate between acute, novel phenotypes exhibited in response to toxin treatment.

Figure 12A:
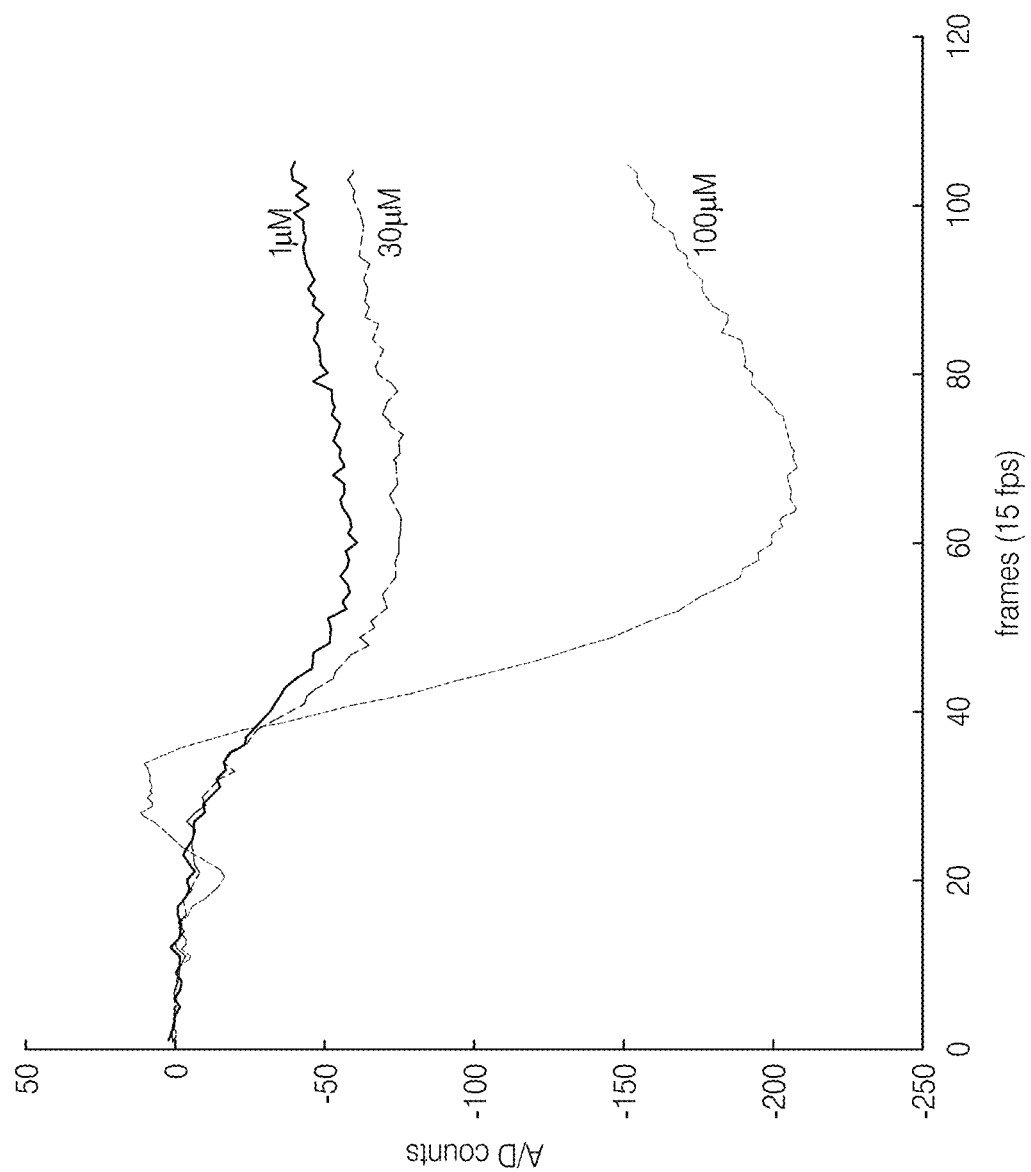
FIG. 12A illustrates averaged background-subtracted temporal dose-response curves for U-2OS cells treated with FCCP.
Figure 12B:
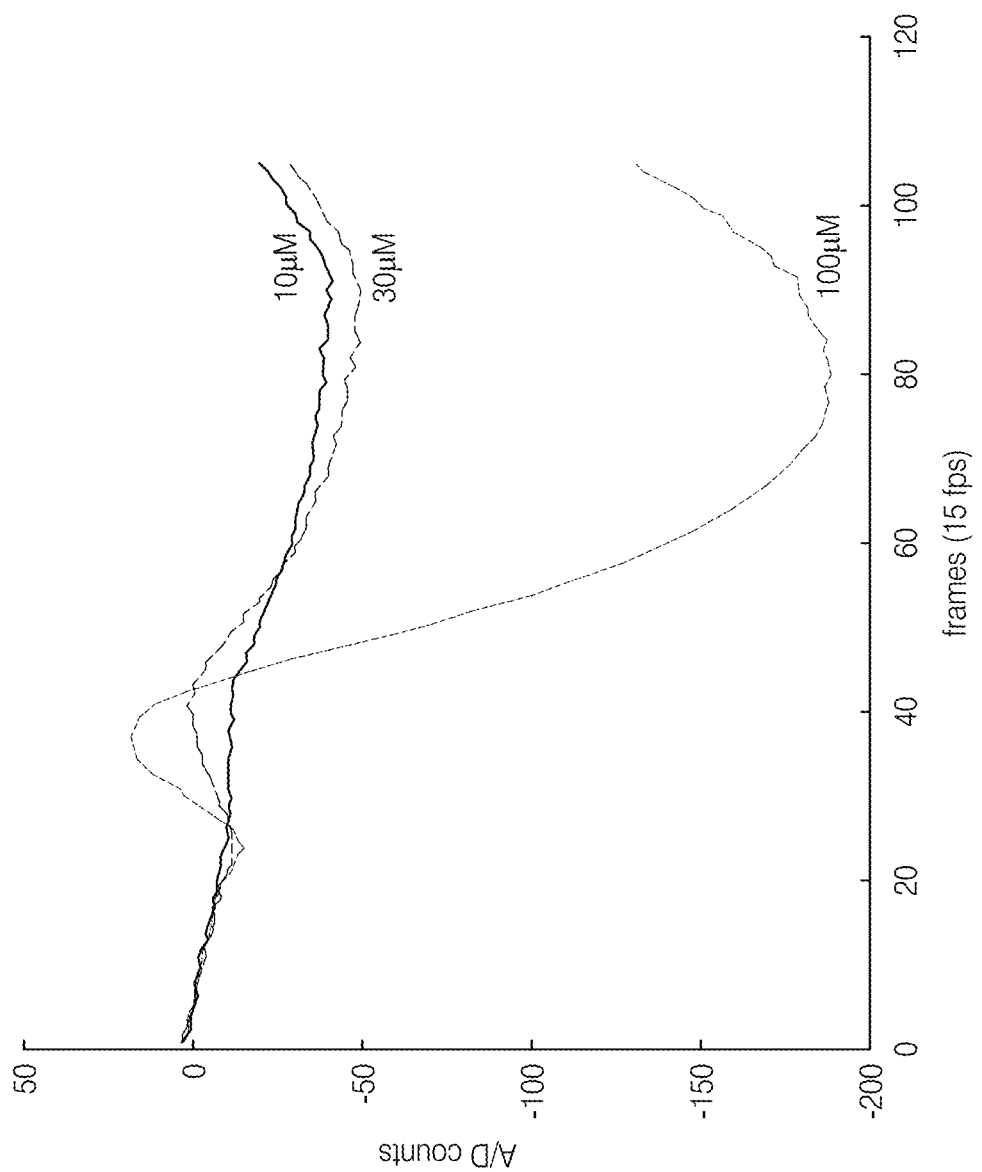
FIG. 12B illustrates averaged background-subtracted temporal dose-response curves for U-2OS cells pretreated with a nutrient solution containing oligomycin before being treated with FCCP.

FIG. 12A illustrates averaged background-subtracted temporal dose-response curves for U-2OS cells treated with FCCP. FIG. 12B illustrates averaged background-subtracted temporal dose-response curves for U-2OS cells pretreated with a nutrient solution containing oligomycin before being treated with FCCP.

In reference to the table of FIG. 3 summarizing array device attributes, the sensor array devices used in experiments from which data for FIG. 12A and FIG. 12B was generated using a Chip 2 device for the data presented in FIG. 12A and Chip 1 device for the date presented in FIG. 12B. Both Chip 1 and Chip 2 devices were ISFET devices selective for sensing hydrogen ion, and included a microwell array. The devices were prepared with a poly-D-lysine surface as described herein for the preparation of the devices used in experiments with voltage-gated calcium channel of FIG. 9A through FIG. 9C. The U-2OS cells were resuspended at $1 \times 10^6$ cells per mL and plated onto chips for overnight incubation in a cell culture incubator to allow the cells to adhere to the prepared surface of the chip. To test for dose-dependence of the FCCP treatment, cells were exposed to a series of concentration jumps during the experiment as indicated in FIG. 12A and FIG. 12B. In FIG. 12A, experiments were carried out in the absence of oligomycin, and in 12B, the FCCP dose-response curve was generated in the presence of oligomycin.

The data in FIG. 12A and FIG. 12B are composed of averaged cellular responses from samples tested with FCCP. The data show that dose-dependent FCCP responses are readily distinguishable in the absence and presence of oligomycin. For the current state of the art for cell analysis tools, oligomycin is frequently used as a pretreatment to FCCP to potentiate FCCP responses in cells. In contrast, cell analysis systems of the present teachings need no pharmacological priming to prove robust, dose dependent FCCP temporal response curves.

Figure 13A:
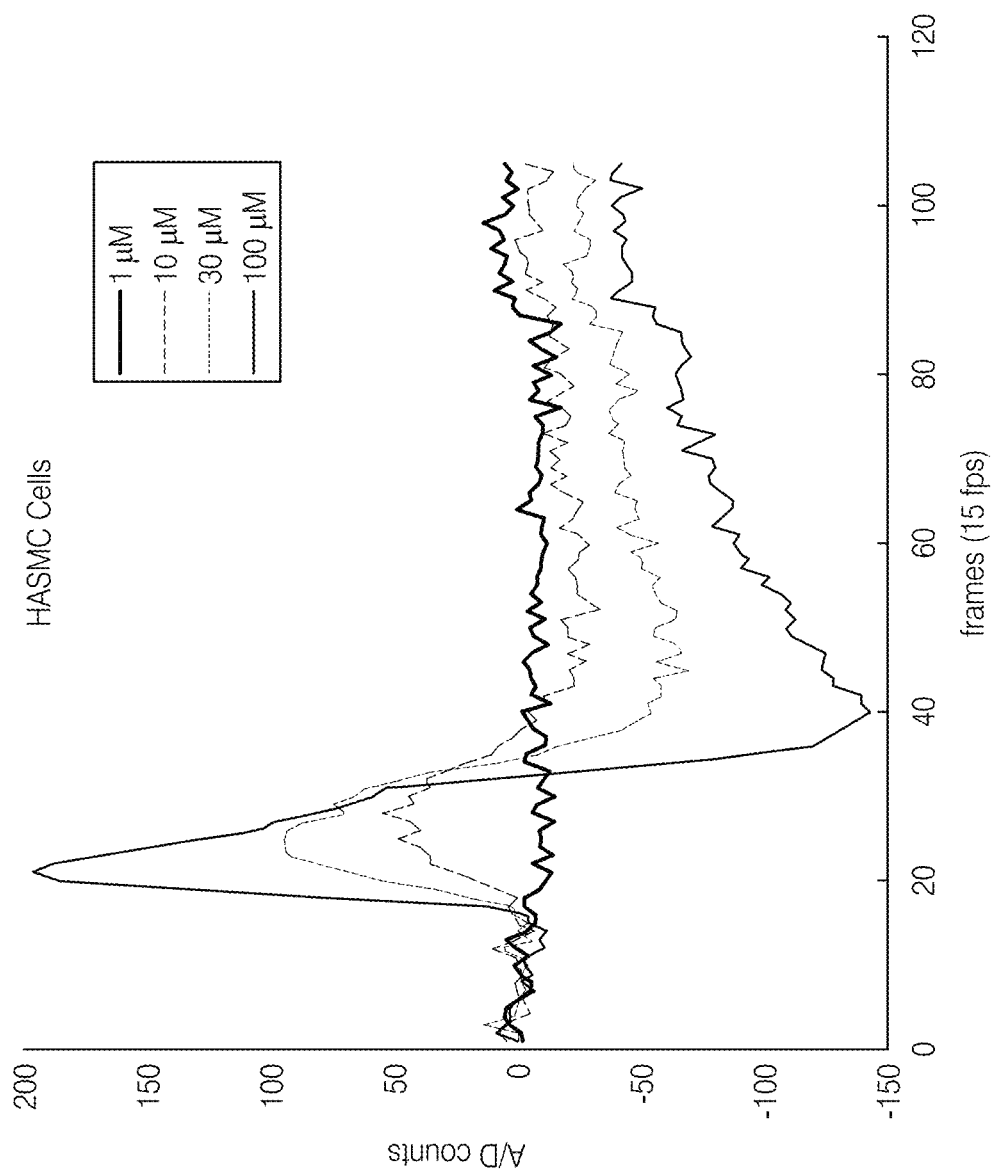
FIG. 13A through FIG. 13C are average background-subtracted temporal dose-response curves for a mixture of different cells types subjected to FCCP.
Figure 13B:
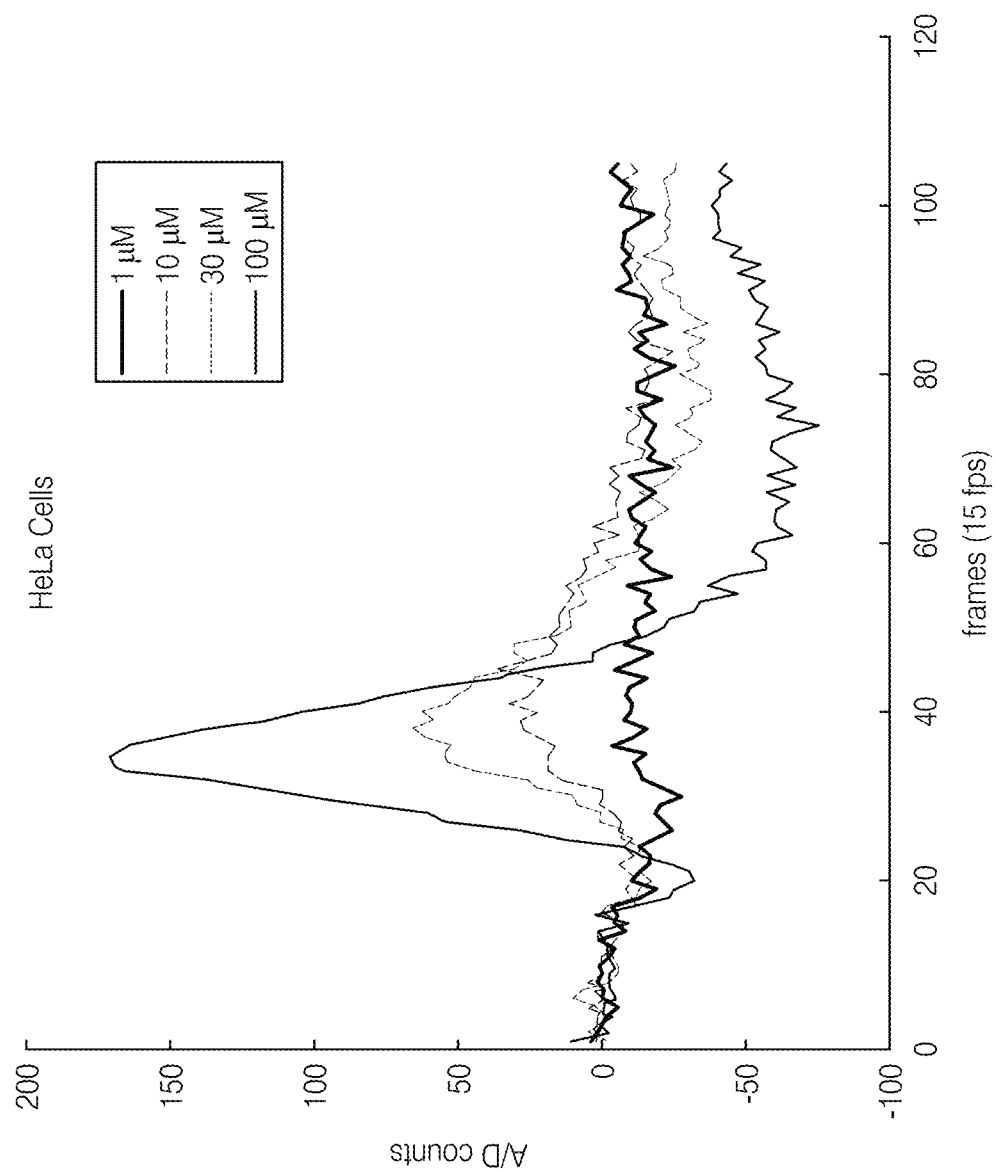
Figure 13C:
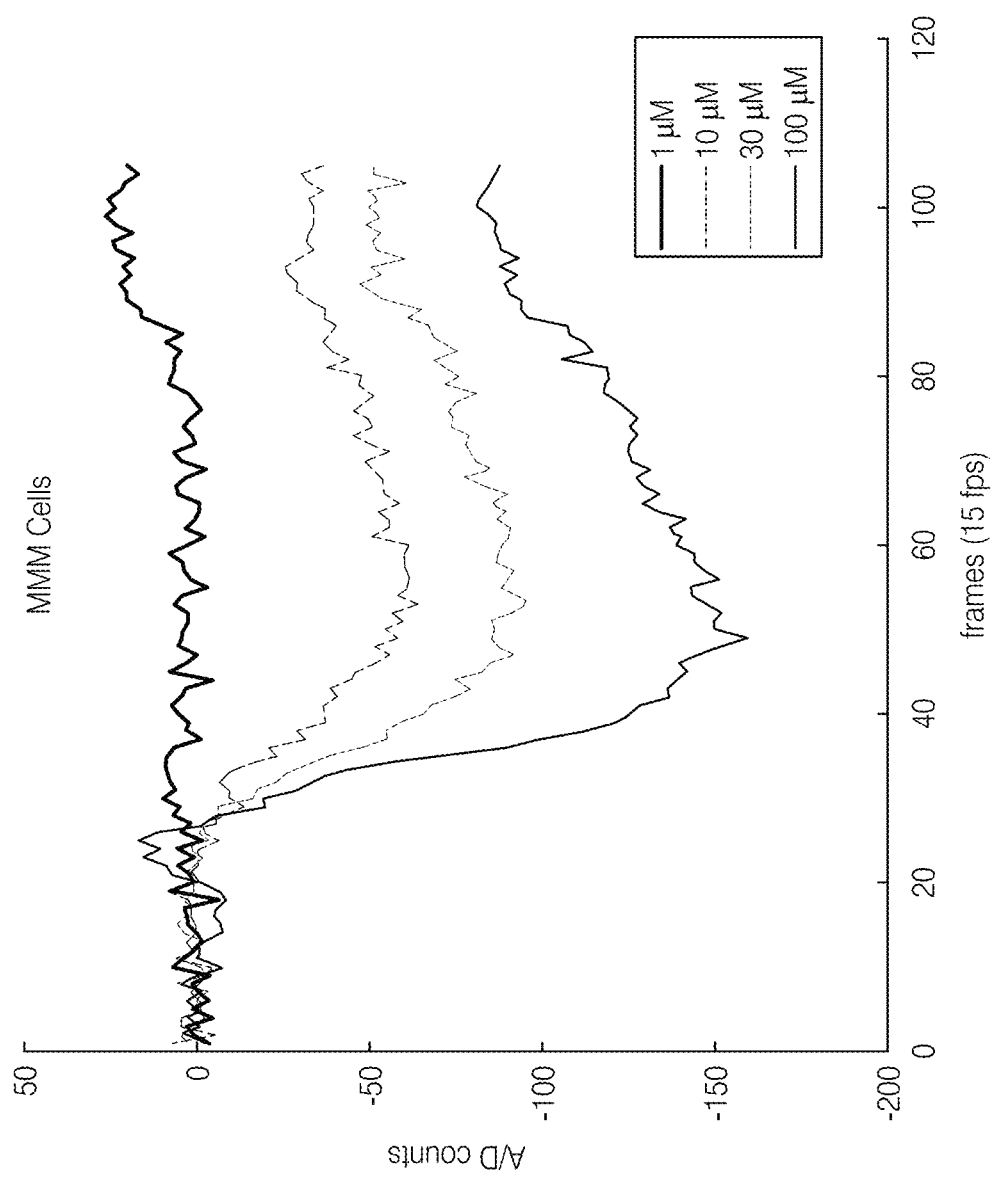

For the experiments for which data is presented in FIG. 13A through FIG. 13C, three distinct cell types were chosen to test for the ability of the instrument to discriminate cell type based on response to FCCP. To generate the data set comparing widely varying cell types, donor-derived primary human aortic smooth muscle (HASM) cells (HASMC; Gibco cat #C0075C), human cervical cancer cells (HeLa cells; ATCC catalogue number CRM CCL 2) and a mouse-derived leukemia cell line (MMM cells; ATCC catalogue number J774A.1) were selected for the study.

Figure 14A:
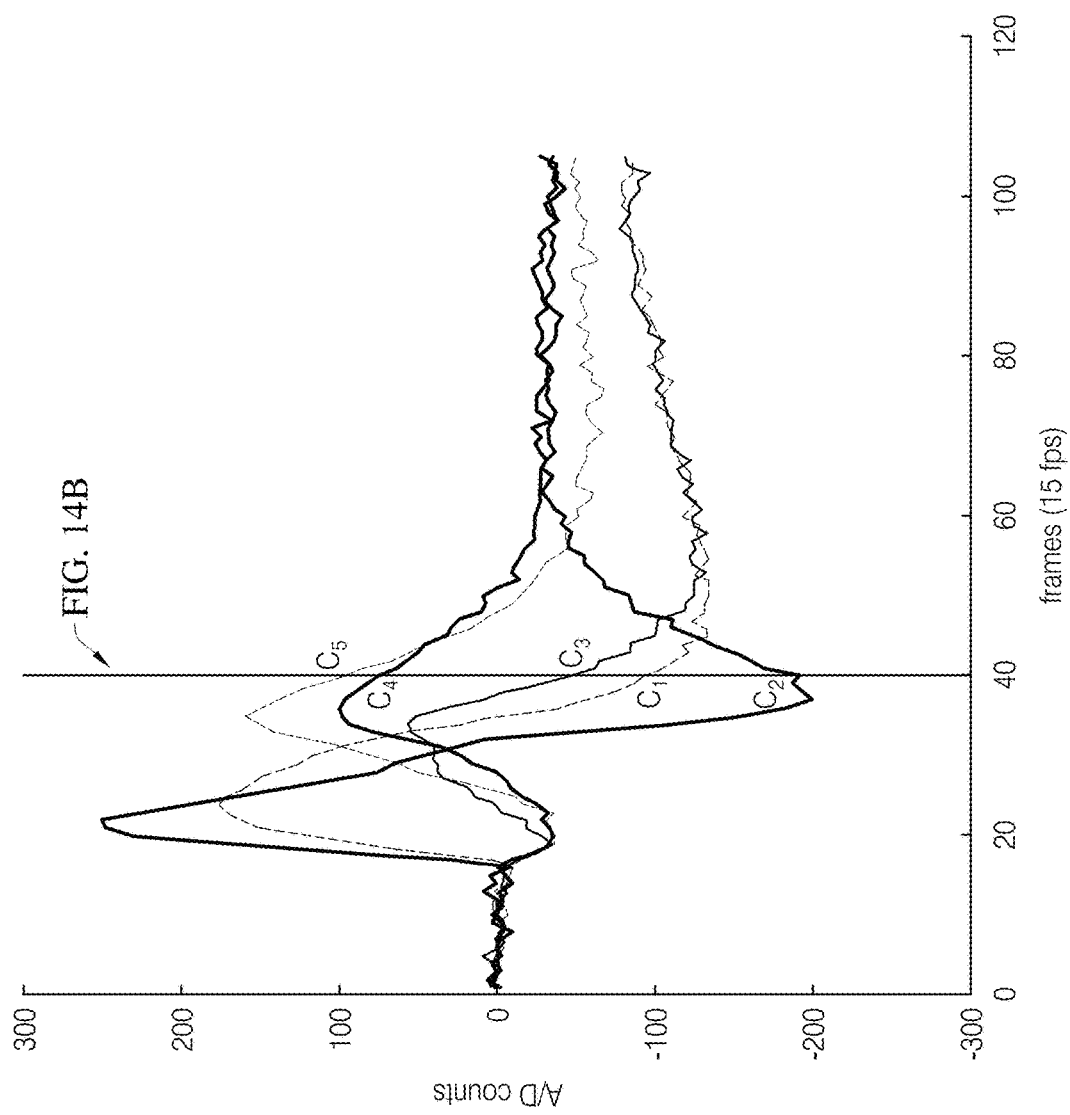
FIG. 14A illustrates temporal dose-response curves for selected cells in the mixture of cell presented in FIG. 13A through FIG. 13C.
Figure 14B:
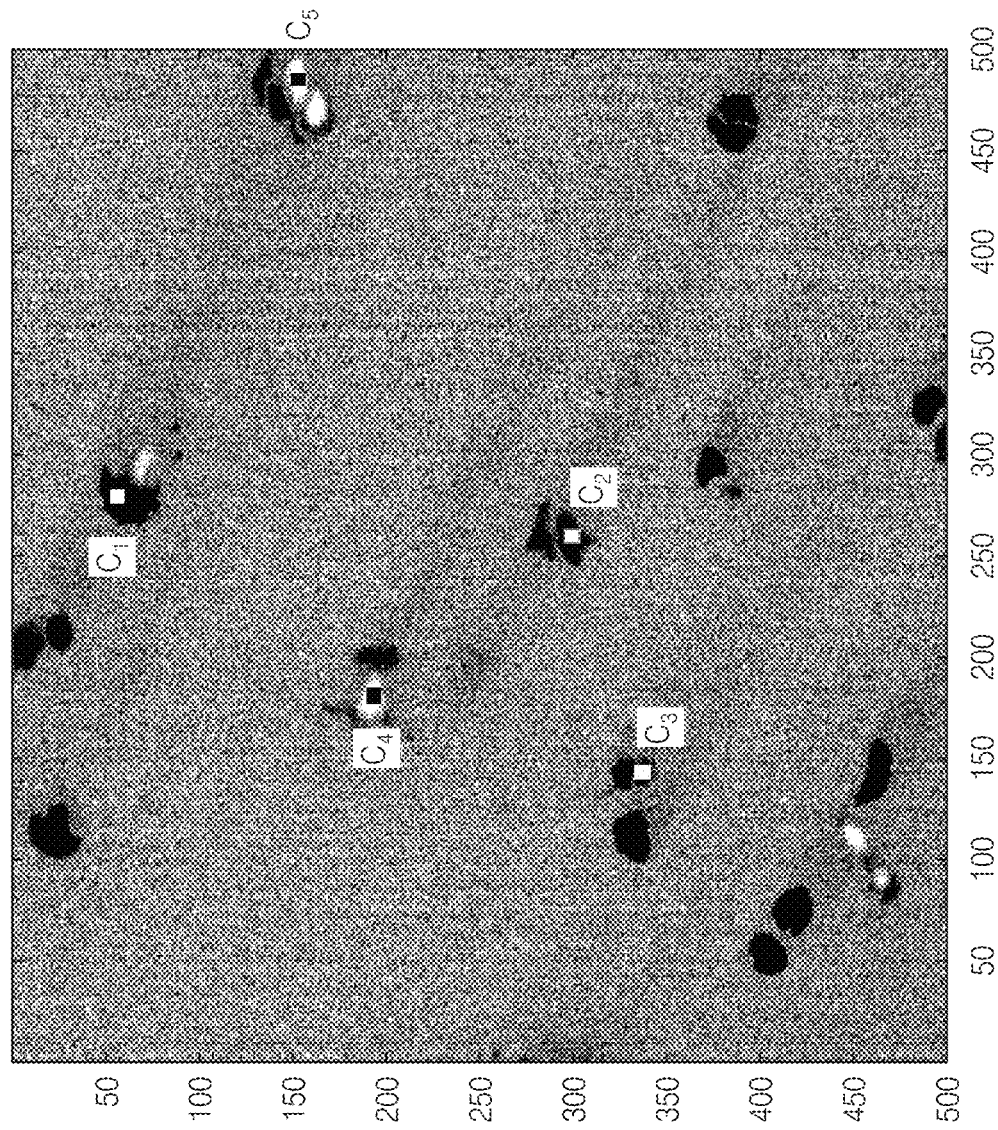
FIG. 14B is an electroscopic image of the experiment of FIG. 14A taken at a time corresponding to frame 40 (2.7 seconds).
Figure 14C:
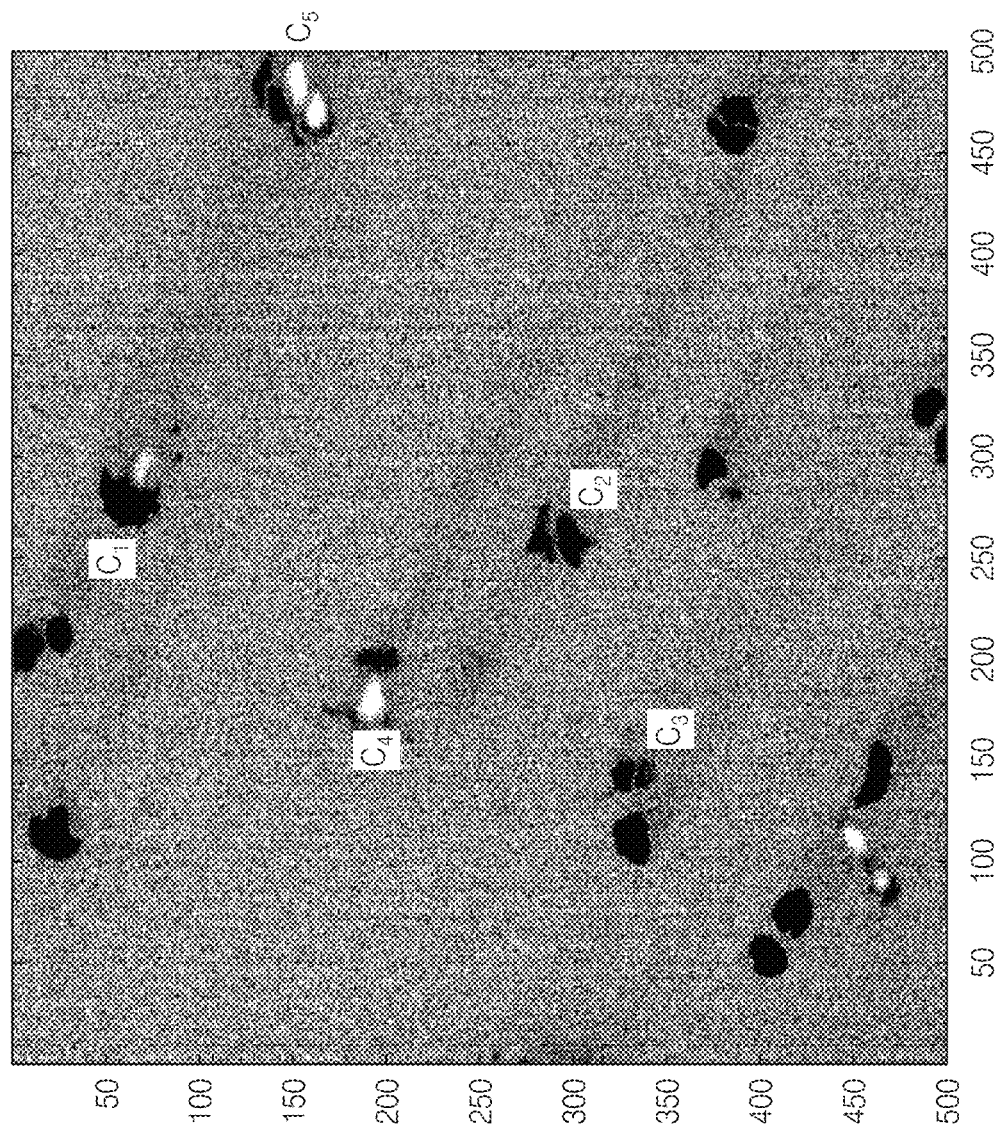
FIG. 14C is the electroscopic image of FIG. 14B for which the squares within the cells in FIG. 13B have removed to provide a clear image of the cells.

FIG. 13A through FIG. 13C are average background-subtracted temporal dose-responses curves for each type of cell line tested individually on separate devices. FIG. 13A is set of dose-response curves for HASM cells, FIG. 13B is a set of dose-response curves for HeLa cells, and FIG. 13C is a set of dose-response curves for MMM cells. For the data shown in FIG. 14A through FIG. 14C, a mixture of the cells were exposed to 100 μM FCCP and their responses recorded in order to understand whether or not the different cell types could be identified by their response to FCCP. FIG. 14A illustrates composite temporal dose-response curves for selected cells in a mixture of different cell types in which the cells were subjected to FCCP. FIG. 14B is an electroscopic image of the experiment of FIG. 14A taken at a time corresponding to frame 40 (2.7 seconds), in which squares within the cells indicate the pixels that were sampled for the data of FIG. 14A. FIG. 14C is the electroscopic image of FIG. 14B for which the squares within the cells in FIG. 13B have removed to provide a clear image of the cells.

The sensor array devices used in experiments from which data for FIG. 13A though FIG. 14C was generated was a Chip 2 device of FIG. 3, selective for sensing hydrogen ion, and included a microwell array. The devices were prepared with a poly-D-lysine surface as described herein for the preparation of the devices used in experiments with voltage-gated calcium channel of FIG. 9A through FIG. 9C. Each cell line was resuspended at $1 \times 10^6$ cells per mL and then mixed in even proportions before plating onto the devices for overnight incubation in a cell culture incubator to allow the cells to adhere to the prepared surface of the chip.

As the temporal response curves of FIG. 13A through FIG. 13C represent each of three cell types of distinct tissue origin tested individually on separate devices, it is notable that each cell type displays a distinct kinetic and amplitude response to FCCP. The data presented in FIG. 13A through FIG. 13C suggest the potential for identification of each cell line by its signature response to a pharmacological probe.

FIG. 14A represents data collected from an analysis of all three cell types on a single chip. Using waveform analysis on the temporal response data presented in FIG. 14A, $C_1$ and $C_2$ were identified as HASM cells, $C_3$ as an MMM cell, and $C_4$ and $C_5$ were identified as HeLa cells. At the time at which the electroscopic image of FIG. 14C was taken, the electroscopic image captured differences in behavior for the HeLa cells ($C_4$ and $C_5$) in comparison to HASM cells and the MMM cell ($C_1$-$C_3$). Collectively, the data presented in FIG. 13A through FIG. 13C and FIG. 14A through FIG. 14C demonstrate the potential for systems and methods of the present teachings to use signature cellular responses and behaviors to identify distinctly different cell lines in a mixed population of cells.

Figure 15A:
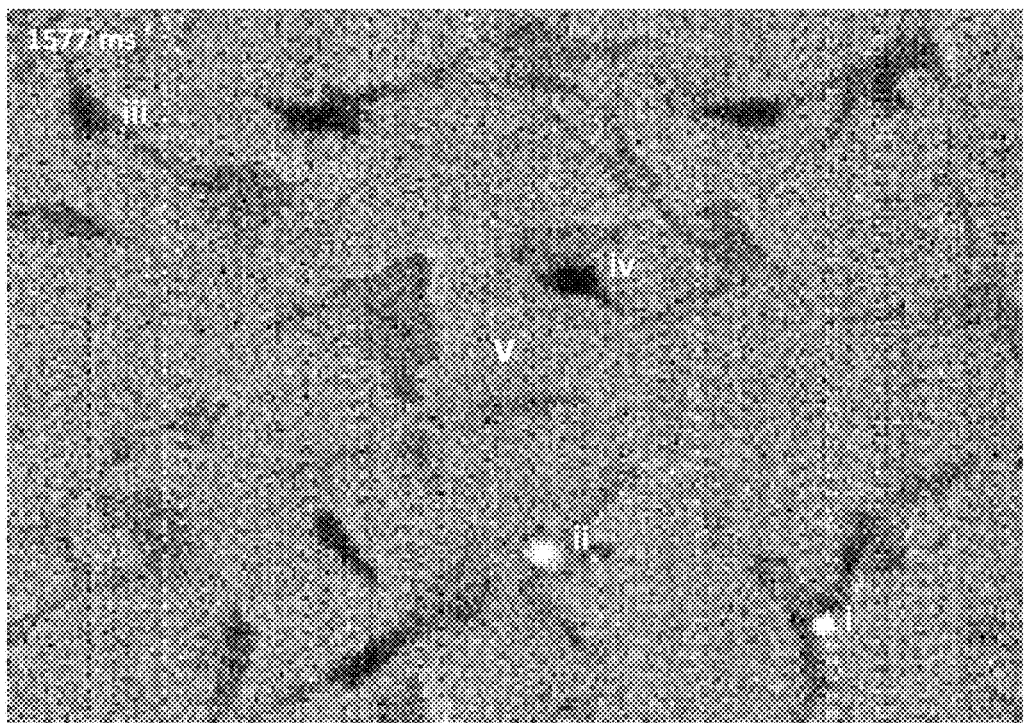
FIG. 15A and FIG. 15B are electroscopic images of U-2OS cells transfected with various voltage-gated calcium channel subunits ($C_3$ and $C_4$) at consecutive time points.
Figure 15B:
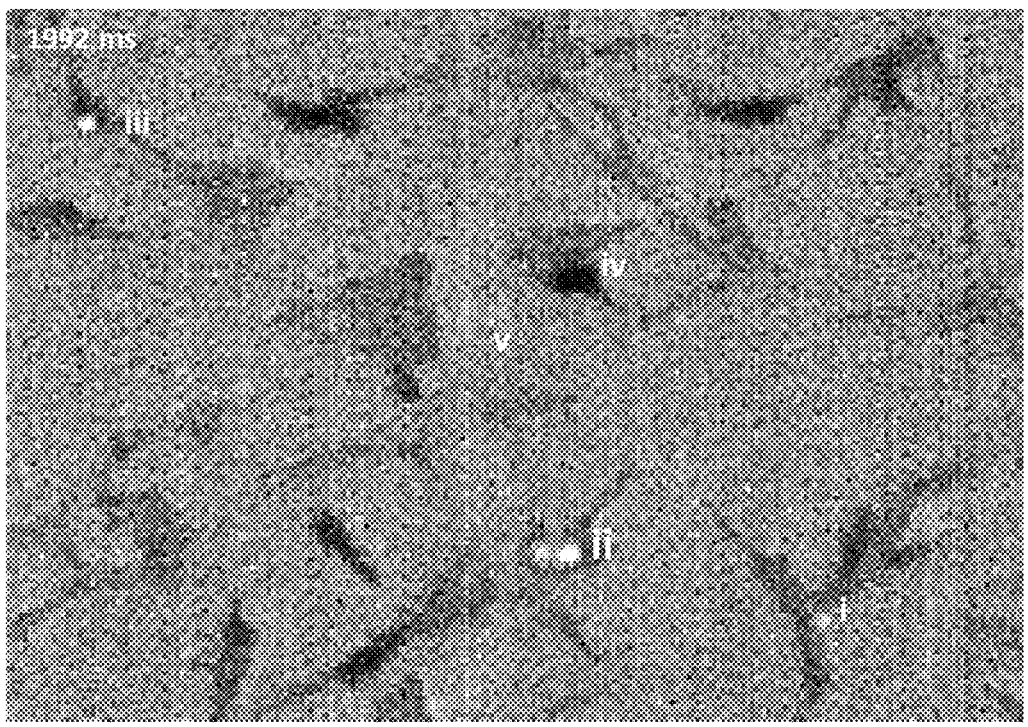
Figure 15C:
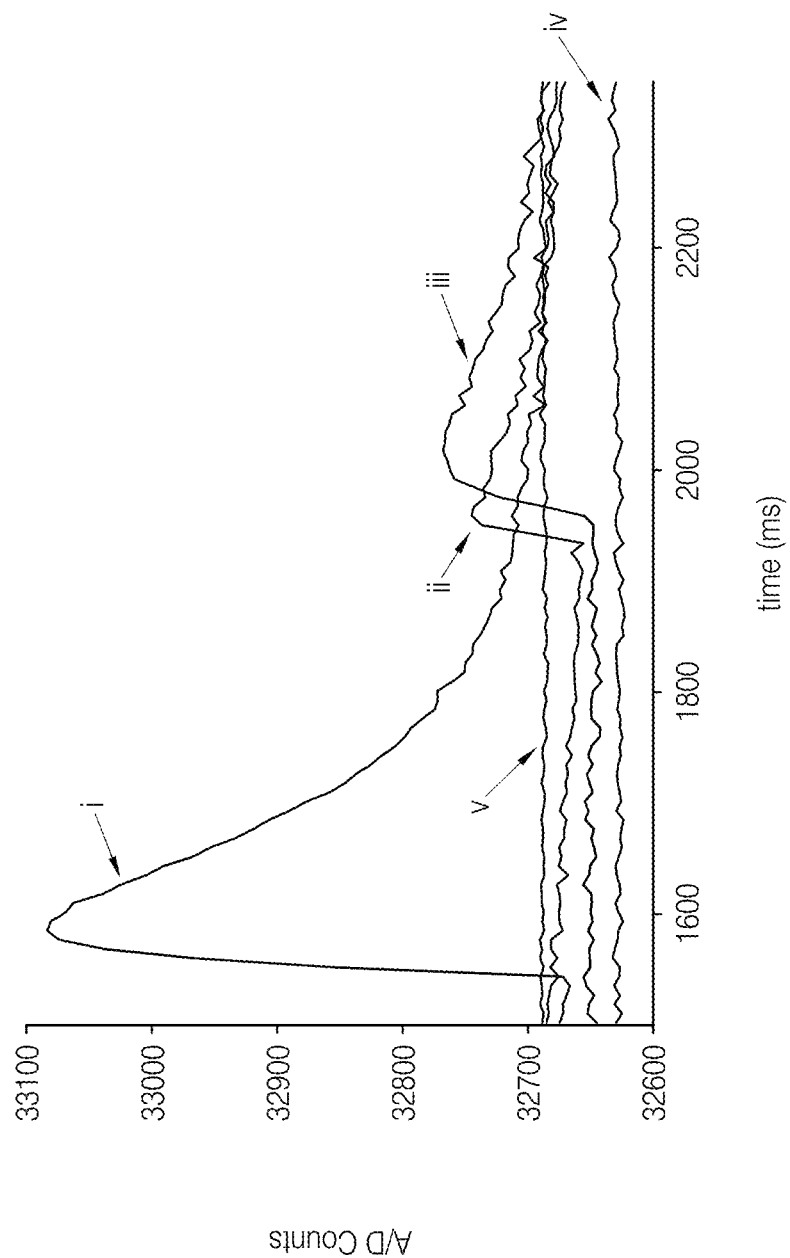
FIG. 15C is a temporal response curve over an interval including the time points for FIG. 15A and FIG. 15B.

The sensor array device used in experiments for which FIG. 15A through FIG. 15C are representative data was a Chip 1 device as summarized in the table of FIG. 3 selective for sensing hydrogen ion, and without a microwell array. In order to test the ability of various cell analysis systems of the present teachings to record cellular signals with subcellular resolution and high temporal fidelity, data was collected at 120 frames per second for a Chip 1 device with a substantial number of cells plated over a cell-compatible surface. The device and cell preparation were done as previously described for FIG. 9A through FIG. 9C. Briefly, the device was prepared with a poly-D-lysine surface and the preparation of U-2OS cells were transfected with voltage-gated calcium ion channels. The Chip 1 device was plated with the transfected U-2OS cells using a cell suspension of 1×10^6 cells per mL. As previously described herein, mammalianized BacMam gene delivery particles encode for a mixture of voltage-gated calcium ion channel alpha, beta and alpha-2-delta subunits to provide a cell suspension with reconstituted functional channels. Functional voltage-gated calcium ion channels require at a minimum of both alpha and beta subunits, with alpha-2-delta serving to boost surface expression and ionic flux.

Shown in FIGS. 15A and 15B are two electroscopic images from two exemplary time points that are separated by 345 milliseconds (ms) from data captured in an interval of about one to two seconds. Approximately 500 ms prior to the initiation of data collection, cells were perfused with the following isotonic reagent:
20 mM HEPES, pH 7.3
130 mM NaCl
12.5 mM KCl
1.8 mM $CaCl_2$
1.0 mM Mg $Cl_2$
Osmolarity: 300 mOsm FIG. 15A and FIG. 15B are electroscopic images displaying examples of transient signals in the subcellular domains of several cells presented in the electroscopic images. For example, for the cell designated as cell i, a signal is clearly visible at the 1577 ms time point, while the signal is substantially diminished at the 1922 ms time point. For the cell designated as cell ii, there is a prominently visible signal at the 1577 ms time point, while the signal is diminished at the 1922 ms time point to reveal a signal in a neighboring cell. For the cell designated as cell iii, there is no visible signal at the 1577 millisecond ms time point, while there is a signal that is clearly visible the 1922 ms time point.

FIG. 15C is a temporal response curve over a time interval that includes the time points for the electroscopic images for cells designated as cells i-iii in FIG. 15A and FIG. 15B. The temporal response curve of FIG. 15C also includes signals collected and averaged for non-responding cell iv; i.e. a cell response control, as well as signals collected and averaged for sensor area v; i.e. a device response control. As can be seen by inspecting the temporal response curve of FIG. 15C, both controls remained unchanged for the duration of data capture. As sampling intervals for data presented in FIG. 15A through FIG. 15C were at about 8.3 ms, a temporal response curve over the entirety of the experiment captured a rising phase and an exponential decay signal for numerous cells followed, as displayed for the exemplary cells shown in FIG. 15C. For the data presented in FIG. 15A through FIG. 15C, the high frame-rate recordings of subcellular domains reveal discrete areas of activity that are readily visualized, as shown in the electroscopic images of FIG. 15A and FIG. 15B, as well as quantified for number and intensity, as shown in the temporal response curve of FIG. 15C.

The impact of the data presented in FIG. 15A through FIG. 15C with subcellular resolution collected at a high frame rate is demonstration of cell activity in discrete microdomains that is consistent with bioelectric or biochemical activity. Cell activity in such microdomain regions is consistent with previous descriptions of localized vesicular release in TIRF microscopy. Additionally, the data also indicate the potential for various embodiments of ChemFET sensor array-based systems of the present teachings to assay for genetic or pharmacological interventions that may potentially control mechanisms underlying vesicular fusion and release in normal and diseased cell function.

As previously described herein for FIG. 3, sensor array device attributes that can be varied to provide a variety of sensor array devices of the present teachings include pixel dimensions, as well as the rate at which data can be collected from a sensor array device. FIG. 16 provides a similar summary for cells as described in the applications and methods section herein.

By inspection of FIG. 16, for an MMM cell anchored on a sensor array surface with an average diameter of 6 μm and average area of 28 μm$^2$, a minimum area of contact or footprint corresponds to about 2 rows and about 3 pixels for a Chip 1 device, which increases to 7 rows and 45 pixels for a Chip 4 device. Similarly, for a HEPG2 cell anchored on a sensor array surface with an average diameter of 15 μm and average area of 177 μm$^2$, a minimum area of contact or footprint corresponds to about 4 rows and about 18 pixels for a Chip 1 device, which increases to 18 rows and 285 pixels for a Chip 4 device. Similarly, for a HeLa cell anchored on a sensor array surface with an average diameter of 18 μm and average area of 254 μm$^2$, or a U-2OS cell with an average diameter of 19 μm and average area of 284 μm$^2$, a minimum area of contact or footprint corresponds to between about 5 rows and about 26 pixels, or to about 6 rows and about 29 pixels, respectively, for a Chip 1 device, which increases to between about 21 rows and 410 pixels, or to about 22 rows and 458 pixels, respectively, for a Chip 4 device. For an HASM cell anchored on a sensor array surface with an average diameter of 25 μm and average area of 491 μm$^2$, a minimum area of contact or footprint corresponds to about 7 rows and about 50 pixels for a Chip 1 device, which increases to 29 rows and 792 pixels for a Chip 4 device. Rat neonatal hippocampus (RNH) cells can have a cell body that can vary from between about 20 μm and average area of 314 μm$^2$ to about 100 μm and average area of 7,854 μm$^2$. For various RNH cells anchored on a sensor array surface a minimum area of contact or footprint of an RNH cell body can range between about 6 rows and about 32 pixels, to about 30 rows and about 803 pixels, respectively, for a Chip 1 device, which increases to range between about 24 rows and 506 pixels, to about 118 rows and 12,668 pixels, respectively, for a Chip 4 device. From inspection of FIG. 16, as was noted for FIG. 3, the trend is towards increasing pixel coverage with increasing cell size and decreasing pixel size.

From a pixel perspective, the column of percent pixel coverage is the percentage of area of a cell that a single pixel covers. For an MMM cell anchored on a sensor array surface, a single pixel corresponds to 33% coverage for a Chip 1 device, whereas for a Chip 4 device a single pixel corresponds to 2% coverage. For a HEPG2 cell anchored on a sensor array surface, a single pixel corresponds to 6% coverage for a Chip 1 device, whereas for a Chip 4 device a single pixel corresponds to 0.4% coverage. In comparison, for a HeLa cell anchored on a sensor array surface, a single pixel corresponds to 4% coverage for a Chip 1 device, whereas for a Chip 4 device a single pixel corresponds to 0.2% coverage. For a U-2OS cell anchored on a sensor array surface, a single pixel corresponds to 3% coverage for a Chip 1 device, whereas for a Chip 4 device a single pixel corresponds to 0.2% coverage. For various RNH cells anchored on a sensor array surface, single pixel coverage can range from 3% for an RNH cell with average diameter of 20 µm to 0.1% coverage an RNH cell with average diameter of 100 µm on a Chip 1 device. In comparison, for a Chip 4 device, a single pixel corresponds to 0.2% coverage for an RNH cell with average diameter of 20 µm to 0.008% coverage an RNH cell with average diameter of 100 µm. From inspection of FIG. 16, as was noted for FIG. 3, the trend is towards decreasing percentage of cell coverage per pixel with increasing cell size and decreasing pixel size.

Given what is presented in the table of FIG. 16, selection of pixel coverage for exemplary sensor array devices of the present teaching can be made for a variety of average cell diameters. The correlation of device attributes with cell lines used in various applications of the present teachings fall within the ranges as recited in FIG. 3. In that regard, for cells from about 5 µm to about 100 µm, a selection of sensor array devices can be made to provide coverage from about 8 pixels over 3 rows of pixels to about 12,668 pixels over 118 rows of pixels for a corresponding footprint of a cell anchored on a sensor array surface. Over that range of cell sizes, pixel sizes can vary, so that each pixel of a selected sensor array device can cover from between about 12% of a cell to about 0.008% of a cell. Based on the data presented in FIG. 3 and FIG. 16, it is evident that for any cell size, an exemplary sensor array device can be selected that can provide a substantial number of sensors associated with an area of contact that a cell can occupy on a sensor array device. The spatial resolution that can be provided by various sensor array devices of the present teachings can allow for subcellular discrimination of signals; hence providing for subcellular analysis.

Similarly, consistent with what is presented in FIG. 3, by inspection of the last column of FIG. 16, it is evident that a substantial number of frames per second can be collected for targeted areas of interest across a range of cell sizes, providing for data collection comfortably within the kHz range. Recalling, in the last column, the maximum frame rate that data can be collected for a fractional portion of rows covered by a cell is presented, as derived by a dividing maximum frame rate per row by rows per cell diameter.

For an MMM cell anchored on a sensor array surface, data can be collected at a maximum frame rate of 37,500 fps for a Chip 1 device, whereas for a Chip 4 data can be collected at a maximum frame rate of 23,142 fps. For an HEPG2 cell anchored on a sensor array surface, data can be collected at a maximum frame rate of 18,750 fps for a Chip 1 device, whereas for a Chip 4 data can be collected at a maximum frame rate of 9,000 fps. For a HeLa cell anchored on a sensor array surface, data can be collected at a maximum frame rate of 15,000 fps for a Chip 1 device, whereas for a Chip 4 data can be collected at a maximum frame rate of 7,714 fps. Similarly, for a U-2OS cell anchored on a sensor array surface, data can be collected at a maximum frame rate of 12,500 fps for a Chip 1 device, whereas for a Chip 4 data can be collected at a maximum frame rate of 7,364 fps. For an HASM cell anchored on a sensor array surface, data can be collected at a maximum frame rate of 10,714 fps for a Chip 1 device, whereas for a Chip 4 data can be collected at a maximum frame rate of 5,586 fps. Finally, for various RNH cells, a body of such cells anchored on a sensor array surface, data can be collected at a maximum frame rate of between about 2,500 fps to about 12,500 fps for a Chip 1 device, whereas for a Chip 4 data can be collected at a maximum frame rate of between about 1,373 fps to about 6,750 fps.

According to the present teachings, what presented in FIG. 16 makes clear that various maximum frame rates for cell lines used in various applications according to the present teachings fall within the range of about 1,250 fps to about 75,000 fps, as presented in FIG. 3. From inspection of FIG. 3 and FIG. 16, the trend is towards decreasing frame rate with increasing cell size and decreasing pixel size, which is consistent with the inverse relationship between an area of interest selected and the rate at which data can be collected. As such, by selecting a smaller subset of pixels to monitor, i.e. by windowing down the area of a sensor array device over which data is collected, or by selecting a device with a desirable frame rate matched to an application, frame rate can be increased.

What has been described herein relates to systems, applications and methods for various cell analysis systems based on chemical field effect transistor (ChemFET) sensor array technology. Various cell analysis systems of the present teachings can measure the electrical and metabolic activity of single, living cells with subcellular addressability and simultaneous data acquisition for between about 10 cells to about 500,000 cells in a single analysis. Various sensor array devices of the present teachings can have sensor arrays with between 20 million to 660 million ChemFET sensors built into a massively paralleled array, in which the sensors of a sensor array can have a pitch of between about 3.36 µm to about 850 nm, respectively. Further, various cell analysis systems of the present teachings can provide for simultaneous measurement of cells with data acquisition rates in the kilohertz (kHz) range. Moreover, a fully automated fluidic system integrated into various cell analysis systems of the present teachings allows for the tightly controlled application, for example, of chemical agents used in various studies for which the measurement of cell responses to various types of chemical interrogation is indicated. As various ChemFET sensor arrays of the present teachings can detect chemical analytes as well detect changes in cell membrane potential, controlled electrical stimulus can also be used to interrogate cells in various cell analysis systems of the present teachings.

While preferred embodiments of the present teachings have been shown and described herein, it will be obvious to those skilled in the art that such embodiments are provided by way of example only. Numerous variations, changes, and substitutions will now occur to those skilled in the art without departing from the present teachings. It should be understood that various alternatives to the various embodiments described herein may be employed in practicing the what is disclosed herein. It is intended that the following claims define the scope of the present disclosure and that systems, devices, applications and methods within the scope of these claims and their equivalents be covered thereby.

What is claimed is:

1. A cell analysis system comprising:
   a device including an array of chemical field effect transistor (ChemFET) sensors, wherein each pixel in the array of sensors provides between about 0.008% to about 12% coverage of a cell footprint for a range of cells with cell diameter of between about 100 μm to about 5 μm, respectively;
   an array of microwell structures disposed upon the array of sensors, each microwell structure having a height with a characteristic ratio to a width, and a bottom defined by a sensing surface;
   a flow cell mounted upon the device, wherein the flow cell is configured to provide a fluidic interface for the device with the cell analysis system;
   a reference electrode in flow communication with the flow cell, wherein the reference electrode is configured to provide a stable reference potential to the array of sensors; and
   an array controller configured to provide, power and bias voltages, as well as control and timing signals to the device, and provide data acquired from the device to a system processor.

2. The cell analysis system of claim 1, wherein the ChemFET sensors are ion selective field effect transistor (ISFET) sensors.

3. The cell analysis system of claim 2, wherein the ISFET sensors are selective for hydrogen ion.

4. The cell analysis system of claim 1, wherein the cell analysis system further comprises a fluidic system configured for controllable liquid deliver through the flow cell.

5. The cell analysis system of claim 1, wherein the device has a surface treated with a coating.

6. The cell analysis system of claim 5, wherein the coating is selected from poly-D-lysine, laminin, and combinations thereof.

7. The cell analysis system of claim 5, wherein the coating is an extracellular matrix preparation.

8. The cell analysis system of claim 1, wherein each microwell structure is coupled to at least one sensor.

9. The cell analysis system of claim 8, wherein the bottom of the microwell structure is not more than 90% the width of a sensor plate of a sensor in the array of sensors.

10. The cell analysis system of claim 9, wherein the height of microwell structures are between about twice to about quadruple the width of the microwell structures.

11. The cell analysis system of claim 1, further comprising a depolarizing electrode in flow communication with the device, wherein the depolarizing electrode is configured to apply an electrical stimulus to the cells.

12. The cell analysis system of claim 1, further comprising:
   control circuitry coupled to the device and configured to provide a frame rate per cell diameter of between about 1 kHz to about 75 kHz for a range of cells with a diameter of between about 100 μm to 5 μm, respectively.

13. The cell analysis system of claim 1, wherein the device comprises at least 20 million ChemFET sensors.

14. A method for cellular analysis comprising:
   plating a sample of cells on a sensor array surface of a ChemFET sensor array device; said sensor surface prepared to promote cell adhesion; wherein each cell in contact with the sensor array surface has a defined footprint on the sensor array surface;
   selecting an area of interest from an image of the sample of cells plated on the sensor array surface, wherein selecting the area of interest defines a frame rate for data acquisition;
   running a cell analysis application to acquire data for the selected area of interest at the defined frame rate; and
   displaying a result for the selected area of interest for the cell analysis application.

15. The method of claim 14, wherein the result displayed is an electroscopic image of at least one cell.

16. The method of claim 14, wherein the result displayed is a temporal response curve for at least one cell.

17. The method of claim 14, wherein the frame rate is about 1,250 fps for a cell with a footprint of covering about 30 rows of pixels.

18. The method of claim 14, wherein the frame rate is about 40,500 fps for a cell with a footprint of covering about 4 rows of pixels.

19. The method of claim 14, wherein before plating a sample the method further comprises selecting ChemFET sensor array device with a defined device frame rate.

20. The method of claim 19, wherein the defined device frame rate is between about 15 fps to about 240 fps.

21. The method of claim 14, wherein the ChemFET sensor array device has a sensor pitch of between about 850 nm to about 3.3 μm.

22. The method of claim 14, wherein before selecting an area of interest, the method further comprises:
   subjecting the sample of cells plated on the sensor array surface to a stimulus causing cell membrane depolarization; and
   displaying an electroscopic image of each responsive cell dispersed on the ChemFET sensor array.

23. The method of claim 14, wherein the sensor surface is prepared with a coating selected from poly-D-lysine, laminin, and combinations thereof.

24. The method of claim 14, wherein the sensor surface is prepared with a coating of an extracellular matrix preparation.

25. The method of claim 14, wherein the sensor array surface comprises an array of microwells.

26. The method of claim 25, wherein the sensor surface is prepared with a coating selected from poly-D-lysine, laminin, and combinations thereof.

27. The method of claim 25, wherein the sensor surface is prepared with a coating of an extracellular matrix preparation.

28. The method of claim 14, wherein the ChemFET sensor array device comprises at least 20 million ChemFET sensors.

29. The method of claim 14, wherein the result displayed is an electroscopic image including cellular efflux for at least one cell.

30. The method of claim 14, wherein selecting an area of interest from an image of the sample of cells comprises selecting an area of interest from a microscope image.

31. The method of claim 14, wherein selecting an area of interest from an image of the sample of cells comprises selecting an area of interest from an electroscopic image.

32. The method of claim 22, wherein selecting an area of interest from an image of the sample of cells comprises selecting an area of interest from the electroscopic image displayed.

* * * * *